(12) United States Patent
Broadt et al.

(10) Patent No.: US 10,954,492 B2
(45) Date of Patent: Mar. 23, 2021

(54) PROCESSES FOR PRODUCTION AND PURIFICATION OF NUCLEIC ACID-CONTAINING COMPOSITIONS

(71) Applicant: THE UNITED STATES OF AMERICA, as represented by the Secretary, Department of Health and Human Services, Bethesda, MD (US)

(72) Inventors: Trevor Lane Broadt, Frederick, MD (US); Samir Hussein Shaban, Ashburn, VA (US); Yueqing Xie, Clarksburg, MD (US); Jianwei Sean Zhu, Frederick, MD (US); George Mitra, Potomac, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 0 days.

(21) Appl. No.: 15/579,137

(22) PCT Filed: Jun. 10, 2016

(86) PCT No.: PCT/US2016/036888
§ 371 (c)(1),
(2) Date: Dec. 1, 2017

(87) PCT Pub. No.: WO2016/201224
PCT Pub. Date: Dec. 15, 2016

(65) Prior Publication Data
US 2018/0163182 A1 Jun. 14, 2018

Related U.S. Application Data

(60) Provisional application No. 62/173,777, filed on Jun. 10, 2015.

(51) Int. Cl.
*A61K 39/125* (2006.01)
*C12N 7/02* (2006.01)
*C12N 7/00* (2006.01)
*B01D 15/36* (2006.01)

(52) U.S. Cl.
CPC ............ *C12N 7/00* (2013.01); *A61K 39/125* (2013.01); *B01D 15/363* (2013.01); *C12N 7/02* (2013.01); *C12N 2770/32651* (2013.01)

(58) Field of Classification Search
None
See application file for complete search history.

(56) References Cited

U.S. PATENT DOCUMENTS

| 6,264,940 | B1 | 7/2001 | Gromeier et al. |
| 6,464,972 | B1 | 10/2002 | Gromeier et al. |
| 6,518,033 | B1 | 2/2003 | Gromeier et al. |
| 7,147,848 | B2 | 12/2006 | Gromeier et al. |
| 7,901,921 | B2 | 3/2011 | Coffey |
| 7,968,086 | B2 | 6/2011 | Gromeier et al. |
| 2004/0213805 | A1 | 10/2004 | Verheije |
| 2009/0017523 | A1 | 1/2009 | Weggeman et al. |
| 2009/0246216 | A1 | 10/2009 | Wimmer et al. |
| 2013/0149279 | A1* | 6/2013 | Brady ............... A61P 35/00 424/85.2 |

FOREIGN PATENT DOCUMENTS

| CN | 1616095 A | 5/2005 |
| CN | 1816619 A | 8/2006 |
| CN | 1922308 A | 2/2007 |
| JP | 58-500589 | 4/1983 |
| JP | 5-503634 | 6/1993 |
| JP | 2006-528886 | 12/2006 |
| WO | WO 1982/003632 A1 | 10/1982 |
| WO | WO 1992/003538 A1 | 3/1992 |
| WO | WO 2004/112707 A2 | 12/2004 |
| WO | WO 2004/113494 A2 | 12/2004 |
| WO | WO 2005/080556 A2 | 9/2005 |
| WO | WO 2014/081937 A2 | 5/2014 |
| WO | WO 2016/012445 A2 | 1/2016 |
| WO | WO 2017/023782 A1 | 2/2017 |

OTHER PUBLICATIONS

Oksanen et al., Monolithic ion exchange chromatographic methods for virus purification, 2012, Virology, vol. 434, pp. 271-277.*
Kovac et al., A novel method for concentrating hepatitis A virus and caliciviruses from bottled water, 2009, Journal of Virological Methods, vol. 162, pp. 272-275.*
Gronneier et al., Internal ribosomal entry site substitution eliminates neurovirulence in intergeneric poliovirus recombinants, 1996, PNAS, vol. 93, pp. 2370-2375.*
Bakker et al., "Inactivated polio vaccine development for technology transfer using attenuated Sabin poliovirus strains to shift from Salk-IPV to Sabin-IPV", *Vaccine* 29:7188-7196, 2011.
Burrill et al., "Poliovirus: Generation, Quantification, Propagation, Purification, and Storage," in *Curr Protoc Microbiol.*, May 2013, John Wiley & Sons, Inc., Hoboken, NJ.

(Continued)

*Primary Examiner* — Benjamin P Blumel
(74) *Attorney, Agent, or Firm* — Klarquist Sparkman, LLP

(57) ABSTRACT

Described are improved processes for production and purification of nucleic acid-containing compositions, such as non-naturally occurring viruses, for example, recombinant polioviruses that can be employed as oncolytic agents. Some of the described improved processes relate to improved processes for producing viral DNA template. Also described are improved processes for chromatography purification of nucleic acid-containing compositions, in which the nucleic acid is quantified in chromatography fractions using a rapid detection method of the one or more nucleic acid sequences of the nucleic acid-containing composition, such as detection by real time RT-qPCR. In addition, improved processes for production and purification of oncolytic poliovirus, such as PVS-RIPO, are described. Compositions generated using these methods are also provided.

21 Claims, 30 Drawing Sheets

Specification includes a Sequence Listing.

(56) References Cited

OTHER PUBLICATIONS

Cello et al., "Growth phenotypes and biosafety profiles in poliovirus-receptor transgenic mice of recombinant oncolytic polio/human rhinoviruses," *J Med Virol.* 80:352-359, 2008.
Chumakov, "Evaluation of Safety and Potency of Viral Vaccines Based on Analysis of Molecular Consistency," http://www.fda.gov/BiologicsBloodVaccines/ScienceResearch/BiologicsResearchAreas/ucm127312.htm, retrieved from internet Jun. 7, 2016.
Dobrikova et al., "Attenuation of neurovirulence, biodistribution, and shedding of a poliovirus:rhinovirus chimera after intrathalamic inoculation in *Macaca fascicularis*," J Virol. 86:2750-2759, 2012.
Dobrikova et al., "Recombinant Oncolytic Poliovirus Eliminates Glioma In Vivo Without Genetic Adaptation to a Pathogenic Phenotype," *Mol Ther.* 16:1865-1872, 2008.
Farkas et al., "A Gel Filtration-Based Method for the Purification of Infectious Rotavirus Particles for Environmental Research Applications", *Food Environ Virol.* 5:231-235, 2013.
Gagnon, The Emerging Generation of Chromatography Tools for Virus Purification, *BioProcess International Supplement*, pp. 24-30, Oct. 2008.
GE Healthcare, "Purification Technologies for Vaccines and Vectors," GE Healthcare Bio-Sciences AB, Uppsala, Sweden, 2007.
Goetz & Gromeier, "Preparing an oncolytic poliovirus recombinant for clinical application against glioblastoma multiforme," *Cytokine Growth Factor Rev.* 21:197-203, 2010.
Gromeier et al., "Expression of the human poliovirus receptor/CD155 gene during development of the central nervous system: implications for the pathogenesis of poliomyelitis," *Virology* 273:248-257, 2000.
Heider & Metzner, "Quantitative real-time single particle analysis of virions" *Virol.* 462:199-206, 2014.
Jacoby et al., "Advanced Biopharmaceutical Manufacturing: An Evolution Underway," downloaded from https://www.gelifesciences.com/gehcls_images/Gels/Related%20Content/Files/1314774443672/litdoc28908405_20130905164505.pdf, Deloitte Development LLC, 2015 (16 pages).
Kaufman et al., "Oncolytic viruses: a new class of immunotherapy drugs," *Nat Rev Drug Discov.* 14:642-662, 2015.
Levintow & Darnell, "A Simplified Procedure for Purification of Large Amounts of Poliovirus: Characterization and Amino Acid Analysis of Type 1 Poliovirus," *J Biol. Chem.* 235:70-73, 1960.
Li et al., "A Sabin 1 poliovirus-based vaccine vector transfects Vero cells with high efficiency," *Cytotechnology* 54:169-179, 2007.
Luo et al., "A protocol for rapid generation of recombinant adenoviruses using the AdEasy system ," *Nature Protocols* 2:1236-1247, 2007.
Milne et al., "Porcine HveC, a Member of the Highly Conserved HveC/Nectin-1 Family, is a Functional Alpha-herpesvirus Receptor," *Virology* 281:315-328, 2001.
Ouellette et al., "Large-Scale Chromatographic Purification of an Attenuated Chimeric Poliovirus," *BioProcessing J.* 4:31-38, 2005.
Pu et al., "Successful Propagation 21,23-25 of Flavivirus Infectious cDNAs by a Novel Method to Reduce the Cryptic Bacterial Promoter Activity of Virus Genomes," *J Virol.* 85:2927-2941, 2011.
Thomassen et al., "Next Generation Inactivated Polio Vaccine Manufacturing to Support Post Polio-Eradication Biosafety Goals," *PLoS One* 8:e83374, 2013.
Wolf and Reichl, "Downstream processing of cell culture-derived virus particles," *Expert Rev. Vaccines* 10:1451-1475, 2011.
Yang et al., "Porcine circovirus (PCV) removal by Q sepharose fast flow chromatography," *Biotechnol Prog.* 29:1464-1471, 2013.
Yang et al., "Evaluation of IRES-Mediated, Cell Type-Specific Cytotoxicity of Poliovirus Using a Colorimetric Cell Proliferation Assay," *J Virol. Methods* 155:44-54, 2009.
PCT/US2016/036888 International Search Report and Written Opinion dated Oct. 10, 2016 (15 pages).
CN 1616095 A, English translation submitted herewith.
JP 2006-528886, WO 2004/113494 A2 submitted herewith.
JP 5-503634, WO 1992/003538 A1 submitted herewith.
JP 58-500589, WO 1982/003632 A1 submitted in IDS filed Dec. 1, 2017.
Greninger et al., "A metagenomic analysis of pandemic influenza A (2009 H1N1) infection in patients from North America," *PloS One* 5:e13381, 2010.
Neverov and Chumakov, "Massively parallel sequencing for monitoring genetic consistency and quality control of live viral vaccines," *Proc Natl Acad Sci U.S.A.* 107:20063-20068, 2010.
Ochiai et al., "Utilization of next generation sequencer in virus field, Analysis of polio virus mutation rate by next generation sequencer," *Clin Virol* 43:117-122, 2015 (with English translation).
Muramatsu, Masami, ed., Bunshi saibo seibutsu gaku jiten (Dictionary of molecular and cellular biology), Tokyo Kagaku Dojin, p. 486, Feb. 2002 (with English translation).
TaKaRa Bio general catalog 2002-2003, p. R-21.

* cited by examiner

Marker    Reference    Lot 1    Lot 2

FIG. 10

CERTIFICATE OF ANALYSIS

Product Name: E. coli DH5 Alpha Master Cell Bank  Project Number: 044
BQAD Tracking Number: 10902   NSC Number: N/A   Part Number: 10291   Lot Number: L0301014
Production Date:    Storage Temperature: ≤-70 °C
Lot Size: 144 cryo vials   Fill Volume / Container: 1.0 ml fill / 2.0 ml cryo vial
Description: Master Cell Bank of E. coli DH5 Alpha produced from Invitrogen E. coli DH5 Alpha Lot 1159251. Host strain for future production.

| Test Description | Assay Specification | Test SOP # or Study # | QC Test Request Number | Result |
|---|---|---|---|---|
| Identity | | | | |
| Gram Stain | Gram negative | 00638 | 017291 | Gram negative rods |
| Identity of Bacteria | E. coli | Accugenix Bacterial Identification 500bp MicroSeq | 017290 | E. coli / Shigella* Shigella excluded by absence of toxin gene |
| Organism Identification by RiboPrinting | Homologous to E. coli reference | Lancaster Laboratories 2815 | 017292 | Homologous to non-toxic (Dupont) E. coli reference strain #101 |
| Antibiotic Resistance | No resistance to kanamycin and chloramphenicol | CBI SAIC# 6613-017 | 017293 | No colonies resistant to kanamycin or chloramphenicol |
| Purity | | | | |
| Culture Purity and Colony Morphology | No non-conforming organisms observed, uniform colony morphology | 00693 | 017280 | Uniform colony morphology (no non-conforming organisms) |
| Cell Viability | ≥ 1 X 10⁵ cfu/ml | CBI SAIC# 6613-017 | 017288 | 5.7 X 10⁵ cfu/ml |
| Safety | | | | |
| Shiga-like Toxin / Toxin Gene Detection | Negative for toxin genes | Penn State G.O.C. Lot # 13.09.03 | 017287 | Negative for toxin genes* |
| Lytic or Lysogenic Bacteriophage | Negative for bacteriophage | | 017285 | Negative for bacteriophage |

FIG. 11 CERTIFICATE OF ANALYSIS

Product Name: E. coli DH5 Alpha Working Cell Bank (Competent)   Project Number: 904   Part Number: 10306

NSC Number: N/A   Lot Number: L0303011   Lot Size: 95 cryo vials   Production Date:

Fill Volume / Container: 0.15 ml fill / 2.0 ml cryo vial   Storage Temperature: ≤ -70 °C Description: Working Cell Bank of E. coli DH5 Alpha produced from BDP E. coli DH5 Alpha MCB Lot L03010014. Host strain for future production.

| Test Description | Assay Specification | Test SOP # or Study # | QC Test Request Number | Result |
|---|---|---|---|---|
| Identity | | | | |
| Gram Stain | Gram negative | 00636 | 017560 | Gram negative rods |
| Identity of Bacteria | E. coli | Accugenix SOP 6.23 | 017559 | E. coli |
| Purity | | | | |
| Culture Purity and Colony Morphology | No non-conforming organisms observed, uniform colony morphology | 00690 | 017561 | Uniform colony morphology (no non-conforming organisms) |
| Cell Viability | ≥ 1 X 10$^5$ cfu/ml | CBI SAdC 00670 | 017562 | 2.4 X 10$^9$ cfu/ml |
| For Information Only | | | | |
| Transformation Competency | | | | |
| Transformation Efficiency | Report Results. Expect at least 1 x 10$^8$ cfu/μg plasmid DNA pUC 19 | BDP Bacterial Development Laboratory | 017668 | 1 X 10$^7$ cfu/μg plasmid DNA |

FIG. 12

| Product Name: | PVS-RIPO Plasmid DNA | | Project Number: | LO401014 | Part Number: 50113 |
|---|---|---|---|---|---|
| NSC Number: | 719227 | | Lot Number: | LO401014 | Lot Size: 19 Vials |
| Production Date: | | | Container Size/Fill Volume: 2 mL/1mL | | Storage Temperature: ≤ -70 °C |
| Description: | PVS-RIPO Plasmid DNA at a concentration of 0.5mg/mL in a solution of 10mM Tris, 1mM EDTA, pH 8 | | | | |

| Test Description | Assay Specification | Test SOP # or Study # | QC Test Request Number | Result |
|---|---|---|---|---|
| Identity | | | | |
| DNA Sequence | 100% homologous to PVS-RIPO reference sequence | Commonwealth Biotechnologies Inc. | QC-020658 | 100% Homologous to PVS-RIPO Plasmid Reference Lot L0305007 |
| Content | | | | |
| DNA Content by Absorbance at 260nm | ≥ 0.25 mg/mL $E^{1mg/mL}_{260nm}=20$ | 01114 | QC-020654 | 0.304 mg/mL |
| Purity | | | | |
| A260nm / A280nm Ratio | 1.75 to 2.00 | 01114 | QC-020654 | 1.870 |
| Residual Protein by BCA Assay | ≤ 50 μg/mL | 00679 | QC-020657 | < 5 μg/mL (below limit of assay quantitation) |
| FOR INFORMATION ONLY | | | | |
| Total Size (Linearized DNA) | Report Results. Expected to conform with approximate size predicted from plasmid map following unique site restriction digest with Sal I, Linear, 1 fragment, 9945bp | 00676, 00689, 22120 | QC-020659 | Calculated Sal I (linear) band size:9957 |
| Restriction Map | Report Results. Expected to conform with Mun I restriction pattern predicted by the nucleotide sequence (4 bands, 1537, 2220, 2907, and 3281 bp) | 00676, 00689, 22120 | QC-020655 | Mun I and 9 other restriction enzymes band patterns concordant with expected band patterns |
| Percent supercoiled plasmid DNA by agarose gel electrophoresis | Report Results | 00689, 22120 | QC-020660 | 90.5%scDNA |
| Residual E. coli genomic DNA by PCR | Report Results | 22901 | QC-020661 | 7.25μg/mL E. coli gDNA (2.42% gDNA) |
| Residual RNA by Agarose Gel | Report Results | 00689, 22120 | QC-020662 | No RNA observed at 5pg/lane gel load |

FIG. 13

| | Testing |
|---|---|
| Linearization of PVSRIPO Plasmid DNA Lot L0401014 | DNA Agarose Gel Electrophoresis |
| ↓ | |
| Purification of the Linear Plasmid DNA | DNA Agarose Gel Electrophoresis |
| ↓ | |
| *In Vitro* Transcription Producing PVSRIPO RNA Lot L0402001 Store ≤ -70°C | RNA Agarose Gel Electrophoresis |

Culture of Vero Cells for Electroporation from WCB Lot 217002-2
↓
Harvest of Vero Cells for Electroporation
→
Vero Cell Transfection with PVSRIPO RNA by Electroporation Lot L0402026 Store ≤ -70°C
↓
Transfected Vero Cells expanded in DMEM/F12 Medium (20 T75 Flasks) at 33°C and 5% CO$_2$
↓
Harvested PVSRIPO virus by centrifugation. Collected supernatant Initial Virus Seed Lot L0402026 (P0) Store ≤ -70°C Virus Titer
Microbial Content

FIG. 14

AMENDED CERTIFICATE OF ANALYSIS[2]
WHO VERO Master Cell Bank

Page 1 of 2

Cell line: WHO VERO MCB
Part number: 5.40115
Lot number: 2003-0049

Date of cell bank freeze: 
Fill volume (mL/vial): 1 mL
Product concentration: Approximately $9.5 \times 10^6$ viable cells/vial (post thaw)
Store in liquid nitrogen

| Test | | | |
|---|---|---|---|
| Test for the Presence of Agar-Cultivable and Non-Cultivable Mycoplasmas | R96BY19.102003 | Pass | Pass |
| Test for the Presence of Bacterial and Fungal Contaminants: Sterility Test Using a Direct Inoculation Method | R96BY19.510 | Pass | Pass |
| Cell Culture Identification and Characterization | C96BY19.380 | African Green Monkey | African Green Monkey |
| Growth of Mammalian Cells in Soft Agarose | B96BY19.029 | Report Result | None Detected |
| In Vitro Assay for the Presence of Viral Contaminants | R96BY19.003 | None Detected | None Detected |
| Test for the Presence of Inapparent Viruses – In Vivo | B96BY19.005002 | None Detected | None Detected |
| Transmission Electron Microscopic Evaluation of Cultured Cells | B96BY19.013 | Report Result | No Identifiable Virus-Like Particles |
| Test for the Presence of Retrovirus-Raji Co-Cultivation | B96BY19.015008 | None Detected | None Detected |
| MA-PERT Assay[1] (non-GLP) | B96BY19.002001 | Negative | Negative |
| In Vitro Detection of Retroviruses by Assay for Reverse Transcriptase Activity[2] | B96AE27.002 | Negative | Negative |
| PCR Assay for Detection of Simian Virus 40 (SV40) in Biological Samples[2] | B98AE27.105028 | Negative | Negative |

[1] Product Enhanced Reverse Transcriptase Assay
[2] Certificate of Analysis amended to include In Vitro Detection of Retroviruses by Assay for Reverse Transcriptase Activity and PCR Assay for Detection of Simian Virus 40 (SV40) in Biological Samples 01/02/02.

FIG. 15     CERTIFICATE OF ANALYSIS

Product Name: Vero Working Cell Bank     Project Number: 217     Part Number: 10395

NSC Number: N/A     Lot Number: 217002-2     Lot Size: 440 vials     Production Date:

Container/Fill Volume: 2 mL/1mL     Storage Temperature: ≤ -70°C     Storage Conditions: Vapor Phase Liquid Nitrogen Description: Mammalian Cell Working Cell Bank of Monkey Kidney (Vero) Cells derived from WHO VERO MCB P139 P/N 5.40115, L/N 2003-0049 made at MAGENTA Corporation (BioReliance). WCB Cells are at passage 142.

| Test Description | Assay Specification | Test SOP # or Study # | QC Test Request Number | Result |
|---|---|---|---|---|
| Identity | | | | |
| Isoenzyme | Conforms to Monkey origin | 380001 BioReliance | QC-09944 | Conforms to Monkey origin |
| Safety | | | | |
| Sterility | No Growth | USP 23, 510036 BioReliance | QC-09942 | No Growth |
| Mycoplasma | Free of Mycoplasma | 102003 BioReliance | QC-09943 | Free of Mycoplasma |
| In Vitro Adventitious Agents | No viral contaminants detected | 003000 BioReliance | QC-09945 | No viral contaminants detected |
| In Vivo Adventitious Agents | No viral contaminants detected | 005002 BioReliance | QC-09946 | No viral contaminants detected |
| Bovine and Porcine Adventitious Agents | No viral contaminants detected | 30640 AppTec | QC-018195 | No viral contaminants detected |
| STLV | No STLV detected | 37119 Q-One | QC-018199 | No STLV detected |
| SIV | No SIV detected | 37110 Q-One | QC-018198 | No SIV detected |
| Simian Foamy Virus | No Simian Foamy Virus detected | 37153 Q-One | QC-018197 | No Simian Foamy Virus detected |
| In Vivo Tumorigenicity | Non-Tumorigenic | 401 Anmed | QC-019640 | Non-Tumorigenic |

FIG. 17

Certificate of Analysis
Page 1 of 2

| Product Name: | PVS-RIPO Master Virus Seed | Project Number: 417 | | Part Number: 50139 |
|---|---|---|---|---|
| NSC Number: | 719277 | Lot Number: L0403006 | | Lot Size: 24 Bottles |
| Production Date: | | Container Size/Fill Volume: 125 mL / 80 mL | | Storage Temperature: ≤ -70 °C |
| Description: | Master Virus Seed bank of PVS-RIPO (Chimeric poliovirus). Passage P1 on VERO cells Lot #217002-2. | | | |

| Test Description | Assay Specification | Test SOP # or Study # | QC Test Request # | Result |
|---|---|---|---|---|
| Identity | | | | |
| Full genome sequence | Homologous to PVS-RIPO reference sequence | Commonwealth Biotechnologies, Inc. 8613.055 | QC-022271 | 100% homologous to PVS-RIPO Viral Sequence in reference plasmid from Lot L0401014 |
| Biological Assay - Differential Killing | Report Results | Bioanalytical Development Lab | QC-027227 | No cell killing was detected in HEK 293 cells with MOIs up to 1.0 Inhibited U87-MG proliferation |
| Potency | | | | |
| Virus titer by $TCID_{50}$ Assay | Report Results | BQC 22165 | QC-022273 | 8.50 log10 $TCID_{50}$/mL |
| Content | | | | |
| Titer by Plaque Assay @ 33°C | Report Results | BQC 22163 | QC-021501 | $1.02 \times 10^7$ pfu/mL |
| Safety | | | | |
| Sterility | No Growth | AppTec 30744 (21 CFR 610.12). Direct inoculation | QC-027229 | Negative for growth. |
| B&F | Non-bacteriostatic / Non-fungistatic | AppTec 30736 (USP). Direct inoculation | QC-027229 | Non-bacteriostatic / Non-fungistatic |
| Mycoplasma | Free of Mycoplasma | AppTec 30200 | QC-027228 | Negative for mycoplasma |
| Endotoxin | < 10 EU/mL | BQC 22135 | QC-027226 | < 0.05 EU/mL |
| In Vitro Adventitious Agents | No adventitious viral contaminants detected | BQC 22143 | QC-027794 | No adventitious viral agents found. |
| In Vivo Adventitious Agents | No adventitious viral contaminants detected | AppTec 30027I, 30193F | QC-027795 | No adventitious viral agents found. |
| Human Virus by PCR | | | | |
| Measles | None detected | BQC- Molecular Biology Lab 22901 | QC-029242 | None detected |
| Epstein-Barr Virus (EBV) | None detected | AppTec 30713 | QC-027803 | None detected |
| Cytomegalovirus (CMV) | None detected | AppTec 30705 | QC-027797 | None detected |
| Hepatitis B Virus (HBV) | None detected | AppTec 30703 | QC-027801 | None detected |
| Hepatitis C Virus (HCV) | None detected | AppTec 30730 | QC-027799 | None detected |
| Human Immunodeficiency Virus (HIV I) | None detected | AppTec 30635 | QC-027800 | None detected |
| Human Immunodeficiency Virus (HIV II) | None detected | AppTec 30770 | QC-027798 | None detected |
| HTLV I & II | None detected | AppTec 30985 | QC-027796 | None detected |
| B19 | None detected | AppTec 30761 | QC-027802 | None detected |
| Virus stability by rct40 | > 5-log reduction @ 40°C to 36°C | BQC 22173 | QC-027225 | 5.74-log reduction at 40°C to 36°C |

Continued to next page

FIG. 19

CERTIFICATE OF ANALYSIS
Page 1 of 1

| | | | | |
|---|---|---|---|---|
| Product Name: PVSRIPO Harvest Pool | | Project Number: 417 | | Part Number: 50206 |
| NSC Number: 719277 | Production Date: | Lot Number: L0904008 | Lot Size: | 10 10-Tier Cell Factories |
| Container Size/Fill Volume: 10L media bag/ 7.4L fill | | | Storage Temperature: ≤-70°C | |
| Description: PVSRIPO infected Vero cells, Lot #217002-2, passage P2. | | | | |

| Test Description | Assay Specification | Test SOP # or Study # | QC Test Request Number | Result |
|---|---|---|---|---|
| Potency | | | | |
| Virus Titer (TCID$_{50}$ Assay) | Report results | BQC 22165 | QC-041377 | 9.33(log$_{10}$) TCID$_{50}$/mL; equivalent to 2.14 x 10$^9$ TCID$_{50}$/mL |
| Safety | | | | |
| Extended Bioburden | < 20 CFU/mL; no pathogenic organisms | BQC 22133 | QC-041102 | No growth (0 CFU/mL) |
| Detection of Mycoplasma (PTC) using NIH/3T3 cells | None detected | AppTec 30200 | QC-041378 | None detected |
| Endotoxin by LAL | Report results | BQC 22204 | QC-041376 | < 0.5 EU/mL |
| Virus Stability by rct40 | ≥ 5 log reduction in titer at 40°C from 36°C | BQC 22173 | QC-041375 | ≥ 7.21 log reduction in titer |
| *In vivo* Adentitious Agents | No viral contaminants detected | AppTec 30027 | QC-041379 | No viral contaminants detected |

FIG. 20

CERTIFICATE OF ANALYSIS
Page 1 of 1

| | | | | |
|---|---|---|---|---|
| Product Name: PVSRIPO Purified Sterile Bulk | | Project Number: 417 | | Part Number: 50211 |
| NSC Number: 719277 | Production Date: | Lot Number: L0904009 | Lot Size: | 1 PETG Bottle |
| Container Size/Fill Volume: 1L / 283 mL | | | Storage Temperature: ≤-70°C | |
| Description: PVSRIPO purified sterile bulk in 50 mM sodium phosphate, 0.9% NaCl, pH 7.4, 0.2% HSA. Passage P2 on Vero Cell Lot #217002-2. | | | | |

| Test Description | Assay Specification | Test SOP # or Study # | QC Test Request Number | Result |
|---|---|---|---|---|
| Identity | | | | |
| Full genome sequence | Homologous to PVSRIPO reference sequence[1] | American International Biotechnology, Inc., Study #SAIC-120809-LD | QC-042162 | 100% homologous to the PVSRIPO reference sequence[1] |
| Purity | | | | |
| Host Cell DNA (Vero) | Report results | BQC 22195 | QC-042166 | None detected, < 0.5 ng/mL |
| Residual Benzonase | Report results | AppTec 38067 | QC-042167 | 1.6 ng/mL |
| Total Protein by BCA[2] | Report results | BQC 22107 | QC-041179 | < 5 µg/mL protein |
| Potency | | | | |
| Differential Killing | Report results | BQC 16116 | QC-042164 | No cell killing detected in HEK 293 cells with MOIs up to 10 TCID$_{50}$/cell; Cytotoxic to U87-MG cells (ED$_{50}$ = 0.041 MOI) |
| Virus Titer (TCID$_{50}$ Assay) | Report results | BQC 22165 | QC-042165 | 9.67(log$_{10}$) TCID$_{50}$/mL; Equivalent to 4.68 x 10$^9$ TCID$_{50}$/mL |
| Safety | | | | |
| Sterility (Direct Inoculation) | No growth | AppTec 30744, 21 CFR 610.12 | QC-042168 | No growth |
| Bacteriostasis/Fungistasis (post-sterility) | Non-bacteriostatic/Non-Fungistatic | AppTec 30736, 21 CFR 610.12 | QC-042168 | Non-bacteriostatic/Non-Fungistatic |
| Endotoxin by LAL | ≤ 10 EU/mL | BQC 22204 | QC-042163 | < 0.5 EU/mL |

FIG. 21

CERTIFICATE OF ANALYSIS
Page 1 of 1

| Product Name: | PVSRIPO Final Vialed Product | Project Number: 417 | | Part Number: 50217 |
|---|---|---|---|---|
| NSC Number: | 719277 | Production Date: | Lot Number: L0904010 | Lot Size: 435 vials |
| Container Size/Fill Volume: | 2mL glass / 0.5mL | | | Storage Temperature: ≤-70°C |
| Description: | Vialed PVSRIPO virus in 50 mM sodium phosphate, 0.9% NaCl, pH 7.4, 0.2% HSA. Passage P2 on Vero Cell Lot #217002-2. | | | |

| Test Description | Assay Specification | Test SOP # or Study # | QC Test Request Number | Result |
|---|---|---|---|---|
| Appearance | | | | |
| Clarity, Color, and Appearance | Clear to translucent, colorless liquid with no evidence of particulate matter | BQC 22925 | QC-042169 | Clear, colorless liquid with no particulate matter |
| Identity | | | | |
| Full genome sequence | Homologous to PVSRIPO reference sequence[1] | American International Biotechnology, Inc., Study #SAIC-120809-LD | QC-042162 | 100% homologous to the PVSRIPO reference sequence[1] |
| RT-qPCR (HRV-2 IRES and Polio Polyprotein) | Positive for HRV-2 IRES and Polio Polyprotein sequences; Report viral copy number | BQC 22195 | QC-042170 | Positive for HRV-2 IRES and Polio Polyprotein sequences; $5.01 \times 10^{10}$ viral copies/mL |
| Content | | | | |
| Virus Titer (TCID$_{50}$ Assay) | Report results | BQC 22165 | QC-042165 | $9.60(\log_{10})$ TCID$_{50}$/mL; Equivalent to $4 \times 10^9$ TCID$_{50}$/mL |
| Safety | | | | |
| pH | $7.4 \pm 0.5$ | BQC 22124 | QC-042171 | 7.

FIG. 22

CERTIFICATE OF ANALYSIS
Page 1 of 2

| Product Name: | PVSRIPO Toxicology Material | | Project Number: 417 | | Part Number: 50247 |
|---|---|---|---|---|---|
| NSC Number: | 719277 Lot Number: L0603006 | | Lot Size: 281 vials | | Storage Temperature: ≤-70°C |
| Production Date: | | | Container Size/Fill Volume: 3 mL glass vial / 0.5 mL fill | | |
| Description: | Purified recombinant PVSRIPO in 50mM sodium phosphate, 0.9% NaCl pH 7.4, 0.2% HSA. Passage P2 on Vero cells. | | | | |

| Test Description | Assay Specification | Test SOP # or Study # | QC Test Request Number | Result |
|---|---|---|---|---|
| Appearance | | | | |
| Clarity, Color, and Appearance | Clear to opalescent @ RT, colorless liquid with no evidence of particulate matter. | BQC 22925 | QC-029922 | Clear, colorless liquid with no evidence of particulate matter |
| Identity | | | | |
| Full Genomic Sequence | Conforms to Master Virus Bank, Lot L0403006 | Commonwealth Biotechnologies, Inc. Study 8613.096 | QC-029927 | Sequence conforms to PVSRIPO Master Virus Bank, Lot L0403006 |
| Purity | | | | |
| Residual Benzonase[1] | Report results | AppTec 36067 | QC-029930 | < 0.25 ng/mL |
| Total Protein by BCA[1] | Report results | BQC 22107 | QC-029924 | < 5 µg/mL protein |
| Content | | | | |
| Infectious Titer by $TCID_{50}$ | Report results | BQC 22165 | QC-029921 | 10.31($log_{10}$) $TCID_{50}$/mL |
| Virus Particle by EM | Report results | BQC 22904 | QC-029928 | $3.98 \times 10^{12}$ vp/mL |
| Ratio VP/IU | Report results | Calculation | N/A | 195 |
| Potency | | | | |
| Differential Killing | Report results | Bioanalytical Development, 16116 | QC-029926 | No cell killing was detected in HEK 293 cells with MOIs up to 10 $TCID_{50}$/cell, cytotoxic to U87-MG cells. |
| Safety | | | | |
| Sterility (direct inoculation) | No growth at 14 days | AppTec 30744, 30744A 21 CFR 610.12 | QC-029931 | No growth at 14 days |
| Bacteriostasis/Fungistasis (post-sterility) | Non-bacteriostatic/Non-Fungistatic | AppTec 30736, cUSP <71> | QC-029931 | Non-bacteriostatic/Non-Fungistatic |
| Endotoxin | ≤ 10 EU/mL | BQC 22135 | QC-029925 | 0.09 EU/mL |
| Virus stability by rct40 | >5 log reduction @ 40°C to 36°C | BQC 22173 | QC-029929 | 7.40 log reduction in titer at 40°C when compared to titer at 36°C |
| pH | 7.4 ± 0.9 @ RT | BQC 22124 | QC-029923 | 7.4 |

[1] Samples taken prior to final formulation with HSA.

FIG. 23

```
┌─────────────────────┐     ┌─────────────────────┐
│ Vero Working Cell   │───▶ │ PVSRIPO Master Virus│
│ Bank Lot 217002-2   │     │   Seed Lot L0403006 │
└─────────────────────┘     └──────────┬──────────┘
                                       │
                         ┌─────────────┴─────────────┐
                         ▼                           ▼
                ┌──────────────────┐        ┌──────────────────┐
                │ Purified Bulk Lot│        │ Purified Bulk Lot│
                │     L0904009     │        │     L1405001     │
                └────────┬─────────┘        └────────┬─────────┘
                         ▼                           ▼
                ┌──────────────────┐        ┌──────────────────┐
                │   Final Vialed   │        │   Final Vialed   │
                │   Product Lot    │        │   Product Lot    │
                │     L0904010     │        │     L1402001     │
                └──────────────────┘        └──────────────────┘
```

FIG. 26

CERTIFICATE OF ANALYSIS
Page 1 of 1

Product Name: PVSRIPO Harvest Pool Project Number: 0576 Part Number: 50206

NSC Number: 719277 Production Date: Lot Number: L1311003 Lot Size: 10 bottles

Container Size/Fill Volume: 1L PTEG bottle/ ~700 mL Storage Temperature: ≤-70°C

Description: Bulk Harvest Pool of PVSRIPO virus from infected Vero cells, Lot #217002-2.

| Test Description | Assay Specification | Test SOP # or Study # | QC Test Request Number | Result |
|---|---|---|---|---|
| Potency | | | | |
| Virus Titer ($TCID_{50}$ Assay) | Report results | Texcell North America, Study #14-42-550-2 | QC-052605 | 9.33($log_{10}$) $TCID_{50}$/mL; Equivalent to $2.14 \times 10^9$ $TCID_{50}$/mL |
| Safety | | | | |
| Extended Bioburden | < 20 CFU/mL; no pathogenic organisms | BQC 22133 | QC-052553 | No growth (0 CFU/mL) |
| Detection of Mycoplasma (PTC) for Viral Products using Vero Cells | None detected | WuXi AppTec 30200 | QC-052604 | None detected |
| Detection of Mycoplasma (PTC) for Viral Products using NIH/3T3 Cells | None detected | WuXi AppTec 30200 | QC-054615 | None detected |
| Detection of Mycoplasma by TD-PCR | None detected | WuXi AppTec 30448 | QC-054616 | None detected; LoD ≤ 1 CFU |
| Endotoxin by LAL | Report results | BQC 22204 | QC-052594 | < 0.5 EU/mL |
| Virus Stability by rct40 | ≥ 5 log reduction in titer at 40°C from 36°C | Texcell North America, Study #14-44-562-2 | QC-052606 | > 7.93 log reduction in titer |
| *In vivo* Adventitious Agents | No viral contaminants detected | WuXi AppTec 30027 | QC-052603 | No viral contaminants detected |

FIG. 27

Certificate of Analysis
Page 1 of 2

| | | | | |
|---|---|---|---|---|
| Product Name: | PVSRIPO Purified Sterile Bulk | Project Number: 576 | | Part Number: 50211 |
| NSC Number: | 719277 | Production Date: | Lot Number: L1405001 | Lot Size: 1 PETG Bottle |
| Container Size/Fill Volume: | 2L / 1054 mL | | | Storage Temperature: ≤ -70°C |
| Description: | PVSRIPO purified sterile bulk in 50 mM sodium phosphate, 0.9% NaCl, pH 7.4, 0.2% HSA. Passage P2 on Vero Cell Lot #217002-2. | | | |

| Test Description | Assay Specification | Test SOP # or Study # | QC Test Request Number | Result |
|---|---|---|---|---|
| Identity | | | | |
| Full genome sequence | Homologous to PVSRIPO reference sequence[1] | American International Biotechnology, Inc., Study #LEIDOS-092314TB | QC-052193 | Homologous to PVSRIPO reference sequence[1] |
| Purity | | | | |
| Host Cell DNA (Vero) | Report results | American International Biotechnology, Inc., Study #LEIDOS-090114TB | QC-053186 | None detected; < 5 ng Vero DNA/mL |
| Residual Benzonase | Report results | WuXi AppTec 38067 | QC-053187 | 29 ng/mL |
| Total Protein by BCA[2] | Report results | BQC 22107 | QC-052800 | 158.8 µg/mL |
| Potency | | | | |
| Differential Killing | Report results | BQC 16116 | QC-053188 | No cell killing was detected in HEK293 cells with MOIs up to 10. Dose dependent inhibition of U87-MG cell proliferation observed |
| Virus Titer (TCID$_{50}$ Assay) | Report results | Texcell North America, Study #14-82-550-2 | QC-053192 | 7.94 x 10$^9$ TCID$_{50}$/mL |
| Safety | | | | |
| Sterility (Direct Inoculation) | No growth | WuXi AppTec 30744, (21 CFR 610.12) | QC-053189 | No growth |
| Bacteriostasis/Fungistasis (post-sterility) | Non-bacteriostatic/Non-Fungistatic | WuXi AppTec 30736, (21 CFR 610.12) | QC-053190 | Non-bacteriostatic/Non-Fungistatic |
| Endotoxin by LAL | ≤ 10 EU/mL | BQC 22204 | QC-053191 | < 0.5 EU/mL |

[1] PVSRIPO MVB Reference Standard Lot L0403006 (QC-022271)
[2] Sample taken prior to addition of HSA to Purified Bulk (Lot L1311004)

FIG. 28

CERTIFICATE OF ANALYSIS
Page 1 of 2

| Product Name: | PVSRIPO Final Vialed Product | | Project Number: 0576 | Part Number: 50217 |
|---|---|---|---|---|
| NSC Number: 719277 | Production Date: | | Lot Number: L1402001 | Lot Size: 1766 vials |
| Container Size/Fill Volume: | 2mL glass / 0.5mL | | | Storage Temperature: ≤-70°C |
| Description: | Vialed PVSRIPO virus in 50 mM sodium phosphate, 0.9% NaCl, pH 7.4, 0.2% HSA. Passage P2 on Vero Cell Lot #217002-2. | | | |

| Test Description | Assay Specification | Test SOP # or Study # | QC Test Request Number | Result |
|---|---|---|---|---|
| Appearance | | | | |
| Clarity, Color, and Appearance | Clear to translucent, colorless liquid with no evidence of particulate matter | BQC 22925 | QC-053194 | Clear to translucent, colorless liquid with no evidence of particulate matter |
| Identity | | | | |
| Full genome sequence | Homologous to PVSRIPO reference sequence[1] | American International Biotechnology, Inc., Study #LEIDOS-092314TB | QC-053193 | Homologous to PVSRIPO reference sequence[1] |
| RT-qPCR (HRV-2 IRES and Polio Polyprotein) | Positive for HRV-2 IRES and Polio Polyprotein sequences; Report viral copy number | American International Biotechnology, Inc., Study #LEIDOS-080114TB | QC-053195 | Positive for HRV-2 IRES and Polio Polyprotein sequences; $1.58 \times 10^{12}$ viral copies/mL |
| Content | | | | |
| Virus Titer ($TCID_{50}$ Assay) | Report results | Texcell North America, Study #14-81-550-2 | QC-053192 | $4.48 \times 10^{9}$ $TCID_{50}$/mL |
| Safety | | | | |
| pH | 7.4 ± 0.5 | BQC 22124 | QC-053196 | 7.2 |
| Sterility (Direct inoculation) | No growth | WuXi AppTec 30744, (21 CFR 610.12) | QC-053197 | No growth |
| Polio virus IRES (RT-qPCR) | None Detected | American International Biotechnology, Inc., Study #LEIDOS-080114TB | QC-053198 | None Detected; < 100 wild-type Polio genomic copies per $2.6 \times 10^{7}$ copies of PVSRIPO |
| Virus Stability by rct40 | ≥ 5 log reduction in titer at 40°C from 36°C | Texcell North America, Study #14-85-562-2 | QC-053199 | > 7.09 log reduction in titer at 40°C from 36°C |
| Endotoxin by LAL | ≤ 10 EU/mL | BQC 22204 | QC-053191 | < 0.5 EU/mL |
| For Information Only | | | | |
| Virus Particle by EM | Report results | Texcell North America, Study #14-80-521.5-2; FNLCR Electron Microscopy Laboratory | QC-053200 | $7.0 \times 10^{10}$ vp/mL |
| Ratio VP/$TCID_{50}$ | Report results | Calculation | N/A | 15.6 |

PROCESSES FOR PRODUCTION AND PURIFICATION OF NUCLEIC ACID-CONTAINING COMPOSITIONS

CROSS-REFERENCE TO RELATED APPLICATION

This is the U.S. National Stage of International Application No. PCT/US2016/036888, filed Jun. 10, 2016, which was published in English under PCT Article 21(2), which in turn claims the benefit of U.S. Provisional Application No. 62/173,777, filed Jun. 10, 2015, herein incorporated by reference.

ACKNOWLEDGEMENT OF GOVERNMENT SUPPORT

This invention was made with Government support under contract number HHSN261200800001E awarded by the National Institutes of Health, National Cancer Institute. The Government has certain rights in the invention.

FIELD

Disclosed herein are processes for manufacturing nucleic acid-containing compositions, including high purity virus-based nucleic acid compositions, such as recombinant RNA-based viruses (for example, recombinant polioviruses) that can be used as anti-cancer agents or vaccines. Also provided are compositions generated using such methods.

BACKGROUND

Nucleic acid-based biopharmaceuticals are useful for protection from, or treatment of, a variety of diseases and conditions. For example, DNA-based vaccines can be employed as protective or therapeutic vaccines used in treatment or prevention of infectious diseases, recombinant retroviral vectors can be used for genetic therapy, and oncolytic viruses that selectively destroy tumor cells can be produced. Several types of viruses have been identified as potential oncolytic agents, for example, adenovirus, vaccinia virus and herpes simplex virus.

Poliovirus, which causes poliomyelitis in humans, is a small RNA virus of the family Picornaviridae. Modified attenuated forms of poliovirus are potentially useful as vehicles for delivery of nucleic acid sequences to the human brain, because poliovirus infects the central nervous system, possibly by crossing the blood-brain barrier and binding to CD155 receptors, as discussed in Gromeier et al. (*Virology* 2000 273(2):248-57). One potential application of modified attenuated forms of poliovirus is the production of therapeutic oncolytic compositions for treating brain malignancies, such as gliomas and medulloblastomas.

In the area of nucleic acid-based biopharmaceuticals, large amounts of highly purified nucleic acid material are required for clinical applications and the manufacture of clinical products, such as oncolytic viruses. Accordingly, there is a need for efficient production and purification processes of reduced complexity and reduced costs that will generate sufficient amounts of high purity nucleic acid material.

SUMMARY

Disclosed herein are processes or methods for producing a purified live virus (such as a recombinant poliovirus), which employs, separately or in combination, (i) an improved process for generating viral template plasmid and (ii) an improved process for purifying the live virus that includes rapid detection steps during or after column chromatography separation. The improved process for generating viral template plasmid (such as one that includes a DNA template for an RNA virus) addresses the problem of genetic instability of the plasmids containing the viral genome (e.g., of a recombinant polio virus) in host (e.g., bacterial) cells, in which the plasmids are typically propagated. For example, this process can be applied to production of viral DNA templates in bacterial cells when the problem of genetic instability of such templates exists. The improved viral purification process, which is shown herein to increase the yield and/or purity of the resulting product and decreases purification time, is generally applicable to purification of any nucleic acid molecule-containing composition, such as virus-based composition, and can be used for the purification of live native or recombinant viruses, such as those needed for clinical applications.

In one example, the improved process for producing viral template plasmid is a method of generating plasmid DNA (e.g., bacterial plasmid) containing a viral template sequence (e.g., a corresponding DNA sequence for an RNA virus, such as a recombinant poliovirus), which can be referred to as a "viral template plasmid" or more specifically a "recombinant poliovirus plasmid DNA template." The improved process includes transforming host cells (e.g., bacterial host cells) with the viral template plasmid (e.g., attenuated recombinant poliovirus plasmid DNA), growing the transformed cells on solid media, and selecting colonies containing the correct plasmid sequences (e.g., recombinant poliovirus plasmid DNA sequences). Host cells containing correct plasmid sequences (e.g., plasmid is not empty, recombination did not occur) are propagated in liquid culture, and the viral template plasmid (e.g., recombinant poliovirus plasmid DNA) extracted from the propagated host cells. The cell propagation and extraction steps are performed without freezing the material produced in the propagation step, which reduces the risk of plasmid genetic instability and resulting errors in the viral template sequence. In some examples, the extracted viral template plasmid is linearized and in vitro transcribed in order to generate infectious naked virus RNA, which is subsequently used to infect mammalian cells. The infected mammalian cells may be the amplified in culture in a multi-step process that can be referred to as "expansion," and grown to produce live virus, which is subsequently purified (for example using the disclosed improved methods).

The methods for generating an isolated plasmid DNA composition containing a plasmid including one or more viral template sequences can include introducing, for example by transformation, plasmid DNA which includes the viral template sequence(s) into one or more host cells (e.g., bacterial cells), thereby generating the one or more cells transformed with the isolated plasmid DNA. In some examples, the plasmid DNA introduced into the host cell is from a stock (e.g., from a cell bank). In other examples, the plasmid DNA introduced into the host cell is purified or isolated. The transformed cells are grown on solid phase culture, for example under selective conditions, thereby generating one or more colonies (e.g., bacterial colonies). One or more colonies are tested for the presence of one or more nucleic acid sequences from the one or more viral template sequences (e.g., to ensure the presence of the desired viral sequence in the plasmid). A liquid culture of host cells from the colony (or colonies) in which the presence of one or more nucleic acid sequences was detected is propagated, for example under fermentation conditions. The plasmid DNA including one or more viral template sequences from the propagated transformed cells is extracted or removed from the transformed cells, thereby producing the isolated plasmid DNA composition. In such methods, the transformed cells are not exposed to freezing conditions (e.g., temperatures at or below −20° C.) between the propagating and the extracting steps.

The disclosure also provides an improved process for purification of a nucleic acid-containing composition, such as a live virus, for example a live recombinant poliovirus. Such methods can be used to obtain purified nucleic acid molecule-containing compositions, such as a virus. This improved processes, wholly or in part, can be applied to production and purification of a variety of nucleic acid-containing compositions, including, but not limited to, production and purification of attenuated and non-live virus-based nucleic acid compositions and plasmid DNA purification. The process includes two column chromatography separation steps (size separation followed by anion exchange) and detection of the target nucleic acid (e.g., live recombinant poliovirus) in column chromatography fractions by a rapid detection process, such as quantitative polymerase chain reaction (qPCR). Rapid detection of the a specific sequence of the target nucleic acid in chromatography fractions enhances overall purification consistency and robustness and reduces the number of chromatography steps employed, thus reducing its complexity and costs. Rapid detection also reduces overall purification time, and improves the yields and/or purity of the target nucleic acid (e.g., live recombinant poliovirus). Thus, the exemplary purification process is rapid, efficient and leads to unexpectedly improved yields and/or purity of the target nucleic acid molecule (e.g., live recombinant poliovirus).

In a specific example, a process is provided for generating virus host cells infected with a non-naturally occurring RNA-based virus (e.g., non-naturally occurring poliovirus). Such methods can include introducing a plasmid DNA (e.g., of a bacterial plasmid) containing a template sequence of the non-naturally occurring RNA-based virus into one or more host cells (e.g., bacterial cells), thereby generating host cells transformed with the plasmid DNA. In some examples, the plasmid DNA introduced into the host cell is from a stock (e.g., from a cell bank). In other examples, the isolated plasmid DNA introduced into the host cell is purified or isolated. The transformed cells are grown in a solid phase culture, for example under selective conditions, thereby generating one or more colonies (e.g., bacterial colonies). One or more colonies are tested for the presence of one or more nucleic acid sequences from the non-naturally occurring RNA-based virus (e.g., to ensure the presence of the desired viral sequence in the plasmid). A liquid culture of host cells from the colony (or colonies) in which the presence of one or more nucleic acid sequences from the non-naturally occurring RNA-based virus was detected is propagated, for example under fermentation conditions. The plasmid DNA including the template sequence of the non-naturally occurring RNA-based virus from the propagated transformed cells is extracted from the transformed cells. Naked RNA of the non-naturally occurring RNA-based virus is optionally generated by in vitro translation of the template sequence. The resulting naked RNA of the non-naturally occurring RNA-based virus is introduced into virus host cells (e.g., mammalian host cells), thereby generating the virus host cells infected with the non-naturally occurring RNA-based virus. Such methods do not include exposing the transformed cells to freezing conditions (e.g., temperatures at or below −20° C.) between the propagating and the extracting steps.

The process of producing a purified nucleic acid composition, such as a virus-containing composition, can include separating a solution containing the nucleic acid composition on a chromatography column (such as a size separation column) and then detecting at least one nucleic acid sequence present in the nucleic acid in one or more fractions eluted from the chromatography column (for example using qPCR) and then pooling the one or more fractions in which the at least one nucleic acid sequence is detected to be present in a quantity above a threshold value.

In one embodiment, a process is provided for purifying a live non-naturally occurring poliovirus by culturing mammalian host cells infected with the poliovirus in one or more rounds of cell culture to produce a liquid cell culture medium containing the poliovirus; separating the liquid cell culture medium from the mammalian host cells, debris of the mammalian host cells or both, thereby generating a supernatant containing the poliovirus; separating the supernatant containing the poliovirus on a chromatography column; detecting the poliovirus present in one or more fractions eluted from the chromatography column by detecting nucleic acid sequences found in the poliovirus; and pooling those fractions in which the nucleic acid sequences are detected in an amount above a threshold value.

In another embodiment, a process is provided for obtaining a purified live non-naturally occurring RNA-based virus by providing stock isolated plasmid DNA of a bacterial plasmid containing a template sequence of the non-naturally occurring RNA-based virus; introducing the stock isolated plasmid DNA into one or more bacterial cells, thereby generating bacterial cells transformed with the stock isolated plasmid DNA; growing a solid phase culture of the one or more bacterial cells transformed with the stock isolated plasmid DNA, thereby generating one or more bacterial colonies; detecting the presence of one or more nucleic acid sequences from the template sequence of the RNA-based virus in at least one of the bacterial colonies; propagating a culture of bacterial cells from the bacterial colony in which the presence of one or more nucleic acid sequences was detected, wherein the bacterial cells are not frozen between the propagating and the extracting steps; extracting the plasmid DNA containing the template sequence of the RNA-based virus from the propagated bacterial cells; generating naked RNA of the RNA-based virus by in vitro translation of the template sequence; and introducing the naked RNA of the RNA-based virus into virus host cells, thereby generating virus host cells infected with the RNA-based virus; culturing virus host cells infected with the RNA-based virus in one or more rounds of cell culture to produce a liquid cell culture medium containing the RNA-based virus; separating the liquid cell culture medium from the mammalian host cells, debris of the mammalian host cells or both, thereby generating a supernatant containing the RNA-based virus; separating the supernatant containing the live non-naturally occurring RNA-based virus on a chromatography column (e.g., size separation column); detecting the live RNA-based virus present in one or more fractions eluted from the chromatography column by detecting one or more nucleic acid sequences found in the RNA-based virus (e.g., using qPCR); and pooling those fractions in which the nucleic acid sequences are present in an amount above a threshold value. The method can further include applying the pooled fractions for an anion exchange chromatography column, and concentrating the positive flow-through eluate.

In one example, the purification process for obtaining a composition that includes a live non-naturally occurring poliovirus includes separating an aqueous fluid containing the live non-naturally occurring poliovirus on a size separation chromatography column, detecting by quantitative polymerase chain reaction (qPCR) one or more nucleic acid sequences found in the live non-naturally occurring poliovirus, collecting and pooling at least one positive fraction of the eluate from said size separation column that contain the one or more nucleic acid sequences found in the live non-naturally occurring poliovirus, and separating the pooled positive fractions on an anion exchange chromatography column. The live non-naturally occurring poliovirus is collected in at least one positive fraction of the eluate from the anion exchange chromatography column. In some examples, this purification process does not contain any further chromatography separation steps after the anion exchange chromatography separation step. Thus, in some examples, the method only has two chromatography separation steps. The purification process can further include concentrating by diafiltration the live non-naturally occurring poliovirus eluted in the flow-through eluate. In some examples, the purification process can be conducted in less than 8 hours, such as 4-8 hours. In some embodiments, the yield of the purification process is ≥50%, such as at least 55%, at least 60%, at least 65%, at least 70%, at least 75%, at least 80%, or at least 83%, such as 50-60%, 50-80%, 60-80%, 70-85%, or 50-85%. Yield of the live non-naturally occurring poliovirus from the at least one positive fraction of the eluate from the anion exchange chromatography column can be ≥50%.

The aqueous fluid containing the live virus (such as a live non-naturally occurring poliovirus) can be a liquid cell culture medium obtained by a process that includes culturing, in a one or more rounds of cell culture, virus host cells infected with the virus. The liquid cell culture medium can be obtained by, after culturing, separating the liquid cell culture medium from the virus host cells, debris of the virus host cells or both. The cell culture medium can be obtained by incubating the liquid cell culture medium with a nuclease enzyme capable of digesting free nucleic acids in solution but not encapsulated viral nucleic acids. The virus host cells infected with the virus can be obtained by a process comprising: providing stock isolated plasmid DNA of a bacterial plasmid comprising a template sequence of the virus; introducing the stock isolated plasmid DNA into one or more bacterial cells, thereby generating the one or more bacterial cells transformed with the stock isolated plasmid DNA; growing a solid phase culture of the one or more transformed bacterial cells, thereby generating one or more bacterial colonies; detecting the presence of one or more nucleic acid sequences from the template sequence of virus in at least one of the one or more bacterial colonies; propagating a culture of bacterial cells from the at least one bacterial colony in which the presence of one or more nucleic acid sequence was detected; extracting the plasmid DNA comprising the template sequence of the virus from the propagated bacterial cells, wherein the bacterial cells are not frozen between the propagating and the extracting steps; generating naked RNA of the virus (e.g., of the non-naturally occurring poliovirus) by in vitro translation of the template sequence; and introducing the naked RNA of the virus into virus host cells, thereby generating virus host cells infected with the virus. The bacterial plasmid can be a plasmid having an *E. coli* origin of replication, and wherein the one or more bacterial cells are *E. coli* cells. The virus host cells can be mammalian host cells, such as Vero cells.

The viruses purified using the disclosed methods can be an RNA virus or a DNA virus, such as a single stranded DNA virus. In one example, the virus is a native or non-naturally occurring polio virus, such as a Sabin virus or an oncolytic poliovirus, for example PVS-RIPO.

Also provided are compositions and kits containing purified viruses (or other analyte) generated using the disclosed methods.

The foregoing and other objects and features of the disclosure will become more apparent from the following detailed description, which proceeds with reference to the accompanying figures.

BRIEF DESCRIPTION OF THE DRAWINGS

FIG. 1A shows a digital image of the electrophoretic separation (ethidium bromide-stained agarose gel) results of pUC19-based *E. coli* plasmid vector constructs isolated from a liquid culture of *E. coli* grown from frozen *E. coli* stock transformed with template plasmid DNA for the recombinant oncolytic poliovirus PVS-RIPO. The schematic drawing illustrates the correct and incorrect vector sequences isolated from the culture (1—vector with transposon insertion in the PVS-RIPO sequence; 2—correct vector sequence (("PVSRIPO_kan"); 3—pUC19 dimer without viral template sequence; 4—"empty" pUC19 vector without a viral template sequence).

FIG. 1B is a digital image showing an expanded version of the gel of FIG. 1A and is an agarose gel analysis of PVS-RIPO plasmid production lot L0311005 (right hand lanes 6-8) containing integrated Transposon IS10R compared to the correct vector sequence in the PVS-RIPO accession bank control lot L0305006 (left hand lanes 2-4). Note the shift in the central band's size due to transposon integration in lane 7 (test) to lane 3 (control), also note the increase in molecular weight of the linearized plasmid in lane 8 compared to lane 4. Lanes 1, 5 and 9 are 1 Kb plus DNA molecular weight marker (Invitrogen Inc.) where the top marker band is approximately 12 Kbp in size. Lanes 2 and 6 are uncut supercoiled and open circle PVS-RIPO forms, lanes 3 and 7 are Mun I cut plasmid, and lanes 4 and 8 are Sal I cut linearized plasmid.

FIG. 2 shows a schematic comparison between the disclosed improved process for producing viral template plasmid (for example for PVS-RIPO) (left) and a previously used procedure (right).

FIG. 3 shows a schematic illustration of the improved process for producing template plasmid DNA for PVS-RIPO.

FIG. 4 is a digital image showing the agar electrophoretic separation of two lots (Lot 1 and Lot 2) of template plasmid DNA for PVS-RIPO produced by the disclosed improved process. The reference is plasmid DNA from ACB lot L0305006. The two test samples are two separate flasks of PVSRIPO development lot L0401014, which did not exhibit plasmid instability.

FIG. 5 is a schematic illustration of the improved purification process of virus (e.g., PVS-RIPO) from host cell culture medium containing the virus.

FIG. 6 shows the size-separation chromatography employed in the improved purification process of PVS-RIPO virus from Vero cell culture medium. The graph illustrates the comparison of continuous optical detection of nucleic acid in Sepharose 6FF chromatography fractions by measuring absorbance at 254 nm (top line) and detection of PVS-RIPO sequence by RT-qPCR (bottom line). The table shows the amounts of PVS-RIPO detected in chromatography fractions.

FIG. 10 is the Certificate of Analysis for *E. coli* DH5α Master Cell Bank Lot L0301014.

FIG. 11 is the Certificate of Analysis for *E. coli* DH5α Working Cell Bank Lot L0303011.

FIG. 12 is the Certificate of Analysis for PVSRIPO Plasmid DNA Lot L0401014.

FIG. 13 is a flow chart showing the PVSRIPO Initial Virus Seed Lot L0402026 (P0) manufacturing summary.

FIG. 14 is the Certificate of Analysis for Vero MCB Lot 2003-0049.

FIG. 15 is the Certificate of Analysis for Vero Working Cell Bank, Lot 217002-2.

FIG. 17 is the Certificate of Analysis for PVSRIPO Master Virus Seed Lot L0403006.

FIG. 19 is a Certificate of Analysis for PVSRIPO Harvest Pool Lot L0904008.

FIG. 20 is a Certificate of Analysis for PVSRIPO Purified Sterile Bulk Lot L0904009.

FIG. 21 is a Certificate of Analysis for PVSRIPO Final Vialed Product Lot L0904010.

FIG. 22 is a Certificate of Analysis for PVSRIPO Toxicology Lot L0603006.

FIG. 23 is a lot history of PVSRIPO manufactured.

FIG. 26 is a Certificate of Analysis for PVSRIPO Harvest Pool Lot L1311003.

FIG. 27 is a Certificate of Analysis for PVSRIPO Purified Sterile Bulk Lot L1405001.

FIG. 28 is a Certificate of Analysis for PVSRIPO Final Vialed Product Lot L1402001.

SEQUENCE LISTING

Figure 1A:
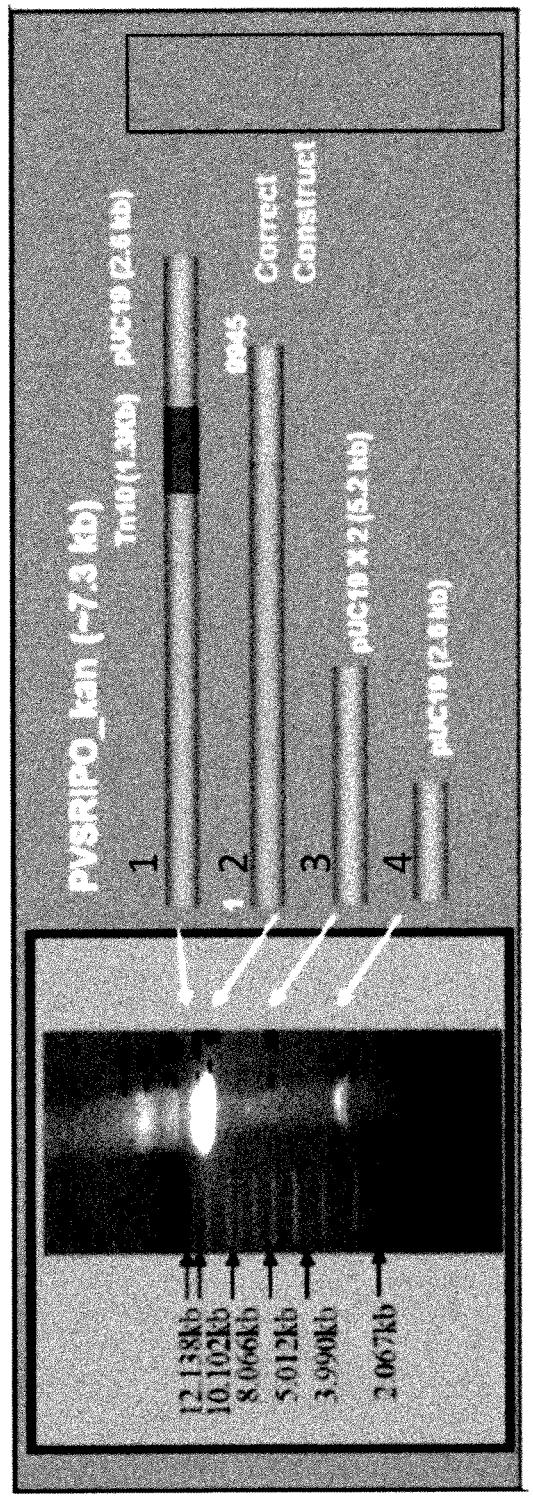

The nucleic and amino acid sequences are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The sequence listing generated on Nov. 6, 2017 (3.12 kb) and submitted herewith is herein incorporated by reference.

SEQ ID NOS: 1-13 are nucleic acid primer and probe sequences used in real time RT-PCR assays.

DETAILED DESCRIPTION

Unless otherwise noted, technical terms are used according to conventional usage. Definitions of common terms in molecular biology can be found in Benjamin Lewin, Genes VII, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnology: a Comprehensive Desk Reference*, published by VCH Publishers, Inc., 1995; and other similar references.

As used herein, the singular forms "a," "an," and "the," refer to both the singular as well as plural, unless the context clearly indicates otherwise. As used herein, the term "comprises" means "includes." Thus, "comprising a nucleic acid molecule" means "including a nucleic acid molecule" without excluding other elements. It is further to be understood that any and all base sizes given for nucleic acids are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting. All references, including patent applications and patents, and sequences associated with the GenBank® Accession Numbers listed (as of Jun. 10, 2016) are herein incorporated by reference.

In order to facilitate review of the various embodiments of the disclosure, the following explanations of specific terms are provided:

Adjuvant: A compound, composition, or substance that when used in combination with an immunogenic agent (such as a virus purified using the disclosed methods) augments or otherwise alters or modifies a resultant immune response. In some examples, an adjuvant increases the titer of antibodies induced in a subject by the immunogenic agent. In another example, if the antigenic agent is a multivalent antigenic agent, an adjuvant alters the particular epitopic sequences that are specifically bound by antibodies induced in a subject.

Exemplary adjuvants include, but are not limited to, Freund's Incomplete Adjuvant (IFA), Freund's complete adjuvant, B30-MDP, LA-15-PH, montanide, saponin, aluminum salts such as aluminum hydroxide (Amphogel, Wyeth Laboratories, Madison, N.J.), alum, lipids, keyhole lympet protein, hemocyanin, the MF59 microemulsion, a mycobacterial antigen, vitamin E, non-ionic block polymers, muramyl dipeptides, polyanions, amphipatic substances, ISCOMs (immune stimulating complexes, such as those disclosed in European Patent EP 109942), vegetable oil, Carbopol, aluminium oxide, oil-emulsions (such as Bayol F or Marcol 52), *E. coli* heat-labile toxin (LT), Cholera toxin (CT), and combinations thereof.

In one example, an adjuvant includes a DNA motif that stimulates immune activation, for example the innate immune response or the adaptive immune response by T-cells, B-cells, monocytes, dendritic cells, and natural killer cells. Specific, non-limiting examples of a DNA motif that stimulates immune activation include CG oligodeoxynucleotides, as described in U.S. Pat. Nos. 6,194,388; 6,207,646; 6,214,806; 6,218,371; 6,239,116; 6,339,068; 6,406,705; and 6,429,199, and IL-2 or other immunomodulators.

Administration: To provide or give a subject an agent, such as a virus purified using the disclosed methods, by any effective route. Exemplary routes of administration include, but are not limited to, injection (such as subcutaneous, intramuscular, intradermal, intraperitoneal, intratumoral, and intravenous), oral, transdermal, intranasal, and inhalation routes.

Attenuated pathogen: A pathogen with a decreased or weakened ability to produce disease while one the ability to stimulate an immune response like that of the natural pathogen. In another example, a pathogen is attenuated by selecting for avirulent variants under certain growth conditions (for example see Sabin and Boulger. *J. Biol. Stand.* 1:115-8; 1973; Sutter et al., 2003. Poliovirus vaccine—live, p. 651-705. In S. A. Plotkin and W. A. Orenstein (ed.), Vaccines, Fourth ed. W.B. Saunders Company, Philadelphia). An exemplary attenuated pathogen is the Sabin polio virus.

Contact: Placement in direct physical association, including a solid or a liquid form. Contacting can occur in vitro or ex vivo, for example, by adding a reagent to a sample (such as one containing bacterial cells expressing a viral template plasmid), or in vivo by administering to a subject (such as administration of a virus purified using the disclosed methods).

Effective amount: The amount of an agent (such as a virus purified using the disclosed methods) that is sufficient to effect beneficial or desired results, such as a protective immune response, such as an anti-cancer response.

A therapeutically effective amount may vary depending upon one or more of: the subject and disease condition being treated, the weight and age of the subject, the severity of the disease condition, the manner of administration and the like, which can readily be determined by one of ordinary skill in the art. The beneficial therapeutic effect can include enablement of diagnostic determinations; amelioration of a disease, symptom, disorder, or pathological condition; reducing or preventing the onset of a disease, symptom, disorder or condition; and generally counteracting a disease, symptom, disorder or pathological condition. In one embodiment, an "effective amount" (e.g., of virus purified using the disclosed methods) is an amount sufficient to reduce the volume/size of a tumor (such as a glioblastoma), the weight of a tumor, the number of metastases, reduce the volume/size of a metastasis, the weight of a metastasis, or combinations thereof, for example by at least 10%, at least 20%, at least 25%, at least 50%, at least 70%, at least 75%, at least 80%, at least 90%, at least 95%, or at least 99% (as compared to no administration of the therapeutic agent). In one embodiment, an "effective amount" (e.g., of a virus purified using the disclosed methods) is an amount sufficient to increase the immune response in vivo, for example increase production of antibodies specific for the immunogen by at least 10%, at least 20%, at least 25%, at least 50%, at least 70%, at least 75%, at least 80%, at least 90%, at least 95%, at least 99%, at least 100%, at least 200%, at least 300%, at least 400%, at least 500%, or at least 600% (as compared to no administration of the therapeutic agent).

Host cells: Cells in which a vector can be propagated and its nucleic acids expressed. The cell may be prokaryotic or eukaryotic. The term also includes any progeny of the subject host cell. Thus, host cells can be transgenic, in that they include nucleic acid molecules that have been introduced into the cell, such as a viral template plasmid nucleic acid molecule. In one example, the host cell is a cell (such as a mammalian cell) which a virus (such as PVS-RIPO) proliferates. Proliferation of the virus in host cells can be used for production of the viral material (for example, Vero cells used for production of PVS-RIPO), or, in some cases, for protein expression. For example, recombinant baculoviruses can be used for recombinant protein expression in insect cells ("baculovirus expression system"). Viral proliferation can occur in vitro, for example, in cell culture, or in vivo, when viral host cells are a part of an organism.

Immune response: A response of a cell of the immune system, such as a B-cell, T-cell, macrophage, monocyte, or polymorphonucleocyte, to an immunogenic agent (such as a virus purified using the disclosed methods) in a subject. An immune response can include any cell of the body involved in a host defense response, such as an epithelial cell that secretes interferon or a cytokine. An immune response includes, but is not limited to, an innate immune response or inflammation.

The response can be specific for a particular antigen (an "antigen-specific response"). In a particular example, an immune response is a T cell response, such as a CD4+ response or a CD8+ response. In another example, the response is a B cell response, and results in the production of specific antibodies to the immunogenic agent.

In some examples, such an immune response provides protection for the subject from the immunogenic agent or the source of the immunogenic agent. For example, the response can protect a subject, such as a human or veterinary subject, from infection by a pathogen, or interfere with the progression of an infection by a pathogen. An immune response can be active and involve stimulation of the subject's immune system, or be a response that results from passively acquired immunity.

Increase or Decrease: A statistically significant positive or negative change, respectively, in quantity from a control value (such as a value representing no therapeutic agent). An increase is a positive change, such as an increase at least 50%, at least 100%, at least 200%, at least 300%, at least 400% or at least 500% as compared to the control value. A decrease is a negative change, such as a decrease of at least 20%, at least 25%, at least 50%, at least 75%, at least 80%, at least 90%, at least 95%, at least 98%, at least 99%, or at least 100% decrease as compared to a control value. In some examples the decrease is less than 100%, such as a decrease of no more than 90%, no more than 95%, or no more than 99%.

Isolated: An "isolated" biological component (such as a virus purified using the disclosed methods) has been substantially separated, produced apart from, or purified away from other biological components in the cell or media in which the component occurs, such as other nucleic acid molecules and proteins (e.g., host cell chromosomal and extrachromosomal DNA and RNA, and proteins). Isolated viruses purified using the disclosed methods, or viral template plasmids expanded using the disclosed methods in some examples are at least 50% pure, such as at least 75%, at least 80%, at least 90%, at least 95%, at least 98%, at least 99%, at least 99.9999%, or at least 100% pure, for example, as measured by residual host cell (HC) DNA. In some examples, isolated viruses purified using the disclosed methods, or viral template plasmids expanded using the disclosed methods have less purity when measured by residual HC protein (HCP), such as at least 3% pure, at least 4% pure, or at least 5% pure (such as 3-4% pure), for example when an increase in total PFU is desired. Even at ~3% protein purity the level of HCP is within acceptable limits for a therapeutic product. In some examples, isolated viruses purified using the disclosed methods, or viral template plasmids expanded using the disclosed methods, when measured by residual HCP, are at least 50% pure, such as at least 75%, at least 80%, at least 90%, at least 95%, at least 98%, at least 99%, or at least 99.9999% pure.

Pharmaceutically acceptable carriers: The pharmaceutically acceptable carriers useful in this invention are conventional. *Remington's Pharmaceutical Sciences*, by E. W. Martin, Mack Publishing Co., Easton, Pa., 15th Edition (1975), describes compositions and formulations suitable for pharmaceutical delivery of a virus purified using the disclosed methods.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Poliovirus (PV): An enterovirus of the Picornaviridae family that is the causative agent of poliomyelitis (polio). Poliovirus has three serotypes. Exemplary polio sequences are provided in Toyoda et al., *J. Mol. Biol.* 174:561-85, 1984.

Non-natural forms of the polio virus include the recombinant oncolytic poliovirus PVS-RIPO and the attenuated Sabin oral polio vaccine (OPV), and can be generated using the disclosed methods. PVS-RIPO is a recombinant, live attenuated, nonpathogenic oncolytic virus containing the oral poliovirus Sabin type 1 in which the internal ribosomal entry site (IRES) is replaced with the IRES from human rhinovirus type 2 (HRV2), with potential antineoplastic activity (see for example Brown et al., Cancer 120:3277-86, 2014 and Goetz et al., *Cytokine Growth Factor Rev.* 2010 21(2-3):197-20). The OPV includes 57 nucleotide substitutions which distinguish the attenuated Sabin 1 strain from its virulent parent (the Mahoney serotype), two nucleotide substitutions attenuate the Sabin 2 strain, and 10 substitutions are involved in attenuating the Sabin 3 strain.

The primary attenuating factor common to all three Sabin vaccines is a mutation located in the virus's internal ribosome entry site (IRES) which alters stem-loop structures, and reduces the ability of poliovirus to translate its RNA template within the host cell. Exemplary Sabin sequences are provided in GenBank® Accession Nos. E01572.1, E01571.1 and E01570.1, as well as Nomoto et al., *Proc Natl Acad Sci USA.* 79(19): 5793-5797, 1982.

Another form of the PV is the chemically inactivated polio vaccine (IPV) developed by Dr Jonas Salk. This is based on three virulent strains Mahoney (type 1 poliovirus), MEF-1 (type 2 poliovirus), and Saukett (type 3 poliovirus). Such PV strains can be generated using the disclosed methods.

Purified: The term purified does not require absolute purity; rather, it is intended as a relative term. Thus, for example, a purified virus preparation generated using the disclosed methods is one in which the virus is more enriched than the virus is in a host cell or host cell extract. In one example, a preparation is purified such that the purified virus represents at least 50% of the total nucleic acid content of the preparation. In other examples, a virus is purified to represent at least 60%, at least 75%, at least 80%, at least 85%, at least 90%, at least 95%, at least 98%, or even at least 99%, of all macromolecular species present in a purified preparation prior to admixture with other formulation ingredients, such as a pharmaceutical carrier, excipient, buffer, absorption enhancing agent, stabilizer, preservative, adjuvant or other co-ingredient. In some examples, the purified preparation is be essentially homogeneous, wherein other macromolecular species are not detectable by conventional techniques. Such purified preparations can include materials in covalent association with the active agent, such as materials admixed or conjugated with the active agent, which may be desired to yield a modified derivative or analog of the active agent or produce a combinatorial therapeutic formulation or conjugate.

Recombinant: A recombinant nucleic acid molecule is one that has a sequence that is not naturally occurring or has a sequence that is made by an artificial combination of two otherwise separated segments of sequence. This artificial combination can be accomplished using routine methods, such as by chemical synthesis or by the artificial manipulation of isolated segments of nucleic acids, for example, by genetic engineering techniques such as those described in Sambrook et al. (ed.), Molecular Cloning: A Laboratory Manual, 2nd ed., vol. 1-3, Cold Spring Harbor Laboratory Press, Cold Spring Harbor, N.Y., 1989. The term recombinant includes nucleic acid molecules that have been altered solely by addition, substitution, or deletion of a portion of the nucleic acid molecule. Similarly, a recombinant protein is one encoded by a recombinant nucleic acid molecule. A recombinant virus includes one whose genes have been constructed and/or placed in an unnatural environment, for example for expression, for example using recombinant engineering techniques.

Subject: A vertebrate, such as a mammal, for example a human. Mammals include, but are not limited to, murines, simians, humans, farm animals, sport animals, and pets. In one embodiment, the subject is a non-human mammalian subject, such as a monkey or other non-human primate, mouse, rat, rabbit, pig, goat, sheep, dog, cat, horse, or cow. In some examples, the subject has a tumor, such as a glioblastoma, that can be treated using the polio virus generated using the disclosed methods. In some examples, the subject is a laboratory animal/organism, such as a mouse, rabbit, or rat.

Transform or Transfect: A virus or vector "transforms" or "transduces" a host cell when it transfers nucleic acid into the host cell. A cell is "transformed" or "transfected" by a nucleic acid transduced into the cell when the DNA becomes stably replicated by the cell, either by incorporation of the nucleic acid into the cellular genome, or by episomal replication.

Numerous methods of transfection are known to those skilled in the art, such as: chemical methods (e.g., calcium-phosphate transfection), physical methods (e.g., electroporation, microinjection, particle bombardment), fusion (e.g., liposomes), receptor-mediated endocytosis (e.g., DNA-protein complexes, viral envelope/capsid-DNA complexes) and by biological infection by viruses such as recombinant viruses (Wolff, J. A., ed, Gene Therapeutics, Birkhauser, Boston, USA 1994). In the case of infection by retroviruses, the infecting retrovirus particles are absorbed by the target cells, resulting in reverse transcription of the retroviral RNA genome and integration of the resulting provirus into the cellular DNA.

Transgene: An exogenous gene supplied by a vector. In one example, a transgene includes a viral template sequence, such as viral DNA template sequence for an RNA virus, such as polio (a natural polio virus or a non-naturally occurring polio virus).

Treating, Treatment, and Therapy: Any success or indicia of success in the attenuation or amelioration of an injury, pathology or condition, including any objective or subjective parameter such as abatement, remission, diminishing of symptoms or making the condition more tolerable to the patient, slowing in the rate of degeneration or decline, making the final point of degeneration less debilitating, improving a subject's physical or mental well-being, or prolonging the length of survival. The treatment may be assessed by objective or subjective parameters; including the results of a physical examination, blood and other clinical tests, and the like. In some examples, treatment with the disclosed methods results in a decrease in the number, volume, and/or weight of a tumor (e.g., a brain tumor) and/or metastases.

Under conditions sufficient for: A phrase that is used to describe any environment that permits a desired activity. In one example the desired activity is transformation of a host cell by a viral template plasmid, or growth of such a transformed host cell. In one example the desired activity is detection of target viral nucleic acid molecules, for example using qPCR. In one example the desired activity is treatment of a tumor and/or stimulation of an immune response in vivo, for example using a viruses purified using the disclosed methods.

Vaccine: An immunogenic composition that can be administered to an animal or a human to confer immunity, such as active immunity, to a disease or other pathological condition. Vaccines can be used prophylactically or therapeutically. Thus, vaccines can be used reduce the likelihood of infection or to reduce the severity of symptoms of a disease or condition or limit the progression of the disease or condition. In one example, a vaccine includes one or more viruses purified using the disclosed methods (e.g., a natural polio virus or a non-naturally occurring polio virus).

Vector: A nucleic acid molecule as introduced into a host cell, thereby producing a transformed host cell. A vector can include nucleic acid sequences that permit it to replicate in the host cell, such as an origin of replication. A vector can also include one or more therapeutic genes or selectable marker genes and other genetic elements known in the art. A vector can transduce, transform or infect a cell, thereby causing the cell to express nucleic acid molecules or proteins other than those native to the cell. A vector optionally includes materials to aid in achieving entry of the nucleic acid into the cell, such as a viral particle, liposome, protein coating or the like. In one example, a vector is a plasmid, such as a bacterial plasmid.

Nucleic Acid Molecule-Containing Compositions

The present disclosure provides improved processes or methods for the production and purification of compositions containing nucleic acid molecules, and are referred to here as methods or processes for production, isolation, purification or obtaining of nucleic acid molecule-containing compositions, formulations, materials and the like. Some examples provide improved processes for producing a nucleic acid DNA template (e.g., plasmid DNA template for a virus) for production of native or recombinant viruses. Other examples provide improved processes for purification of nucleic acid molecule-containing compositions generally, and improved processes for obtaining purified nucleic acid molecule-containing compositions. The term "nucleic acid molecule-containing compositions" and related terms encompass a variety of compositions and molecules containing polymeric nucleotides. Examples of nucleic acid molecule-containing compositions are compositions that contain DNA, RNA, DNA/RNA duplexes, viruses, plasmids, vectors and nucleoproteins. Nucleic acid molecule-containing compositions may contain naturally occurring nucleic acids or non-naturally occurring nucleic acids, which are also referred to as modified (by genetic modification or other processes, such as selection or chemical modification), artificial, artificially created, synthetic, genetically modified, genetically engineered, engineered, recombinant, recombinantly produced or by other related terms. Nucleic acid molecule-containing compositions include, but are not limited to, virus-based nucleic acid compositions, recombinant viruses, recombinant RNA-based viruses (for example, recombinant polioviruses), attenuated viruses, plasmids containing viral sequences, and viral DNA templates.

The disclosure provides improved processes for the production and purification of viruses, including naturally and non-naturally occurring viruses. Non-naturally occurring viruses may differ from naturally occurring viruses in varying degrees. Non-naturally occurring viruses can be derived from naturally occurring viruses artificially produced ("engineered"), for example, by recombinant techniques, in which case the non-naturally occurring viruses can be referred to as "recombinant." One example of non-naturally occurring viruses is pathogenic viruses that are modified, by genetic manipulation or other processes, such as selection or chemical modification, to reduce or destroy their pathogenicity. This process or, respectively, the resulting modified virus can be termed "attenuation," "attenuated" or by other related terms.

Non-naturally occurring viruses include, but are not limited to, viral vectors, oncolytic viruses and attenuated or recombinant viruses used as vaccines. Oncolytic viruses are viruses that are used to selectively infect and/or destroy, cancer cells. Viral vectors are viruses that are used to deliver genetic material into cells, either in vivo or in vitro (in cell culture) for various applications. For example, viral vectors can be used for genetic modification, gene therapy, for protein expression or as viral vaccines. Viral vaccines are used to deliver genetic material into cells or organisms with the goal of triggering protective or therapeutic immune response. For example, live attenuated viruses can be used as vaccines to trigger immune response against naturally occurring pathogenic versions of the same viruses (such as poliovirus, rubella virus, measles virus, etc.). The terms oncolytic viruses, viral vectors and viral vaccines sometimes overlap in meaning, but all of them can be artificially created, for example, by genetic modification of naturally occurring viruses using recombinant engineering techniques. Oncolytic viruses can be based on, but are not limited to, enterovirus, herpes virus (such as herpes simplex virus), vesicular stomatitis virus, poliovirus, reovirus, Seneca virus or vaccinia virus. Viral vectors include, but are not limited to, retroviral vectors, such as lentiviral vectors and vectors based on Moloney murine leukemia virus, adenoviral vectors and vectors based on adeno-associated viruses. Viral vaccines, include, but are not limited to, influenza vaccines, measles vaccine strains, mumps vaccine, rubella vaccine, varicella (chicken pox) vaccine, smallpox vaccine, human papilloma virus vaccines, HIV and HTLV vaccines, hemorrhagic fever vaccines or any live, attenuated or inactivated viral vaccine.

In one example, the non-naturally occurring virus produced and/or purified by the disclosed methods is recombinant poliovirus, such as an oncolytic attenuated recombinant poliovirus exemplified by PVS-RIPO. PVS-RIPO is an attenuated form of the Sabin Type I poliovirus created by exchanging the cognate internal ribosomal entry site (IRES) of poliovirus with its counterpart from human rhinovirus type 2 (HRV 2) to yield a poliovirus strain that does not replicate in normal neuronal cells, but which exhibits oncolytic activity against brain tumor cells. Upon intratumoral administration of recombinant oncolytic poliovirus PVS- RIPO, the poliovirus is selectively taken up by and replicates in tumor cells expressing CD155 (poliovirus receptor, PVR or NECL5) eventually causing tumor cell lysis. CD155, an oncofetal cell adhesion molecule and tumor antigen, is ectopically expressed in certain cancers, such as glioblastoma multiforme (GMB). Due to the heterologous HRV2 IRES in this recombinant virus, PVS-RIPO only propagates in susceptible, nonneuronal cells (e.g., GBM). PVS-RIPO and its properties and applications are described, for example, in Goetz et al., *Cytokine Growth Factor Rev.* 2010 21(2-3):197-20, Yang et al., *J. Virol. Methods.* 2009 155(1): 44-54, Cello et al., *J. Med. Virol.* 2008 80(2):352-9, and Dobrikova et al., *Molecular Therapy* 2008 16(11):1865-1872.

In one example, the non-naturally occurring virus produced and/or purified by the disclosed methods is the attenuated Sabin poliovirus (e.g., type 1, type 2 and/or type 3 poliovirus with the appropriate mutations). In one example, the virus produced and/or purified by the disclosed methods is one used in the inactivated polio vaccine (e.g., type 1, type 2 and/or type 3 poliovirus), which can be chemically inactivated (e.g., with formalin) following its production using the disclosed methods.

Comparison of Improved Viral Purification Methods and Prior Methods

Prior methods for producing and purifying of live PVS-RIPO is described, for example, in Ouellette et al., *BioProcessing J.* 2005 4(2):31-38 ("Ouelette et al."). The process described in Ouelette et al. involved preparation of PVS-RIPO plasmid DNA from bacterial cells transformed with PVS-RIPO plasmid stock, subsequent linearization of the plasmid DNA by restriction endonuclease, in vitro synthesis of viral RNA using T7 RNA polymerase, and electroporation of the viral RNA into Vero cells to generate the viral seed stock, which was used to produce PVS-RIPO virus in Vero cell culture. In the purification process described in Ouellette et al., PVS-RIPO virus was isolated from Vero cell culture supernatant, which was treated by Benzonase® enzyme and subjected to a sequence of four column chromatography separation steps. The first step was size-exclusion chromatography using Sepharose 4FF, with the column eluate monitored for UV absorbance at 280 nm and conductivity. The second step was anion-exchange column chromatography using Super Q 650M resin, which was virus non-binding (that is, the virus was collected in the flow-through). The third step was anion-exchange column chromatography using virus-binding CDM resin. The second and the third steps were performed in tandem, with the fractions eluted from the CDM column tested for presence of PVS-RIPO by SDS-PAGE, and selected and pooled for the following step based on the detected presence of PVS-RIPO. The fourth step was size exclusion chromatography using Sephadex G-25 resin, with the fractions tested, selected and pooled as in the previous step. The fourth step was included for additional PVS-RIPO purification and to remove the high salt buffer, in which PVS-RIPO was eluted from the CDM column, since poliovirus loses infectivity upon prolonged exposure to high salt.

Provided herein is an improved process for the purification of a virus. Exemplary viruses that can be generated and purified using these methods include, but are not limited to, DNA viruses (e.g., a single stranded DNA virus, such as those in one of the following families Anelloviridae, Bacillariodnaviridae, Bidnaviridae, Circoviridae, Geminiviridae, Inoviridae, Microviridae, Nanoviridae, Parvoviridae and Spiraviridae), RNA viruses (for example a Picrornavirus, such as an Aphthovirus (e.g., foot-and-mouth disease virus and bovine rhinitis virus), Aquamavirus, Avihepatovirus, Cardiovirus, Cosavirus, Dicipivirus, Enterovirus (e.g., any of enteroviruses A-J or rhinoviruses A-C), Erbovirus, Hepatovirus (e.g., hepatitis A), Kobuvirus, Megrivirus, Parechovirus (e.g., human parechovirus or Ljungan virus), Piscevirus, Salivirus, Sapelovirus, Senecavirus, Teschovirus, or Tremovirus; a Rhabdovirus (such as Rabies); a Paramyxovirus (such as measles virus, respiratory syncytial virus, and parainfluenza viruses); a Flavivirus (e.g., Dengue virus, Zika virus, West Nile virus, hepatitis C virus, and Japanese encephalitis virus), and Filoviridae (such as Ebola)), or a retrovirus such as HIV or HTLV. In one example, the virus generated and purified using these methods is a Group IV or Group VI virus, such as hepatitis C, hepatitis E, rhinovirus, or HIV.

In one example, the virus generated and purified using these methods is a naturally occurring poliovirus or a non-naturally occurring poliovirus (e.g., an oncolytic attenuated recombinant poliovirus exemplified by PVS-RIPO). In one example, the virus generated and purified using these methods is a poliovirus or a vaccine, such as a Sabin poliovirus or a native Salk virus (which can be chemically inactivated following purification).

The disclosed methods include a first chromatography separation step, which separates an aqueous fluid that contains the virus (e.g., live virus, such as a live non-naturally occurring poliovirus) on a size separation chromatography column, detecting one or more nucleic acid sequences found in the virus (e.g., live virus, such as a live non-naturally occurring poliovirus) in one or more fractions eluted from the size separation chromatography column by quantitative polymerase chain reaction (qPCR), pooling those fractions of the one or more fractions in which the one or more viral nucleic acid sequences is detected, thereby generating pooled fractions. qPCR and other rapid detection methods that can be employed are discussed herein and include methods known in the art.

The disclosed methods include a second, anion exchange, chromatography separation step. The second chromatography separation step further purifies positive pooled fractions from the first chromatography step. Thus, the pooled fractions obtained following the first chromatography step can be applied onto an anion exchange chromatography column. The resin used in the anion exchange chromatography column does not significantly bind to the virus, meaning that the virus (e.g., live virus, such as a live non-naturally occurring poliovirus) is eluted from the anion exchange chromatography column in a flow-through eluate, while contaminants are bound to the resin. Using virus non-binding resin and flow-through elution in this step, in contrast to a virus-binding resin, avoids exposure of the virus to a high salt elution buffer that would be required to elute the virus from a virus-binding resin. Exposure to high salt buffer can result in virus inactivation, while avoiding exposure to the high salt buffer improves the yield of the live virus. In one example, the disclosed improved purification process does not contain any additional chromatography separation steps after the anion exchange chromatography separation step. Thus, in a specific example, the improved purification process contains only (e.g., consists of) two chromatography separation steps (size separation and ion exchange with the virus eluted in the flow-through). In some examples, the improved purification process does not include a step that utilizes as virus-binding CDM resin. After the second chromatography separation step, the improved purification process can further include a concentrating step, for example, by diafiltration. This results in the elution of the virus (e.g., live virus, such as a live non-naturally occurring poliovirus) in the flow-through eluate.

In the improved purification process described herein, the aqueous fluid containing the virus (e.g., live virus, such as a live non-naturally occurring poliovirus) that is applied to the size separation column can be a liquid cell culture medium obtained by culturing, in a one or more rounds of cell culture, virus host cells infected with the virus (e.g., non-naturally occurring poliovirus). Virus host cells infected with the virus to be purified can be obtained by processes described herein. After culturing the virus host cells infected with the virus and prior to the first chromatography separation step, the cell culture medium containing the virus host cells infected with the virus can be separated from the virus host cells, debris of the virus host cells or both, for example by centrifugation or filtration. The liquid cell culture medium can also be treated with a nuclease enzyme capable of digesting free nucleic acids in solution but not encapsulated viral nucleic acids, such as Benzonase® enzyme. Other nucleases can be used, such as one or more DNases, one or more RNases, or mixtures of DNases and RNases. The nuclease treatment removes or substantially reduces free nucleic acids to improve safety, reduce harvest viscosity, and to improve the signal to noise ratio of viral detection methods used in the purification process, the detection methods discussed herein.

The improved purification process described herein possesses numerous differences in the steps involved, and the virus produced, when compared to previously described purification processes used to manufacture purified viruses on a large scale (e.g., non-naturally occurring poliovirus), such as the process described in Ouelette et al. For example, the improved purification process described herein provides one or more of improved virus yield, high reproducibility from run to run, reduced running time (that is, the improved process is faster than those previously known), and the ability to select for a desired compromise between product yields and purity (that is, greater process flexibility). Reduced running time of the improved process is due at least in part to the fact that the improved process contains fewer purification steps. The reduction in the number of the process steps also leads to a reduction in materials cost and decreases chance for viral degradation. Since the size of the column fractions collected after the first chromatography step can be finely adjusted (made larger or smaller) with rapid and specific fraction testing for the presence of the viral product (for example, by qPCR), by varying the fraction size and selecting which fractions are pooled for subsequent purification after the first chromatography step, the improved process can be adjusted to generate a more pure viral product, to generate a less pure viral product with an improved yield, or to readily select desired combination of yield and purity.

One difference between the new method and the old method of virus production is the number of steps, namely a reduction in the number of steps, including a reduced number of chromatography separation steps. For illustration only, Table 1 shows a side-by-side comparison of an exemplary embodiment of the improved purification process and of the process described in Ouelette et al. The process steps of the methods are listed in order from top to bottom in Table 1. Ouelette et al. contains four chromatography purification steps. In contrast, the improved purification process illustrated in Table 1 uses only two chromatography separation steps, namely the initial size separation chromatography step, followed by ion-exchange chromatography on a virus non-binding resin as the final chromatography step. These steps may be followed by a concentrating step. In contrast to Ouelette et al., the improved purification process does not include an anion-exchange CDM resin chromatography step ("CDM capture") nor a size separation chromatography on Sephadex G25 resin. Elimination of the CDM capture steps results in the improved yields of live virus in the improved purification process, since the virus is no longer in contact with high-salt buffer used for elution of the CDM resin column. Not using the CDM resin column also allows elimination of the final size separation step used in the Ouelette et al. process, because this final size separation step was needed to remove the high-salt buffer resulting from prior CDM capture step. In turn, omitting the CDM capture and the final size separation chromatography step eliminated the need to test the fractions eluted from these columns and selecting and pooling of the fractions based on the detected presence of the virus. Thus, the improved purification process described herein reduces the number of steps (for example, two-fold reduction in the number of chromatography separation steps), which leads to a more streamlined and less complex process. The reduction in the number of steps also leads to a reduction in the time required to perform the process. For example, the improved purification process can be performed, in some embodiments, in 8 hours or less, or less than 8 hours (such as 4 to 8 hours, 4 to 6 hours, 6 to 8 hours or 7 to 8 hours).

TABLE 1

Comparison of the improved purification process and of the process described in Ouelette et al.

| Improved process | Ouelette et al. process |
|---|---|
| Treatment of cell culture medium separated from cells and/or cell debris by a nuclease capable of digesting free nucleic acids in solution but not encapsulated viral nucleic acids (for example, Benzonase ® enzyme) | Treatment of cell culture medium separated from cells and/or cell debris by Benzonase ® enzyme |
| First chromatography separation - size separation ("gel filtration", "size exclusion") chromatography column (for example, Sepharose 6FF column) | First chromatography separation - size separation on a Sephrose 4FF column |
| Detection of specific viral sequences in the eluted fractions by qPCR | Detection of protein in the eluted fractions by monitoring absorbance at 280 nm |
| Pooling of at least some of the fractions in which viral sequences are detected by qPCR | Pooling of all or some of the fractions in which non-binding proteins and nucleic acids are detected by UV absorbance. |

TABLE 1-continued Comparison of the improved purification process and of the process described in Ouelette et al.

| Improved process | Ouelette et al. process |
|---|---|
| Second chromatography - anion exchange column (for example, Super Q), the virus eluting in a flow-through Concentration of the collected flow-through (for example, by diafiltration) | Second chromatography - anion-exchange column (Super Q 650M resin), the virus eluting in a flow-through Third chromatography (performed in tandem with the second chromatography step) - anion exchange column, virus-binding CDM resins Testing of the fractions eluted from the CDM column by SDS-PAGE Selecting and pooling of the fractions based on the detected presence of the virus Fourth chromatography - size separation chromatography, Sephadex G-25 column Testing of the fractions eluted from the CDM column by SDS-PAGE Selecting and pooling of the fractions based on the detected presence of the virus |

In addition, the disclosed method is different from that of Thomassen et al. (*Plos One,* 8:83374, 2013). For example, although Thomassen et al. use two chromatography steps, they do not incorporate an in-process real-time (PAT) analytical step to determine the exact location of the virus during Size Exclusion chromatography (such as real-time RT-PCR). Instead, they assume that the absorbance values on the column are solely due to the viral capsid proteins based on post-hoc SDS-PAGE results. However, the inventors have found that this is not necessarily the case (see FIG. 6 for example) and incorporate methods such as real-time RT-qPCR to identify the fractions containing the most virus prior to pooling. In addition, Thomassen et al. do not start with a viral plasmid template. Instead they start with a virus stock. As a result of these differences, the resulting virus generated is not as pure as those obtained with the disclosed methods.

The reduction in complexity of the improved purification process makes it suitable for large-scale manufacturing, for example generation of PVS-RIPO for clinical use. The term "large-scale manufacturing process" can refer to total amount of a live viral product produced by the process (process output). For live viral products, such as PVS-RIPO, process output is typically expressed in plaque forming units (PFUs) or tissue culture infections doses ($TCID_{50}$) units. In contrast output of inactivated virus material yields can be expressed in terms of mass and/or copy numbers.

Furthermore, the improved purification process eliminates the two chromatography separation steps that resulted in variable and poor yield of a live virus. It is unexpected that by eliminating these two chromatography separation steps, the improved purification process still achieved the purity of the purified non-naturally occurring poliovirus product that was comparable to the purity achieved by the process described in Ouelette et al. It was discovered that traditional chromatographic monitoring techniques, such as monitoring of UV absorbance at 254 or 280 nm (e.g., to detect nucleic acid molecules), made it necessary to use additional chromatography separation steps after the size separation chromatography followed by the flow-through elution of the virus from the second, anion exchange column. In the previously described purification processes, virus-positive size separation column chromatography fractions selected by monitoring UV absorbance at 254 or 280 nm resulted in collection of the fractions containing high levels of contaminating DNA, non-viral RNA, and proteins, since the contribution of the desired virus to the total absorbance of the eluate was relatively small. Thus, in the prior method, a large amount of the collected material was not relevant to the desired viral nucleic acid molecules (e.g., viral RNA for a polio virus). In addition, using the prior method, the resulting viral yield (e.g., in PFUs) recovered was highly variable and unpredictable (e.g., could be only a few % recovered, or up to about 50% recovery). This problem is solved by the disclosed methods which detect viral nucleic acids in the fractions eluted in the first chromatography step (size separation) by a quick and specific detection procedure, such as real time qPCR. Prior to this solution, the presence of the viral product in chromatography column fractions was not determined specifically, and electrophoresis, viral plaque assays and other specific assays had to be completed after the fractions were pooled in order to verify the presence of the virus in a product obtained after a particular purification step. For example, the process of Ouelette et al. (illustrated in Table 1) included two SDS-PAGE assay steps to detect the viral product. These assays employed in Ouelette et al. increased process duration and relayed information of limited value, since the size (volume) of the tested fractions was relatively large relative to the column size. In contrast, the use of a rapid and specific detection method in the process described herein to test chromatography fractions (such as qPCR, for example, real time RT-qPCR) allows one to rapidly test smaller volume fractions collected after the first chromatography step and permits the selection of fractions that contain high copy numbers of virus. Using a rapid and virus-specific detection technique, such as real time qPCR, makes it possible to rapidly determine and quantitate which size separation column fractions contained the highest titer virus, and to select such fractions for pooling and subsequent application on a virus non-binding ion exchange column. The resulting improved purification achieved after the first chromatography step results in improved live virus yields and reduced complexity and cost.

The improved process for production of purified virus (such as live non-naturally occurring poliovirus, such as an oncolytic attenuated recombinant poliovirus exemplified by PVS-RIPO) unexpectedly achieves increased yields of live infectious virus, when compared to previously known processes, such as the process described in Ouellette et al. Purification yield (also referred to as process yield) is calculated as the ratio between total plaque forming units (pfu) from the purified virus obtained after the last process step and those viruses harvested from host cell culture (e.g., the viruses in a mammalian cell, such as a Vero cell, that are used as the source of the virus to be purified). Alternatively, purification yield is based on copy number (via qPCR) or $TCID_{50}$. Purification yields achieved using the disclosed methods are consistently ≥50%, such as 50%-60% of the theoretical maximum, for example for PVS-RIPO. The theoretical maximum is 100% of pfu titer in the harvest is retained in the final purified 'bulk' drug substance (i.e., no loss of infectivity on a total pfu basis). Thus, the improved process unexpectedly leads to purification yield of live infectious virus of approximately ≥50%, for example a purification yield of at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, or at least 85%, for example a purification yield of 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 805, 81%, 82%, 83%, 84%, or 85%, such as a purification yield of 50%-60%, 50-80%, 50-83%, 50-85%, 60-83%, 60-85%, 70-83%, or 70-85%. In contrast, the process described in Ouellette et al., results in an overall yield of live, infectious virus of only 29%. Yields of less than 20-30% are generally not considered economical and present difficulties when attempting to scale the process to larger volumes. Yields provided using other known viral chromatography purification protocols, for viruses such as herpes simplex virus (HSV), adenovirus (e.g., serotype 5) and measles virus, are typically less than 50% and can often be less than 20%. Yields of different purification processes can also be compared by comparing the total amount of the product generated per comparable amount of input material. For example, the improved process described herein which uses the same or comparable amount of input material as Ouelette et al. (e.g., starting with about ~1E13 PFU) can reliably generate yields in the $5 \times 10^{12}$ pfu range. In contrast, the process described in Ouelette et al. only generate yields on the order of $1 \times 10^9$ to $5 \times 10^{10}$ pfu (e.g., starting with about >3E10 to about >1.5E12 PFU) with low reproducibility. Thus, the improved process described herein can reliably generate 5 trillion pfu of live viral product, in contrast to the maximum of 50 billion pfu high yield generated by the previously known process.

The yields achieved by the improved purification process were not achievable with the previously described processes, such as the one described in Ouelette et al., regardless of the purity level desired, since the "location" and quantity of the virus in the eluted column fractions was not precisely known until after the method was completed. A time-consuming detection method, namely, SDS-PAGE, was employed in Ouelette et al. to detect the virus in the fractions eluted during the last two chromatography steps (virus-binding ion exchange and size separation chromatography). It was discovered that a combination of the third and fourth chromatography steps and slow detection in the method described in Ouelette et al. led to decreased yields of the live infections virus. Virus inactivation (loss of infectivity) may be caused by the chromatography steps (in particular, virus-binding ion exchange chromatography requiring elution with a high-salt buffer) and the delays caused by the SDS-PAGE detection procedure. In the improved purification method, using a rapid and specific method for detecting the virus in the eluted fractions during the first chromatography step allowed elimination of subsequent potentially inactivating purification steps and reduce the total purification time, resulting in an unexpected improved yield of the live, infectious non-naturally occurring poliovirus, such as an oncolytic attenuated recombinant poliovirus exemplified by PVS-RIPO. As a result of the unexpectedly improved purification yields, the production process provided herein can produce approximately $3\times10^{12}$ Tissue Culture Infectious Dose $(TCID)_{50}$ of PVS-RIPO on a production scale of ten 10-tier "cell factories" comparable to those described herein. Due to such high output, the improved purification process can be adapted to or incorporated into a large-scale manufacturing process generating the live non-naturally occurring poliovirus, such as an oncolytic attenuated recombinant poliovirus exemplified by PVS-RIPO.

While in some examples a decrease in overall purity (as measured, for example, by detection of residual host cell protein (HCP) and Benzonase® enzyme) of the final product obtained using of the improved purification methods was observed, in comparison to the previously described processes, the resulting degree of purity of the virus produced (e.g., live non-naturally occurring poliovirus) was acceptable for large scale clinical manufacturing. It is shown herein that a 5-10 fold increase in yield over a previous process was achieved, while concomitant decrease in overall purity, as measured by residual HCP and Benzonase® enzyme, remained within the limits acceptable for clinical manufacturing. In some examples, the amount of Benzonase® enzyme in the final product is less than 50 ng/mL (such as less than 20 ng/mL, less than 10 ng/mL, less than 5 ng/mL, or less than 1 ng/mL), the amount of HCP in the final product is less than 10 mg/mL (such as less than 5 mg/mL, less than 2 mg/mL, less than 1 mg/mL or less than 0.5 mg/mL), or combinations thereof. Based on the teachings herein, one skilled in the art will appreciate that by varying the parameters used for selecting the fractions after the first chromatography steps, improved purity of the virus product can be achieved.

Generating Viral Template Plasmids

The disclosure provides an improved process for generating plasmid DNA containing viral template sequences. A comparison between the new and old methods is provided in FIG. 2, and details of the new method are provided in FIG. 3. The improved process for generating viral DNA template plasmid ensures that viral DNA template used for generating viral sequences contains the correct viral template sequences. The disclosed methods includes one or more of the following steps, which are described in more detail below: introducing a viral template plasmid into one or more host cells (such as a bacterial cell) (e.g., transformation); growing a solid-medium culture of the one or more host cells transformed with the viral template plasmid; detecting the presence of one or more viral sequences in one or more colonies grown on the solid-medium culture; propagating cells (e.g., by fermentation in liquid culture) of one or more colonies in which the presence of the one or more viral template sequences was detected, and extracting the viral plasmid from the propagated host cells. In some examples, freezing (e.g., exposure to, or incubation in, temperatures at or below −20° C. or −80° C.) of the host cells (e.g., bacterial cells) or a material derived from the host cells (e.g., bacterial cells) is intentionally not performed between propagation and extraction steps. Propagation time may also be limited. In some examples, the disclosed methods of plasmid preparation do not include exposing the transformed host cells to glycerol or other reagents typically added to storage media (e.g., DMSO). Thus, in some examples, the disclosed methods of plasmid preparation do not include incubating the transformed host cells in media containing glycerol or other reagents typically added to storage media (e.g., DMSO), and the transformed host cells are not frozen.

Figure 2:
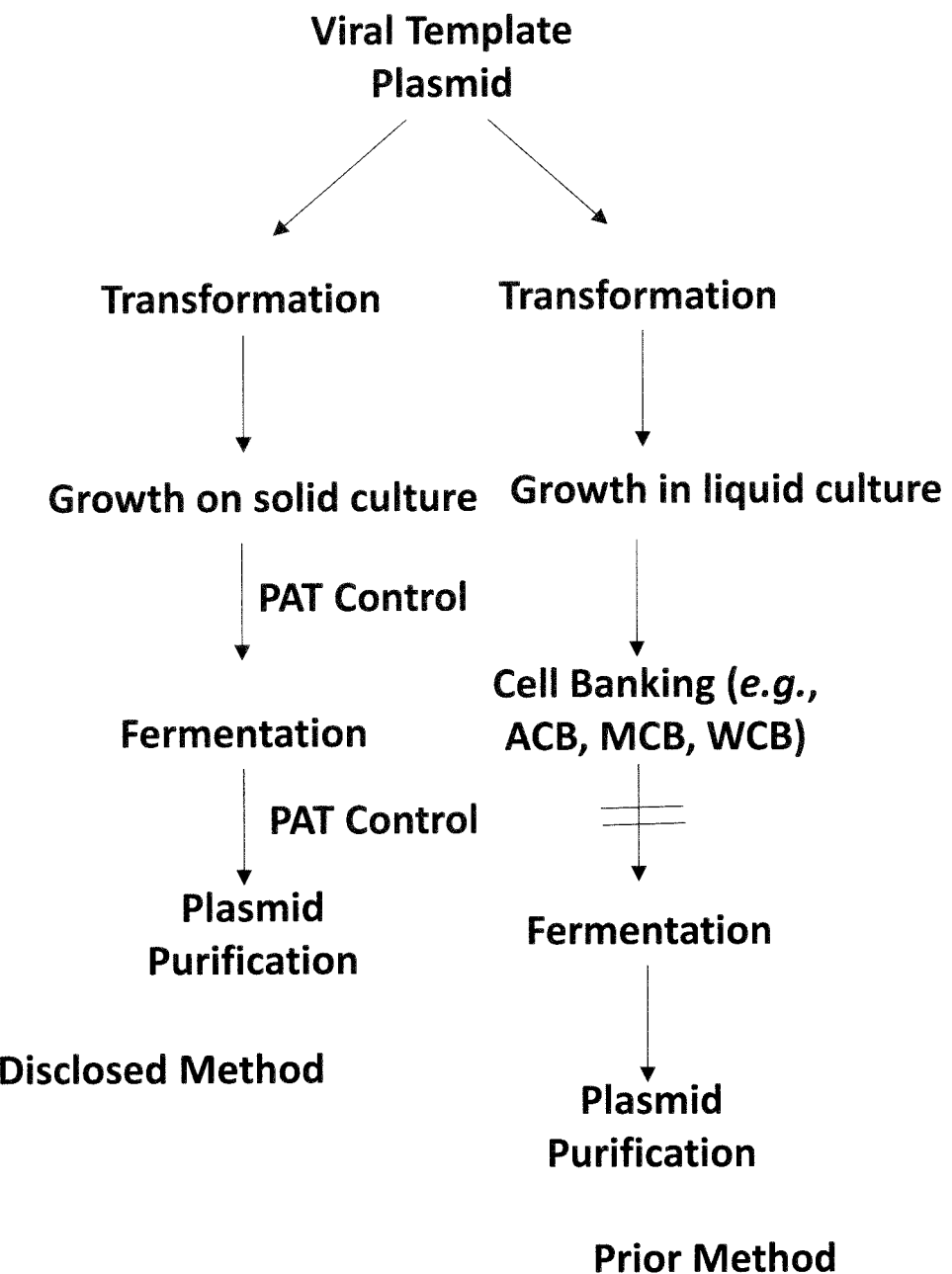

An overview comparing the old and new disclosed method is provided in FIG. 2. In both methods, a viral template plasmid containing the viral sequence and a selection marker (e.g., kanamycin resistance) is transduced into a host cell (e.g., E. coli). Transformed cells are grown in the presence of a suitable growth media containing the selection compound, such as kanamycin, to allow for selection of transformants. In the new method, this growth occurs on solid media, while in the prior method this growth occurs in liquid media. Growth on solid culture permits selection of individual transformed clones with the desired non-defective plasmid identified (PAT control). The PAT (Process Analytics Technology) control steps in the new method allow real-time monitoring and data-based decision making during the manufacturing process. For example, PAT can include rapid electrophoretic analysis of the plasmid to ensure that it is intact and of the correct size via clonal selection prior to fermentation and 'bulk sample' analysis after fermentation. In contrast, the old method grows transformed cells in liquid media, resulting in propagation of both defective plasmids and non-defective plasmids. In prior methods, following transformation, growth in liquid culture, and colony selection via a selection marker (e.g., antibiotic resistance), the cells are allowed to process to high titer and then cell banking is performed. At this stage, the transformed cells are placed in a storage media (typically containing glycerol) to create a frozen cell bank for subsequent manufacturing. Non-GMP banks are typically considered Accession Cell Banks (ACB), a portion of which is used to create the first GMP Master Cell Bank (MCB) via liquid media fermentation. The cell banks can be stored indefinitely, as indicated by the ≠ symbol in FIG. 2. A portion of the MCB lot is typically used to generate a Working Cell Bank (WCB) via liquid media fermentation that is used in the product fermentation process. In the new method, following growth on solid media, and selection of verified a clone with the correct plasmid, the transformed host cells re-expanded in liquid growth media under optimized conditions in order to manufacture the plasmid (Fermentation). In the prior method, banked cells (which have not had their plasmid verified) are expanded in liquid growth media under optimized conditions in order to manufacture the plasmid (Fermentation). Subsequently, in both methods, liquid cultures are pelleted and cells disrupted to release the plasmid DNA (Plasmid Purification). Subsequent chromatography, filtration, wash, buffer exchange, and concentration steps can be used to generate purified plasmid DNA with low residual concentrations of host cell chromosomal DNA, endotoxin (LPS), and/or host cell proteins.

The improved process address a problem of genetic instability of viral template plasmids propagated in host (e.g., bacterial) cells. Using prior purification methods, when PVS-RIPO plasmid is propagated in E. coli culture, the PVS-RIPO template sequences are unstable and prone to bacterial transposon insertion events. For instance, bacterial transposon TN10/ISR10, present in most Gram-negative bacteria, can rapidly insert itself into viral template sequences, resulting in defective virus template. PVS-RIPO plasmid product propagated in a bacterial culture and provided as frozen transformed *E. coli* stock (such as the viral plasmid stock used in Ouelette et al., which was fermented prior to plasmid purification—see Ouelette et al., page 32, column 1) typically contains a significant number of impurities, including empty pUC19 vector, dimerized pUC19 vector, or *E. coli* transposon DNA insertions (schematically illustrated in FIG. 1).

Prior methods of generating plasmid DNA containing viral template sequences also included introducing a viral template plasmid into one or more host (e.g., bacterial) cells, but subsequently such cells were grown in liquid media and then "banked" or frozen (see FIG. 2). In addition, no verification process was performed to confirm that the plasmid remained intact. A typical plasmid product may experience up to three or more cell banking fermentation and freezing procedures prior to fermentation for manufacturing purposes. It has been determined that obtained banks of plasmid DNA containing viral template contain a large population of plasmids that were degraded (e.g., did not include the correct viral template sequence, for example due to undesired transposon events), and thus not optimal. It was difficult to obtain the full-length clone from the starting material of these banks. In some examples, at least 70% (such as at least 80%, at least 90%, at least 95%, at least 98%, at least 99% or even sometimes 100%) of the plasmid population did not include the correct viral template sequence when the prior purification methods were used. It has been shown that using the new method, which avoids the banking step (e.g., there is no freezing step), results in a less degraded population of plasmids, possibly due to fewer transposon insertion events. For example, using the disclosed methods of producing viral template plasmid, can generate a population of plasmid DNA containing viral template sequences with at least 50% of colonies genetically 'stable' (such as at least 60%, at least 65%, at least 70%, or at least 75%) as indicated by agarose gel electrophoresis (AGE) and RE mapping of the plasmid population containing the correct viral template sequence (or less than 50% of the plasmid population containing the incorrect viral template sequence (such as less than 40%, less than 45%, less than 30% or less than 25%).

The improved process described herein addressed the problems associated with the prior method by one or more of the following features. In some examples, the improved process provides the initial viral template plasmid stock (e.g., PVS-RIPO viral DNA template plasmid) as a composition containing isolated viral template plasmid stock (e.g., PVS-RIPO plasmid DNA), instead of using transformed host cells (e.g., *E. coli*), and performing a fresh transformation of host cells (e.g., *E. coli*) using isolated viral template plasmid stock (e.g., PVS-RIPO plasmid DNA). In some examples, the improved process includes testing transformed cells for the presence of the correct plasmid sequence (e.g., using agarose gel electrophoresis and RE mapping). In the exemplary methods described herein, the testing is performed on the solid-media grown colonies of the bacterial cells, but any appropriate technique may be employed to test the transformed bacterial cells for the presence of correct viral template sequences and select the cells in which such sequences are present for further propagation. By including a testing or selection step, which is exemplified by detection of one or more viral template sequences in bacterial colonies grown from the cells transformed from the initial plasmid stock, the improved process ensures that bacterial cells containing correct or substantially correct viral template plasmid sequence are selected for further propagation. In some examples, the improved process does not include freezing the transformed host cells during or between propagation and isolation steps, which also reduced the risk of genetic instability of the viral template sequences present in the bacterial cells. Intentionally limited propagation time may also be employed in the improved process, to reduce the risk of amplifying a plasmid clone containing defective viral template sequences.

Figure 3:
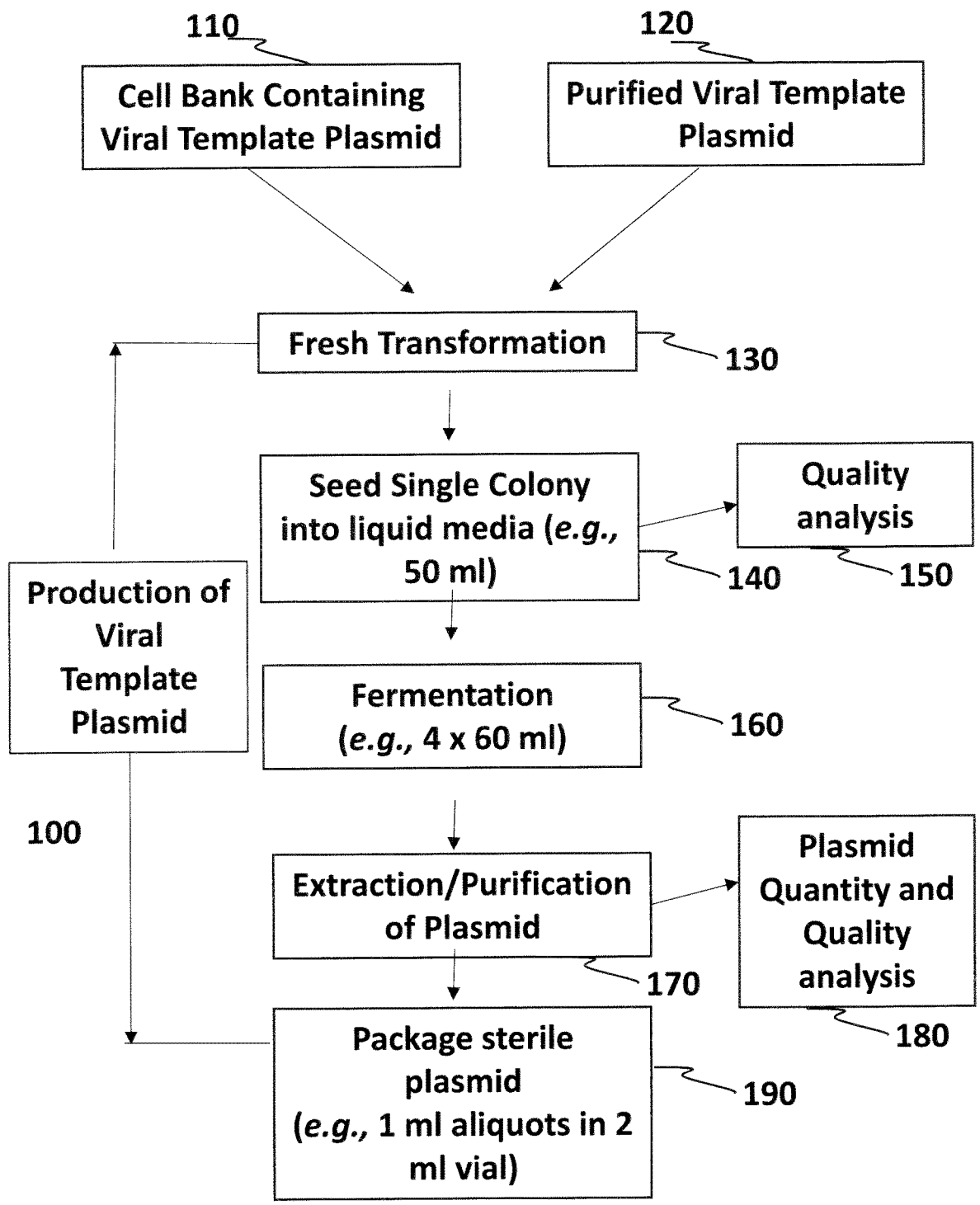

An overview of the disclosed method is provided in FIG. 3, 100. Plasmid DNA 110, 120 containing viral template sequences, which can be also referred to as plasmid viral DNA template, viral DNA template plasmid, viral template plasmid, plasmid, viral DNA template and by other related terms, is a plasmid containing one or more viral DNA template sequences specifying (meaning being complementary or coincident to) viral DNA or RNA sequences. A viral template plasmid can be obtained in the form of a purified plasmid stock, such as plasmid from a plasmid bank (110), or in some other form. In one example, the plasmid is provided in an isolated form (120), meaning not contained in bacterial cells. Viral DNA or RNA sequences can contain native viral sequence, engineered or modified viral sequences, or non-viral sequences, such as sequences encoding non-viral proteins to be expressed in the host cell. Viral DNA template is used to synthesize viral sequences in vitro (for example, RNA polymerase may be employed to synthesize viral RNA sequences in vitro from viral DNA template sequences) or in vivo, upon introduction of viral DNA template sequences into a host cell.

Any viral template plasmid can be purified with the disclosed methods. In some examples, the viral template plasmid includes a DNA template for an RNA virus, such as a polio virus (e.g., template for PVS-RIPO, inactivated polio virus (IPV), attenuated polio virus (i.e., Sabin vaccine). In one example, the viral template plasmid includes a DNA template for a positive-strand RNA virus, such as a Picornavirus (such as Aphthoviridae [for example foot-and-mouth-disease virus (FMDV)], Hepatitis A, or polio), Cardioviridae; Enteroviridae (e.g., Coxsackie viruses, Echoviruses, Enteroviruses, and Polioviruses); Rhinoviridae (rhinoviruses, such as rhinovirus A, B or C)); Togavirus (e.g., rubella; alphaviruses (such as Western equine encephalitis virus, Eastern equine encephalitis virus, and Venezuelan equine encephalitis virus)); Flavivirus (e.g., Dengue virus, Zika virus, West Nile virus, hepatitis C virus, and Japanese encephalitis virus); and Coronavirus (e.g., SARS coronaviruses, such as the Urbani strain). In one example, the viral template plasmid includes a DNA template for a negative-strand RNA virus, such as an Orthomyxyovirus (such as influenza, such as influenza A or B), Rhabdovirus (such as Rabies), Filoviridae (such as Ebola), and Paramyxovirus (such as measles virus, respiratory syncytial virus, and parainfluenza viruses). In some examples, the viral template plasmid includes a DNA virus sequence, such as one from a Herpesvirus (such as Varicella-zoster virus, for example the Oka strain; cytomegalovirus; and Herpes simplex virus (HSV) types 1 and 2), adenovirus (such as adenovirus type 1, type 14, type 5, type 40, or type 41), Poxvirus (such as Vaccinia virus), Hepatitis B virus, and Parvovirus (such as Parvovirus B19). In some examples, the viral template plasmid includes a DNA or RNA template for a retrovirus, such as human immunodeficiency virus type 1 (HIV-1), such as subtype C, HIV-2; equine infectious anemia virus; feline immunodeficiency virus (FIV); feline leukemia viruses (FeLV); simian immunodeficiency virus (SIV); and avian sarcoma virus.

As shown in FIG. 3, the viral template plasmid is introduced (e.g., transformed) into one or more host cells, 130. Exemplary host cells that can be used include but are not limited to: bacteria, archea, plant, fungal, yeast, and insect cells, such as *Lactobacillus, Lactococcus, Bacillus* (such as *B. subtilis*), *Escherichia* (such as *E. coli*, for example DH5a, K12, or a K12-derived strain of *E. coli*), *Clostridium, Saccharomyces* or *Pichia* (such as *S. cerevisiae* or *P. pastoris*), *Kluyveromyces lactis, Salmonella typhimurium*, SF9 cells, C129 cells, 293 cells, *Neurospora* cells, and mammalian cells. The introduction of the viral template plasmid into the host cell can be accomplished by any suitable method. Exemplary transformation methods include but are not limited to: electroporation or exposure of host cells to divalent cations, for example, $Ca^{2+}$, followed by heat shock.

Following transformation 130, the transformed host cells are grown on solid medium (e.g., agar plates), in the presence of the selection marker (e.g., antibiotic). Growth of a solid-medium culture of one or more cells transformed with the viral template plasmid can be accomplished by any suitable method. For example, the transformed cells can be streaked or dilution plated onto a solid medium, such as an agar-based bacterial growth medium. Individual colonies are selected, and separately expanded in liquid media (for example in 50 mL media), 140. Selection for the transformed cells using a suitable selection marker in liquid or solid media can be employed. For example, selection for a gene conferring antibiotic resistance contained in the viral plasmid DNA may be accomplished by using a growth medium containing the antibiotic, such as, but not limited to, media containing kanamycin for KanR selection of plasmid transformants (or others, such as media containing ampicillin for AmpR selection of plasmid transformant). Other antibiotic resistance markers that can be used include hygromycin, chloramphenicol, and puromycin. In addition, other selection methods can be used such as beta-galactosidase alpha complementation (using *E. coli* lacZΔM15 as the host) and plating with X-gal.

After allowing the transformed host cells to grow (e.g., under selection conditions), it is determined which bacterial colonies contain correct viral template sequences, 150. Detection of the presence of one or more viral template sequences in one or more bacterial colonies grown on the solid-medium culture can be accomplished by one or more suitable detection methods. For example, one or more of a polymerase change reaction (PCR), DNA sequencing, restriction analysis, gel electrophoresis, blotting or other methods can be performed. In one example, restriction mapping agarose gel electrophoresis, ultimately followed by complete plasmid sequencing, is used. Detection of the presence of one or more viral template sequences is performed to verify that the cells of the one or more colonies tested contain a correct or substantially correct DNA sequences of viral template and do not contain substantial amount of impurities, such as "empty" plasmid vectors not containing viral template sequences, plasmid dimers and such, or viral DNA sequence variations or errors, such as deletions, insertions or substitutions.

Propagation of the transformed cells of the one or more colonies in which the presence of the one or more viral template plasmid sequence was detected may be achieved by any suitable method, as well as the extraction of the viral plasmid from the propagated cells. For example, as shown at step 160, a colony in which the presence of the one or more viral template plasmid cells was detected may be used to inoculate a liquid culture of transformed cells, which can then be grown ("fermented") to a suitable degree. The cells containing the plasmid can be then be purified, for example separated from the growth medium by sedimentation, filtration or other appropriate separation process. The viral DNA template plasmid can be extracted (e.g., purified or isolated) from the cells by appropriate techniques, 170. The resulting isolated viral DNA template plasmid can be analyzed 180 for quantity of plasmid and quality of plasmid (e.g., to determine if the plasmid include the correct sequence). For example, step 180 can include determining DNA concentration of the resulting sample, *E. coli* LAL (endotoxin) concentration, plasmid DNA purity in the resulting sample, or combinations thereof. Such methods may include restriction digestion analysis and/or sequencing analysis. Following purification, diafiltration, and sterile filtration, the resulting plasmid can then be packaged, 190, for example 1 mL in a 2-3 mL glass vial. In some cases, the disclosed method intentionally does not include any freezing steps or periods between the propagation and extraction steps (e.g., steps 130-170). Propagation time may be intentionally limited to approximately 14 hours for the plasmid starter culture and a main fermentation of approximately 20 hours.

Figure 1B:
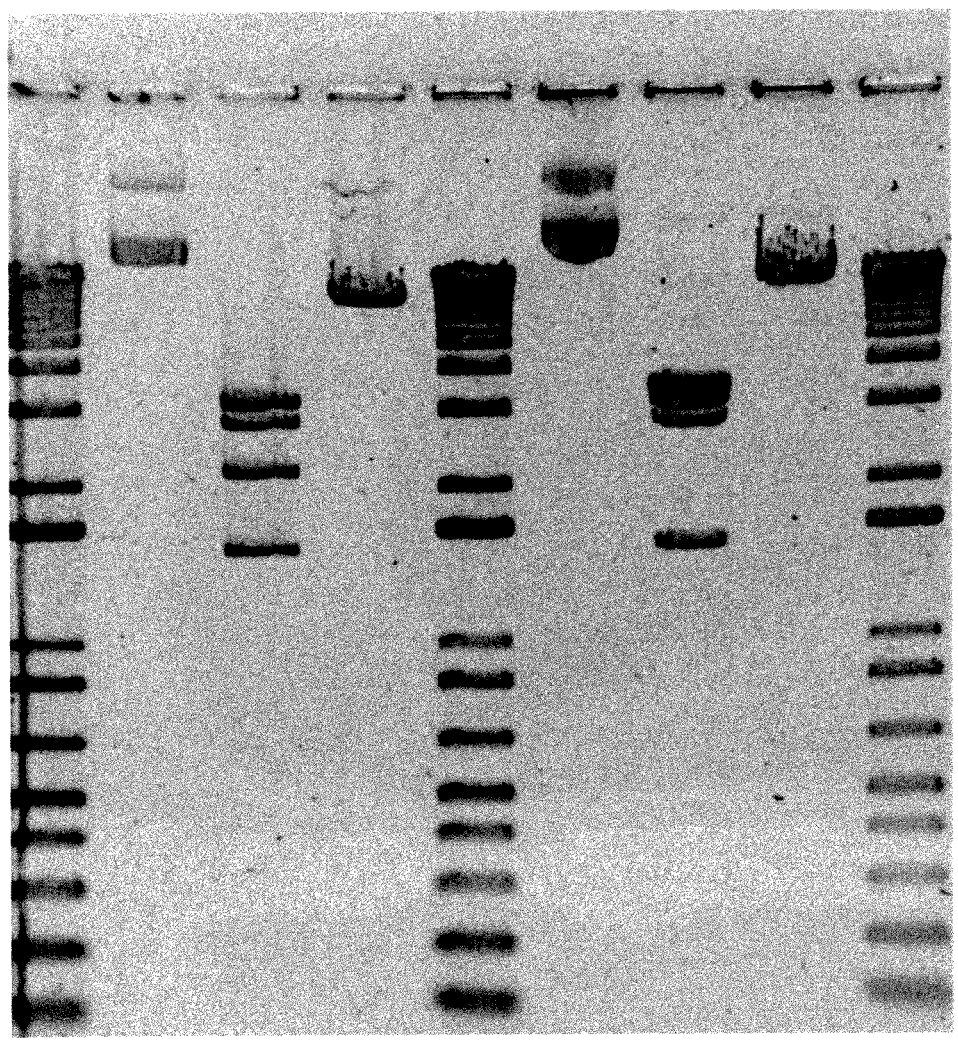
Figure 4:
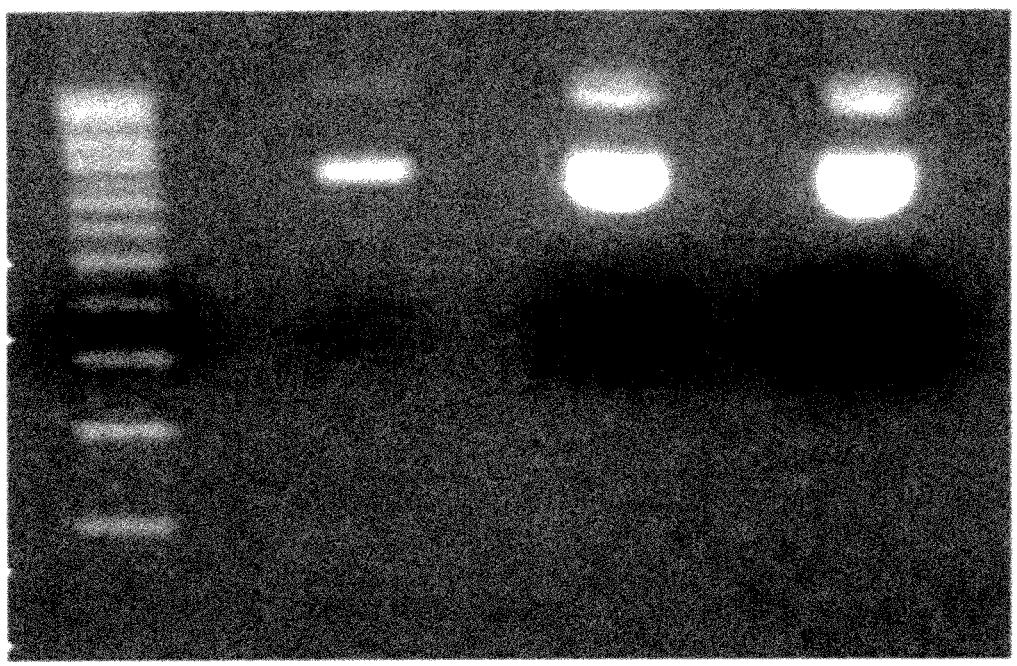

In a specific example of the improved process, *E. coli* cells were transformed with a PVS-RIPO viral DNA template plasmid (two different lots were used) using heat shock. The transformed cells were grown on solid medium. Resulting colonies of the *E. coli* cells were screened to identify those containing the correct PVS-RIPO plasmid using AGE (scDNA and RE mapping analysis). Additional screening can be performed via plasmid DNA sequencing. *E. coli* cells containing the correct PVS-RIPO plasmid were selected for further propagation, propagated in liquid *E. coli* cell culture medium containing LB-Soytone with 50 µg/mL kanamycin, and PVS-RIPO plasmid was isolated from propagated *E. coli* cells (the cell paste was centrifuged and lysed/purified using Qiagen® EndoFree GigaPrep kits) without freezing the bacteria. Propagation is limited to a predetermined cell density by measuring OD600 nm, use of a gel-based check between the starter seed culture and the main fermentation, use of parallel cultures for both the starter and main fermentations, and immediate processing of the plasmid (i.e., no frozen cell pastes). FIG. 4 illustrates improved purity of the PVS-RIPO plasmid obtained by the improved plasmid production process relative to FIGS. 1A and 1B. Using the disclosed methods, the recovery of intact full length (~10 kbp) plasmid with a high super coiled (sc) DNA percentage (e.g., at least 70%, at least 80%, at least 85%, at least 90%, at least 95%, at least 98%, or at least 99%, such as 70-95%, 75-85%, or 80-90%) was achieved. In addition, there were no indications of complete or partial plasmid loss, plasmid insert loss, recombination, or transposon integration, using AGE and AGE/RE mapping analysis.

Viral template plasmid DNA produced using the disclosed methods are also provided. For example, a composition containing viral template plasmid DNA produced using the disclosed methods can include buffer, such as 10 mM Tris, 1 mM EDTA, pH 8.0. In some examples, the resulting viral template plasmid DNA includes plasmids, at least 50% of which contain the proper viral DNA template plasmid (e.g., at least 50%, at least 60%, at least 70%, at least 75%, such as 50-75%, 50-85%, or 50-60%, of clones contain a sole plasmid construct of the desired size and restriction mapping patterns following the disclosed methods, e.g., for PVSRIPO pDNA). In some examples, a composition containing viral template plasmid DNA produced using the disclosed methods includes fewer plasmids with transposon insertion events, fewer plasmids that have dimerized, fewer empty plasmids without a viral template sequence, or combinations thereof, as compared to such events observed when other purification methods are used. Thus, in some examples, a composition containing viral template plasmid DNA produced using the disclosed methods includes less than about 50% plasmids with transposon insertion events (such as less than 45%, less than 40%, less than 30%, less than 20%, less than 10%, less than 5%, or less than 1%, such as 10-50%, 20-40%, or 1 to 20%), less than about 25% dimerized plasmids (such as less than 20%, less than 15%, less than 10%, or less than 5% such as 1-25%, or 10-20%), less than about 25% empty plasmids (such as less than 20%, less than 15%, less than 10%, or less than 5% such as 1-25%, or 10-20%) without a viral template sequence, or combinations thereof.

Viral template plasmid DNA produced using the disclosed methods may be further treated, for example, linearized, to produce viral DNA template, and introduced into host cells. For example, for RNA-based viruses, viral RNA sequences may be generated from viral DNA template using in vitro transcription and used to transfect viral host cells. Clarified virus from the transfected host cells may be collected and referred to as a "master viral bank" (MVB). A MVB contains virus and not host cells. Due to their short life span, infected cells are not usually collected into a cell bank. MVBs contain post-transfection cell lysates containing clarified virus. The infected viral host cells are then grown in a suitable way, such as in in vitro cell culture. Growth of the infected cells may include one or more rounds of amplification (expansion) of the infected mammalian cells in culture, meaning growing the cells in culture, and then using the grown cells to "seed" (initiate) additional cell cultures, although this may not be possible due to the rapidity of cytopathic effects and cell death following infection.

In an example of the improved process, master viral seed (MVS) is created in Vero cells transformed by IVT-generated viral RNA; the MVB virus is created using the MVS infected expanded Vero cells and is subsequently clarified but not purified; the production lots use Vero cells infected with the virus form the MVB lot; in all cases, the Vero expansion occurs prior to transfection (viral RNA to MVS) or infection (MVB) and production. However, the cell expansion required is typically less for generating small MVS/MVB banks versus larger scale manufacturing lots of virus. Therefore, PVS-RIPO plasmid DNA, produced as described above, was used and the resulting naked viral RNA sequences were used to transfect Vero mammalian cells. The Vero cultures are expanded to the desired cell count prior to RNA transfection or viral infection. For PVS-RIPO and other viruses, cells are not expanded after infection. Viral replication and amplification occurs in the infected Vero cells to generate a harvest lot of PVS-RIPO.

Purification Process Employing a Rapid Detection Method of Nucleic Acid Sequences in Chromatography Fractions Provided herein are improved processes or methods for obtaining purified or isolated nucleic acid molecule-containing composition. The improved purification processes include chromatographic separation of a sample containing a desired nucleic acid molecule, such as a virus. It is shown herein that by detecting the desired nucleic acid molecule-containing composition being purified (e.g., the "analyte") in eluted chromatography column fractions using a rapid detection method, such as quantitative polymerase chain reaction (qPCR), and selecting the fractions based on the detection results (e.g., selecting and combining the fractions containing the desired nucleic acid molecule), improved purification was achieved in comparison to a process, in which sample detection is conducted by traditional chromatography monitoring techniques, such as monitoring absorbance and conductivity of the chromatography column eluate. Although increased yields of live, infectious virus were achieved with the improved purification process described herein, the method is not limited to purification of live viruses. For example, the disclosed methods can be used to purify other analytes, such as an inactivated virus (e.g., one used in a vaccine,) and purified viral nucleic acids.

The improved purification process can result in one or more of higher yields of the analyte, increased purity of the analyte, and reduced purification time (see Table 2). Reduced purification time leads to improved purification efficiency and, in some cases, to improved quality of the purified analyte. For example, purification of PVS-RIPO using the improved purification process was achieved in 4-8 hours (as compared to at least 2 days or at least 3 days with the method of Ouelette et al.), which leads to improved infectivity (titer) of purified PVS-RIPO. In other words, shorter purification time leads to improved yield and stability of live, infectious virus. The parameters, such as yield and purity of the analyte obtained by the improved purification process, or purification time, can be manipulated by adjusting the purification parameters. For instance, one can adjust (increase or decrease) a number of chromatography fractions being collected and/or tested by the rapid detection method for the presence of the analyte, increasing chromatography column resolution, adding additional purification and/or detection steps or selecting different types of rapid detection methods. In one example, overall yields of the analyte can be improved by testing a large number of chromatography fractions and pooling more of the analyte-containing fractions for further preparation steps. In another example, purity of the analyte can be improved by collecting smaller fractions and pooling a small number of fractions with the highest analyte content for further preparation steps.

TABLE 2

Improved output of the disclosed methods

| | New/Disclosed Method | Prior Methods |
|---|---|---|
| Purification Yield* | At least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, or at least 85%, for example 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 805, 81%, 82%, 83%, 84%, or 85%, such 50%-60%, 50-80%, 50-83%, 50-85%, 60-83%, 60-85%, 70-83%, or 70-85% | Less than 50%, less than 40%, less than 30%, less than 29%, less than 20%, or less than 5%, such as 20% to 50%, 20-30%, 10-30%, 5% to 30%, or 1% to 30%. |
| Yield (Percentage recovery based on Input (harvest) vs. output (product) PFU) | Recovery is at least 50% of the starting material, such as at least 51%, at least 52%, at least 53%, at least 54%, at least 55%, at least 56%, at least 57%, at least 58%, at least 59%, at least 60%, for example 50%, 51%, 52%, 53%, 54%, 55%, 56%, 57%, 58%, 59%, or 60%, such 50%-60%, 50-55%, or 55-60%. For example, a yield of at least $5 \times 10^{11}$ pfu, $1 \times 10^{12}$ pfu, or at least with $5 \times 10^{12}$ pfu$^{14}$ from $1 \times 10^{14}$ pfu starting material | Recovery is variable and unpredictable, such as a few % to 50%, such as no more than 10%, no more than 5%, or no more than 1%, such as 1%-10%, 5%-10%, or 1 to 5%. In other examples, higher yield is obtained, such as about 50%. For example a yield of $1 \times 10^9$ to $5 \times 10^{10}$ pfu with $1 \times 10^{10}$ to $1 \times 10^{13}$ pfu of starting material |
| Time to Perform Purification Assay | 4 to 8 hours | 2-3 days, or 12-18 hours (theoretically if done continuously) |

TABLE 2-continued

Improved output of the disclosed methods

| | New/Disclosed Method | Prior Methods |
|---|---|---|
| Infectivity (titer) of virus | At least $1 \times 10^{12}$ Tissue Culture Infectious Dose $(TCID)_{50}$ (such as at least $3 \times 10^{12}$ $TCID_{50}$, at least $1 \times 10^{13}$ $TCID_{50}$, or at least $1 \times 10^{14}$ $TCID_{50}$) on a production scale of ten 10-tier "cell factories" | About $3 \times 10^{10}$ $TCID_{50}$ to $3 \times 10^{12}$ $TCID_{50}$ on a production scale of ten 10-tier "cell factories" |

*The ratio between total plaque forming units (pfu) from the purified virus obtained after the last process step and those viruses harvested from host cell culture (e.g., the viruses in a mammalian cell, such as a Vero cell, that are used as the source of the virus to be purified)

Figure 5:
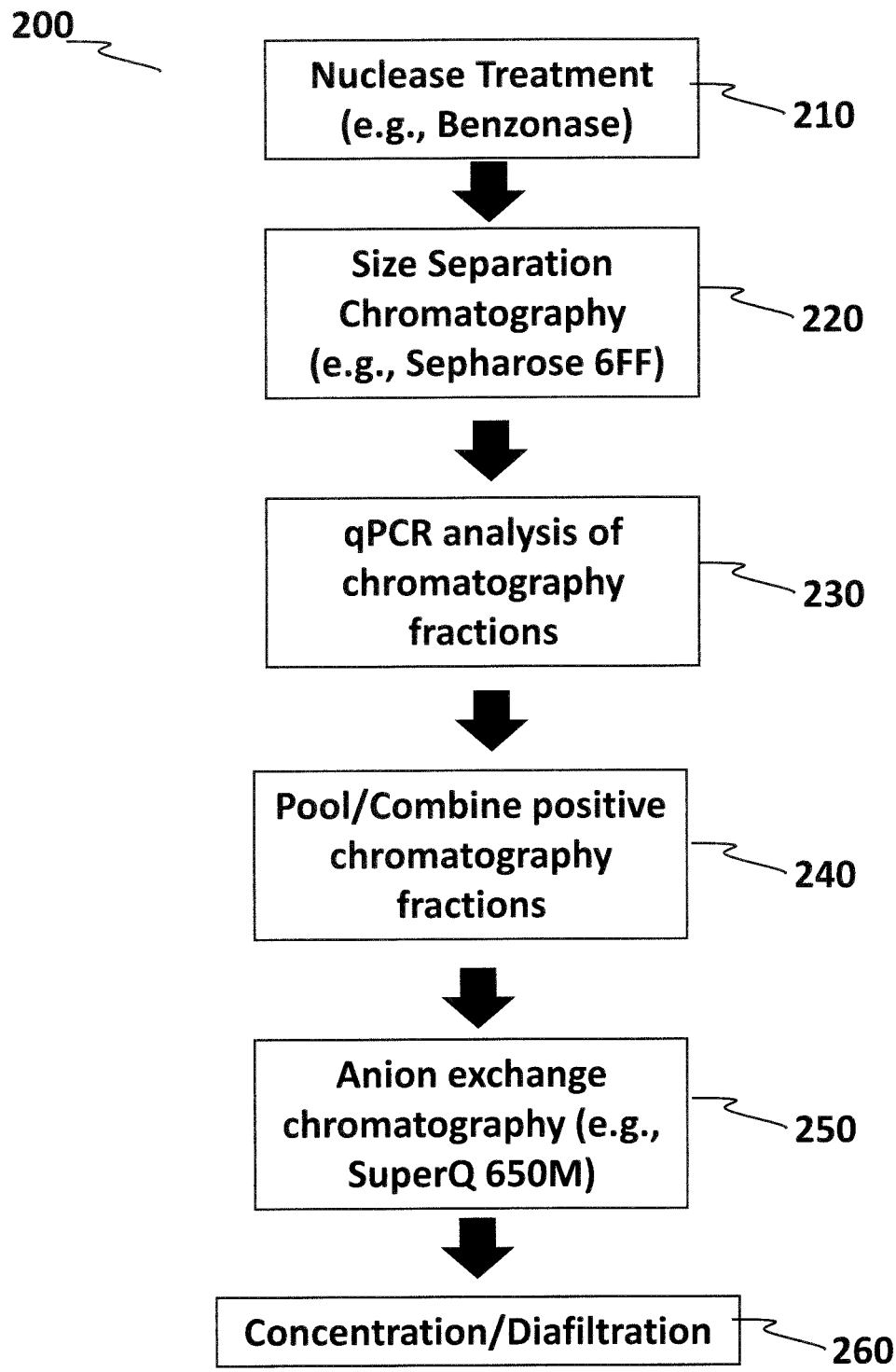

An overview of the improved methods is provided in FIG. 5, 200. Host cells previously infected with a viral template plasmid and growing in culture, such as Vero cells infected with a polio virus (such as PVS-RIPO), are lysed by the virus. The resulting supernatant is incubated with a nuclease enzyme 210. The nuclease can digest free RNA and DNA in solution, but leave encapsulated viral nucleic acids (i.e., contained in intact viral particles) intact. Thus, the nuclease is incubated with supernatant containing the desired virus under conditions that permit digestion (and therefore reduction and/or removal) of host cell DNA (e.g., gDNA, mtDNA) and RNA (e.g., tRNA, rRNA), other potential contaminating DNA/RNA (e.g., endogenous/exogenous viruses) if present, and unencapsulated free viral RNA. In one example, the nuclease is present at a concentration of 50 units/ml (or less), for example at 2-8° C. for 16-24 hours. In some examples, the nuclease is used at a higher temperature (e.g., 25-37° C.) for shorter times, but viral capsid degradation may occur. In one example, the nuclease is an endonuclease, such as Benzonase® enzyme. In one example, the nuclease is one or more DNases, one or more RNases, or combinations of one or more DNases and one or more RNases.

The nuclease-digested supernatant is then subjected to size separation (or gel filtration) chromatography, 220. For example, the nuclease-digested supernatant can be applied to a size separation column, such as one containing an agarose based resin (e.g., Sepharose). In one example, the size separation column is a Sepharose 6 Fast Flow (FF) resin, which has a high flowrate. In some examples, use of a 6FF instead of a 4FF column can improve purity of the virus and/or increase the speed of purification. One or more fractions collected from the column are analyzed for the presence of the target nucleic acid molecule (e.g., by detection of a target sequence of the target virus) using qPCR (such as real time RT-qPCR), 230. In some examples, other parameters of the eluate are also monitored, such as the absorbance (e.g., at one or wavelengths of 280 nm, 215 nm, or 254 nm), and/or conductivity. Fractions identified has containing the target nucleic acid molecule (e.g., virus) are then pooled or combined 240. In one example a positive fraction is one having $>10^7$ copies/mL (wherein copies refers to viral RNA or cDNA genome copies).

The pooled fractions are subjected to anion exchange chromatography, 250. For example, the pooled fractions can be applied to a Super Q 650M resin-containing column. In some examples, parameters of the eluate from the anion exchange are monitored, such as the absorbance (e.g., at one or wavelengths of 280 nm, 215 nm, or 254 nm), and/or conductivity. In some examples, the eluate from the anion exchange is monitored for the presence of the virus, for example using PCR (e.g., real time RT-PCR). For example, fractions containing at least $5 \times 10^9$ copies/mL can be kept and pooled, although this can be expanded to fractions containing at least $2 \times 10^9$ copies/mL to improve yield at a cost to purity (e.g., if yield is more desired than greater purity).

The resulting flow-through peak collected from the anion exchange column, which contains the target nucleic acid molecule(s), can be concentrated using diafiltration, 260. The resulting permeate and/or flushes can be collected, pooled, sterile filtered, or combinations thereof. If desired, the resulting permeate and/or flushes can be further analyzed, for example determining the pH, BCA (protein content), Vero HCP content, HC DNA content, LAL, performing plaque (PFU) testing, or combinations thereof. In some examples, additional materials are added to the resulting purified nucleic acid molecule preparation, such as one or more of an adjuvant, human serum albumin (HSA), sugar (mannitol, sucrose, etc.), surfactant (e.g., Tween/Polysorbate), and the like.

Chromatography

The disclosed methods for obtaining a composition containing nucleic acid molecules, such as purified virus, includes separation of a sample containing the desired nucleic acid molecules by liquid column chromatography, collecting fractions eluted from the column chromatography, detecting in one or more of the fractions the target nucleic acid sequence in the nucleic acid mixture using a rapid detection method, such as real time RT-qPCR, and selecting one or more of the fractions in which the target nucleic acid molecule is detected based on the predetermined threshold ("cutoff") concentration of the target nucleic acid molecule (such as threshold of $>10^9$ copies/mL (i.e., copies of the viral genome as determined by real time RT-qPCR). Column chromatography encompasses all methods that allow separation of components of a sample containing a nucleic acid molecule and involve a column packed with a stationary phase (chromatography medium) and mobile phase (liquid eluent), in which the sample is soluble. The sample is applied to the column, followed by application of the eluent. The stationary and the mobile phases are selected in such a way that various components of the sample travel through the stationary phase differently. Exemplary liquid chromatography methods suitable for separation of nucleic acid-containing samples are known and described, for example, by McLaughlin, *TrAC Trends in Analytical Chemistry* 5(8): 215-219 (1986) or McGrath et al., *J Virol.* 25(3):923-927 (1978). For example, liquid column chromatography methods can be classified based on the type of the medium and/or on the separation process involved. Some examples are size exclusion (gel filtration) chromatography, ion exchange chromatography, hydrophobic chromatography and affinity chromatography. Some examples of suitable chromatography media that can be used with the disclosed methods are Q-Sepharose FF, SP-Sepharose, Superdex-75, Capto-Q, Source-Q, DEAE-Sephacel, Zenix-C, Source-S, Phenyl/Butyl/Octo-Capto, and the like.

The eluate from the column is typically collected in a series of fractions (samples of a predetermined volume). Fractions can be subjected to various detection methods to determine the presence or absence of one or more of the sample components, which can be referred to as analytes.

Continued monitoring of the eluate may also be employed, such that detection is conducted continuously on a column eluate, which is then collected into fractions. Exemplary detection methods are absorbance detection at the wavelengths suitable for detection of nucleic acids and/or proteins or conductivity monitoring to detect electrolytes, such as salts. Fractions can be analyzed for the presence or absence of biological molecules using one or more of the suitable analytical techniques, such as enzyme activity testing, electrophoresis, blotting, etc. The detection techniques typically employed during separation of nucleic acid-containing samples lack specificity. For example, detection by measuring absorbance at a suitable wavelength, such as 254 nm for RNA, may be employed, but it does not allow for detection of a specific nucleic acid sequence (e.g., viral target sequence), and the resulting sample therefore may contain undesirable contaminants, such as host cell RNAs. However, more specific detection methods may be time-consuming, which can lead to undesirable degradation of the sample while obtaining the detection results.

In the disclosed improved purification process, regardless of the type of chromatography medium employed for separation of the sample containing a nucleic acid molecule (such as viral nucleic acids), the method includes detecting or measuring the target nucleic acid molecule in one or more of the fractions using a rapid detection method that can specifically detect one or more sequences in nucleic acid molecule-containing analyte. An example of such method is real-time RT-qPCR detection. Other detection techniques, such as absorbance and conductivity monitoring, can be employed in conjunction with rapid detection. For example, when real RT-qPCR is employed for rapid detection, fractions for real time RT-qPCR detection may be selected based on the results of absorbance and conductivity monitoring. However, the selection of the one or more of the fractions in which the target nucleic acid molecule is present is based on the real time RT-qPCR detection of the target nucleic acid sequence in the sample. The fractions are selected based on the predetermined threshold ("cutoff") concentration of the target nucleic acid sequence present in the sample. Namely, the fractions containing a concentration of the target nucleic acid sequence at or above the threshold value are selected. Multiple fractions can then be combined. The resulting composition contains a higher concentration of the target nucleic acid molecule than the sample originally applied onto the chromatography column. It may also contain a lower concentration of sample components other than the desired nucleic acid.

The disclosed purification methods were illustratively employed in a purification process of PVS-RIPO obtained from Vero cells. The PVS-RIPO production process involved multiple ten-tier cell factories of Vero cells infected by Passage 1 (P1) PVS-RIPO obtained from master viral bank. Harvested material (cell medium supernatant) was treated with Benzonase® enzyme and purified by two column chromatography steps, Sepharose 6FF size separation chromatography and Super-Q 650M anion exchange chromatography. Both chromatography steps were "flow-through" for PVS-RIPO, meaning that it did not bind to the column media and thus was eluted in the flow-through eluate. In the first chromatography step, a Sepharose 6FF column was used to separate lower molecular weight contaminants in the cell culture medium and as a buffer exchange step. In addition to identifying the main virus peak using continuous absorbance monitoring (UV absorption at 260 nm/280 nm), fractions were collected across the peak and further analyzed using real time RT-qPCR. The chromatogram usually contained two defined UV absorbance peaks. In the previous PVS-RIPO purification processes, such as the one described in Ouelette et al. (which used Sepharose 4FF, not 6FF) fraction pooling decisions were based on absorption monitoring, leading to purification yields of approximately 80% at this stage. In contrast, RT-qPCR detection led to yields of approximately 100% at this step. Surprisingly, fraction analysis by real time RT-qPCR indicated that the main PVS-RIPO virus peak was located approximately near the small initial UV absorbance peak, while the larger subsequent absorbance peak contained only trace amounts of PVS-RIPO. In some cases, the A254 "small initial peak" and RT-qPCR results did not completely overlap, indicating the initial A254 nm peak may not be solely due to viral RNA. RT qPCR detection was therefore unexpectedly critical in ascertaining the appropriate fractions to collect (a threshold of $>10^7$ copies/mL was used) for further processing. The unexpected increase in PVS-RIPO concentration and decrease in contaminants obtained after Sepharose 6FF chromatography rendered unnecessary the CMD anion exchange and Sephadex G-25 chromatography steps described in Ouelette et al. Selected fractions were pooled and further purified in the second SuperQ 650M chromatography step. The SuperQ 650M column was used to remove host cell protein contaminants from the non-binding virus. After purification, PVS-RIPO composition was concentrated, filtered, and vialed.

The average production yield of the live, infectious PVS-RIPO obtained by the disclosed process was reproducibly ≥50%, for example, in the range of 50%-80%. The time, the cost and the complexity of the purification process was significantly reduced, since it employed only two column chromatography steps, in comparison to four chromatography steps described in Ouelette et al. This improved production and purification process can be employed in the clinical manufacturing of recombinant polioviruses or other viruses, resulting in one or more of: improved production yields, infectivity, and purity of the final purified product. For example, the disclosed methods can be used for the clinical manufacturing of other recombinant viruses, for example, those produced from unstable plasmid vectors. Any plasmid propagated in *E. coli* containing an intact native RNA virus sequence (especially those from ssRNA viruses) are inherently unstable. Examples include but are not limited to, HIV, human T-cell lymphotrophic virus (HTLV), Rabies, Hepatitis C, measles, Ebola and other hemorrhagic viruses.

Detection of Target in Chromatography Fractions

Various rapid detection methods for detecting the analyte in chromatography fractions can be employed in the improved purification process. The detection method can allow for detection of nucleic acid sequences (such as DNA, cDNA or RNA sequences) in the nucleic acid-containing analyte. Exemplary detection methods include nucleic acid sequencing, nucleic acid amplification (e.g., PCR), and direct detection using labeled sequence-specific nucleic acid probes. In one example the label is fluorescence or enzymatic/colorimetric based. Thus, in some examples, the detection method includes rapid direct sequencing (such as from Illumina or nano-pore based methods), ligase chain reaction (LCR), BIAcore (surface plasmon resonance) and Octet (interferometry) using probes that bind to a viral sequence. In some embodiments, quantitative PCR (qPCR) is employed. Quantitative PCR refers generally to a method that allows for quantification of the amounts of the target nucleic acid sequence used at the start at the PCR reaction.

Quantitative PCR techniques use various approaches to quantification. One example of a quantitative PCR method is RT-qPCR (Reverse Transcription Quantitative PCR). Here, the term "quantitative PCR" encompasses all PCR-based techniques that allow for quantification of the initially present target nucleic acid sequences. The term "real time PCR" denotes a subset of quantitative PCR techniques that allow for detection of PCR product throughout the PCR reaction, or in real time. The principles of real-time PCR are generally described in Held et al., *Genome Research* 6:986-994 (1996). Generally, real time PCR measures a signal at each amplification cycle. Conventional real-time PCR techniques rely on fluorophores that emit a signal at the completion of every multiplication cycle. Examples of such fluorophores are fluorescence dyes that emit fluorescence at a defined wavelength upon binding to double-stranded DNA, such as SYBR green. An increase in double-stranded DNA during each amplification cycle thus leads to an increase in fluorescence intensity due to accumulation of PCR product. Another example of fluorophores used in real-time PCR is sequence-specific fluorescent reporter probes. The examples of such probes are TaqMan® probes and FRET probes. TaqMan® probes contain a fluorophore and a fluorescence quencher, which reduces the fluorescence emitted by the fluorophore. During the extension phase of PCR, the probe is cleaved by the exonuclease activity of the DNA polymerase, releasing the fluorophore. The fluorophore release results in in an increase in fluorescence signal, which is proportionate to the amount of the PCR product. FRET probes employ fluorescence resonance energy transfer (FRET). Two labeled sequence-specific probes are designed to bind to the PCR product during the annealing phase of PCR, which results in an energy transfer from a donor fluorophore to an acceptor fluorophore. This results in an increase in fluorescence during the annealing phase, which is proportional to the amount of the PCR product. The use of sequence-specific reporter probe provides for detection of a target sequence with high specificity, and enables quantification even in the presence of non-specific DNA amplification. Fluorescent probes can also be used in multiplex assays—for detection of several genes in the same reaction—based on specific probes with different-colored labels. For example, a multiplex assay can use several sequence-specific probes, labeled with a variety of fluorophores (including, but not limited to, the following: FAM, JA270, CY5.5, and HEX) in the same PCR reaction mixture.

Using the Purified Virus

Viruses purified with the disclosed methods can be used clinically, for example as a vaccine, such as in cancer immunotherapy or to provide a protective immune response.

In one example, the purified poliovirus, such as PVS-RIPO, is used to treat a subject with cancer, such as glioblastoma. For example, the subject can be administered about $1\times10^8$ TCID50 per direct tumor administration. At least two weeks later, the subject can undergo biopsy to confirm diagnosis/recurrence of the cancer. Once diagnosis is confirmed, the subject can have a catheter placed for convection-enhanced delivery of the PVS-RIPO ($5\times10^7$ $TCID_{50}$). After catheter placement, the subject is infused with the PVS-RIPO over 6.5 hours. The catheter can be removed after infusion is complete. MRIs can be performed to monitor the therapy.

In one example, the purified poliovirus, such as an attenuated Sabin poliovirus, is used to vaccinate a subject for protection against polio. For example, the purified attenuated Sabin poliovirus can be administered orally in a single dose (usually two drops, which contains 1,000,000 infectious units of Sabin 1 (effective against PV1), 100,000 infectious units of the Sabin 2 strain, and 600,000 infectious units of Sabin 3). Such a vaccine may also include small traces of antibiotics (e.g., neomycin and streptomycin), but no preservatives.

In one example, the purified poliovirus, such as an inactivated poliovirus, is used to vaccinate a subject for protection against polio. For example, the purified OPV can be administered via injection in a single dose (e.g., along with diphtheria, tetanus, and acellular pertussis vaccine).

Example 1

Production of PVS-RIPO in Cell Culture

Cell Culture

Two vials of the Vero Working Cell Bank cells (Lot 217002-2) were thawed. The contents of each vial were added to 9 mL of warmed complete medium (Dulbecco Modified Eagle Medium, DMEM, Invitrogen) with 10% Fetal Bovine Serum (FBS, Hyclone). A cell count was performed, and the cells were centrifuged at 1000 rpm for 10 minutes at 4° C. All the cells were re-suspended and placed into one 75 cm² flask. The cap of the flask was loosened and placed in the incubator. This was passage 142 (passage 1 after thawing). After two re-feeds, and one week, the cells were trypsinized and re-dispersed in a new 75 cm² flask seeded at 20,000/cm² (passage 143). The cells at this time were at 92% viability.

The 75 cm² flask of cells was scaled-up to two 225 cm² flasks with seeding at 33,280 cells/cm² (passage 144). The cells at this time were 94% viable. Three days later, the cells were 100% viable. Both 225 cm² flasks were pooled together. The final cell densities for several samples, obtained both before and after pooling, ranged from 213,000 to 234,000 cells/cm²' and cell viabilities in the samples ranged from 86% and 96%.

From the culture obtained from the two 225 cm² flasks of cells, three 225 cm² flasks were seeded (passage 145) to scale up to 10 tier CellSTACKs® cell culture chambers, which can be also described as "cell factories" (Corning® Inc., Corning, New York). First, the cells from three 225 cm² were expanded into six 225 cm² flasks. These six flasks of cells (passage 147) were trypsinized and pooled together. From this pool, one five-tier CellSTACK® chamber, one one-tier CellSTACK® chamber, and five 225 cm² flasks were seeded at 39,000 cells/cm² (all were passage 148).

The five tier CellSTACK® chamber (passage 148) was used to seed one ten-tier and four one-tier CellSTACK® chambers at 42,000 cells/cm². The ten-tier CellSTACK® chamber was used for one of the infections. The time from seeding the one ten-tier CellSTACK® chamber to infection was 90 hours. The cells in one of the four one-tier CellSTACKs® chamber were counted to determine how much virus was needed to infect the ten-tier CellSTACK® chamber. The cell count at this point was 332,932 cells/cm$^2$, and the cells were 96% viable. Another one-tier CellSTACK® chamber was used as a control.

The one-tier CellSTACK® (passage 148) made from the initial 225 cm$^2$ flasks was used to make a five-tier Cell-STACK® chamber (passage 149). This five-tier CellSTACK® chamber was then used to seed two ten-tier CellSTACKs® chambers (passage 150) at 42,000 cells/cm$^2$. The time from seeding the two ten-tier CellSTACK® chambers to infection was 94 hours. These two ten-tier CellSTACK® chambers were used for the other two infections.

Infection

An MVB lot was used to infect the production cells. The procedure for production of an PVS-RIPO lot and an MVB lot is summarized as follows: A Vero MCB lot was generated using Vero cells from a World Health Organization Seed. The Vero cells were harvested by trypsinization. Following centrifugation, the cells were resuspended in a cyoprotectant solution of 90% fetal bovine serum (FBS) and 10% dimethyl sulfoxide (DMSO) at a concentration of approximately $1 \times 10^7$ cells/mL. A Vero WCB lot was produced by expansion of the Vero MCB lot as follows: One vial of the Vero MCB lot was used to initiate a Vero WCB. After four passages in DMEM, high glucose with L-glutamine, with Hepes containing FBS, the WCB was vialed at a volume of 1 mL/vial and a concentration of $4.7 \times 10^6$ cells/mL. Vials containing the Vero Master WCB lot were placed into vapor phase liquid nitrogen. The PVS-RIPO plasmid DNA lot was used to produce a PVS-RIPO RNA lot by in vitro transcription. Forty (40) µg of the PVS-RIPO plasmid DNA lot was linearized by Sal I digestion. The linearized DNA was extracted with phenol and chloroform, and an ethanol precipitation was performed at $\leq -70°$ C. overnight. The DNA was resuspended in 40 uL of DNase/RNase-free distilled water. A sample of the plasmid DNA before digestion/purification and after digestion/purification was analyzed by agarose gel electrophoresis to confirm the product size and recovery.

Twenty (20) µg of the linearized DNA was used as the template to synthesize the PVS-RIPO RNA in two identical reactions. Each reaction was performed using 10 µg of linearized DNA. To set up the reactions, 10 µg of linearized plasmid DNA was added to the in vitro transcription reaction mix (RiboMAX Large Scale RNA Production System, Promega) to a final volume of 100 µl. The transcription reactions were incubated at 37° C. for 2.5-3 hours. When the reactions were complete, the reaction tubes were placed at $\leq -70°$ C. for storage. Vero cells from a qualified working cell bank (WCB) were used in the electroporation step. Two vials of a Vero cell WCB lot were expanded in DMEM with L-glutamine, without Phenol Red, enriched with 10% FBS and incubated at 37° C. and 5% $CO_2$ for three passages.

The Vero cells were trypsinized by adding trypsin-EDTA (0.05% trypsin, 0.5 mM EDTA) and incubated at 37° C. and 5% $CO_2$ for 4-6 minutes. The trypsinized cells were collected and centrifuged at approximately 4° C. and 1000 RPM for 10 minutes. The collected cells were suspended in 100±2 mL PBS (without calcium and magnesium). A sample of the cell suspension was used to determine the cell count. The remaining cells were collected by centrifugation at a setting of 1000 RPM and 4° C. for 10 minutes. The clarified PBS was removed and the cell pellet resuspended in fresh PBS to a final calculated cell density of $1.25 \times 10^7$ cells/mL. Approximately 55 µg of PVS-RIPO RNA and 9 mL of the expanded Vero cells were combined and transferred into cuvettes in 0.8 mL aliquots. The contents of the cuvettes were subjected to two electrical shocks at 0.5 kilovolts and 0.25 microFarads using a Bio-Rad Gene Pulser II electroporation unit. After incubation at room temperature for 15 to 20 minutes, the cuvette contents were transferred to T75 flasks with DMEM/F12 media (Invitrogen). The T75 flasks were incubated at 33° C. and 5% $CO_2$. Complete cytopathic effects were observed on the third day of incubation.

The contents of the flask was harvested and clarified by centrifugation to yield the initial virus seed (IVS) lot. Vero cell expansion was as follows: Vero cells were seeded into two T25 flasks containing DMEM, with L-glutamine, without phenol red (DMEM, Invitrogen) with 10% FBS (Hyclone) and incubated in a $CO_2$ incubator at 37° C. and 5% $CO_2$. The Vero cells were further expanded to fifty T162 flasks after passaging the cells three times. On day three of the third passage, the contents of the fifty T162 flasks were examined under a microscope to determine the condition of the cells. Forty-three flasks were selected that were pure cultures and at least 95% confluent. The cells in one of the selected T162 flasks were examined to determine the cell number and viability and another flask incubated as the cell quality control flask. Of the remaining 41 flasks, one was maintained as a negative control after inoculation with DMEM:Nutrient Mixture F12 1:1 Mixture without phenol red (DMEM/F-12, Invitrogen). The PVS-RIPO Post-Electroporation Seed lot was removed from storage, thawed at room temperature and diluted using DMEM/F-12 medium. The forty T162 flasks (containing the expanded Vero cells) were infected with the PVS-RIPO post-electroporation seed lot at a multiplicity of infection (MOI) of 0.5. The inoculated flasks were incubated at 33° C. and 5% $CO_2$ after the addition of fresh DMEM/F-12 cell culture medium. Virus infected flasks and control flasks were monitored during incubation for attributes such as visible contamination, the condition of cells and percent confluency.

At 70 hours post-infection, incubation was terminated and the flasks were examined for attributes such as visible contamination, cell condition and percent confluency and then harvested. The contents of the flasks were transferred into centrifuge bottles and centrifuged at 4° C. and 2500 RPM for 33 minutes to clear cell debris. Supernatants containing the PVS-RIPO virus were pooled into an 850 cm$^2$ roller bottle. The pooled supernatants were transferred into two 30 mL and twenty-four 125 mL PETG bottles in 20 mL and 80 mL aliquots, respectively. Additionally, twelve 2 mL cryovials were filled with 1 mL aliquots. The remaining supernatant (3.8 mL total) was transferred into three 2 mL cryovials for a total of fifteen 2 mL cryovials labelled as PVS-RIPO Master Virus Seed lot. Eleven 2 mL cryovials, twenty-three 125 mL PETG bottles and two 30 mL PETG bottles were frozen at $\leq -70°$ C. and subsequently transferred to $\leq -70°$ C. controlled storage. Four of the 2 mL cryovials were submitted to process analytics/biopharmaceutical quality control for titer (by pfu and $TCID_{50}$), virus particle, and DNA sequence release testing. The remainder of the release testing was performed as appropriate and PVS-RIPO material handling procedures were developed.

The three ten-tier CellSTACK® chambers with cell culture produced in the previous section were washed with Dulbecco's Phosphate Buffered Saline (DPBS, Invitrogen) and then infected with multiplicity of infection (MOI) of 0.1 in DMEM/F-12 (Invitrogen). One 80 mL aliquot of the P1 Master Viral Bank (Lot #L0403006) was thawed and 21 mL aliquots were used to infect each ten-tier cell chamber at 33° C. for 72 hours in 5% $CO_2$ incubator. The ten-tier cell factories were harvested 70 hours post-infection, after confirming 100% cytopathic effect (CPE) visually using a microscope. Harvested material was centrifuged at 3,800 rpm at 4° C. for 20 minutes. The supernatant was processed immediately (Lot #L1308002B, see Table 3) or stored at −70° C. for up to nine days (Lot #L1308002C and L1308002D, see Table 3) prior to purification.

Example 2

Purification of PVS-RIPO

Harvests from each of three ten-tier CellSTACK® chambers were purified according to the protocol schematically illustrated in FIG. 5, namely, nuclease treatment, followed by gel filtration chromatography, followed by qPCR analysis, followed by anion exchange chromatography, followed by concentration via diafiltration. The purification protocol was repeated for each of the three production runs.

Nuclease Treatment

Benzonase® enzyme (Sigma-Aldrich, Saint Louis, Mo.) is an endonuclease that digests both free RNA and DNA in solution. Fully encapsulated viral nucleic acids (i.e., contained in intact viral particles) are not affected. Benzonase® enzyme is needed to reduce and/or remove 1) host cell DNA (gDNA, mtDNA) and RNA (tRNA, rRNA); 2) other potential contaminating DNA/RNA (ex. endogenous/exogenous viruses) if present; and 3) unencapsulated free viral RNA. Removal of free nucleic acids is needed for reasons of safety, reducing harvest viscosity, and improving the signal to noise ratio of downstream viral detection methods such as A254 nm and RT-qPCR. The performance of Benzonase® enzyme is contingent on the buffer solution in which it is contained.

100 mM magnesium chloride ($MgCl_2$) was added to each of the three clarified harvests to obtain a final concentration of 1 mM $MgCl_2$ prior to the Benzonase® enzyme addition. Additions of Benzonase® enzyme were based on the volume of the harvest to achieve the final Benzonase® enzyme concentration in each harvest of 50 μg/ml. Each harvest bottle was then incubated at 2-8° C. for 16-24 hours.

Gel Filtration Chromatography

A 10 cm (internal diameter (i.d.)) BPG column (GE Healthcare-Biosciences, Pittsburgh, Pa.) was packed with 3140 mL of Sepharose 6 Fast Flow (FF) resin (GE Healthcare-Biosciences) to a bed height of 40 cm. Prior to use, the packed column was sanitized with 0.5N NaOH and allowed to sit for 26-28 hours at ambient temperature. Water was used to flush the column, and the column was stored in 0.05M NaOH until the purification process. Prior to purification, the column was flushed with 5M NaCl and allowed to sit in 5M NaCl solution for 24 hours prior to the start of the purification process. The column was then charged with two column volumes of 4.7 mM $Na_2HPO_4$, 1M NaCl pH 7.5 and equilibrated with three column volumes of 4.7 mM $Na_2HPO_4$, 42 mM NaCl, pH 7.5, at a flow rate of 50 mL/min.

For each of the three purifications, the Benzonase® enzyme-treated harvest was applied in a one-column injection, 25% column volume, at 30 cm/hr. The column was eluted using 4.7 mM $Na_2HPO_4$, 42 mM NaCl, pH 7.5, buffer. The absorbance of the eluate was monitored continuously using three wavelengths (280/215/254 nm), and conductivity was also measured continuously. The eluted fractions from each Sepharose 6 FF chromatography column step were collected in volumes of 150-200 mL. Selected fractions from all three runs were analyzed by real time RT-qPCR (see Example 3) and pooled based on the PVS-RIPO copy number (>$1\times10^7$ copies/mL) from the real time RT-qPCR analysis. Pooled material was then purified in the second chromatography step.

Anion Exchange Chromatography

A 2.6 cm (i.d.) XK column was packed with 53 mL of Super Q 650M resin (Toyopearl®, Tosoh Bioscience, Tessenderlo, Belgium) to a final bed height of 10 cm. The packed column was sanitized with 0.5N NaOH and allowed to sit at ambient temperature for one hour. The packed column was flushed with water to remove NaOH, the column was then flushed with 5M NaCl and allowed to sit in 5M NaCl solution for 24 hours.

The column was then charged with 4.7 mM $Na_2HPO_4$, 1M NaCl, pH 7.5, and equilibrated with of 4.7 mM $Na_2HPO_4$, 42 mM NaCl, pH 7.5, at a flow rate of 10 mL/min. For each of the three purifications, the Sepharose 6 FF pooled fractions were applied in a single column injection. The column was eluted using 4.7 mM $Na_2HPO_4$, 42 mM NaCl, pH 7.5, buffer. The absorbance of the eluate was monitored continuously using three wavelengths (280/215/254 nm) and conductivity was also monitored continuously. The main peak collected was the flow through peak; the contaminants bound to the column. After the collection of the main peak, the column was striped using 4.7 mM $Na_2HPO_4$, 1M NaCl pH 7.5 and the strip peak was collected in a secondary container and, in one instance, analyzed by SDS-PAGE.

Concentration/Diafiltration

The flow-through peak collected after Super Q 650M column was then concentrated to approximately 50 mL and diafiltered with 500 mL of 50 mM $Na_2HPO_4$, 150 mM NaCl, pH 7.4. In each concentration step, the tangential flow filtration (TFF) filters were flushed with 2×25 mL of 50 mM $Na_2HPO_4$, 150 mM NaCl, pH 7.4. The permeate was collected and, in one instance, analyzed by SDS-PAGE. Flushes and concentrated purified PVS-RIPO were pooled together and 20% Human Serum Albumin (HSA) (Baxter Pharmaceuticals, Deerfield, Ill.) was added to purified PVS-RIPO to a final formulation of 50 mM $Na_2HPO_4$, 150 mM NaCl, pH 7.4, 0.2% HSA.

Pooling and Vialing

The three lots of PVS-RIPO final formulated were pooled together and sterile filtered using a 0.2 μm Millipak® 20 filter. The sterile filtered material was then dispensed into 3 mL glass vials at a volume of 0.5 mL. The vials were stored at −70° C.

Example 3

Analysis of Purified PVS-RIPO

Selected fractions from gel-filtration and chromatography steps were tested in the plaque assay (NIH, National Cancer Institute-Frederick, Biopharmaceutical Development Program (BDP) Standard Operating Procedure (SOP) 22163 Plaque Assay for Poliovirus). $TCID_{50}$ (BDP SOP 22165 $TCID_{50}$ Assay for Poliovirus using Hep-2C Cells) was performed at the end of each of the three purification runs on the final bulk material prior to pooling. Fractions from Sepharose 6 Fast Flow Chromatography were assayed by real time qPCR (BDP SOP 22195 Quantitative PCR (qPCR) Methods for Detection and Quantification of Nucleic Acids) to monitor PVS-RIPO.

Sepharose 6 FF fractions were tested for total PVS-RIPO viral RNA using a TaqMan®-based RT-qPCR (Applied Biosystems® Inc., Foster City, Calif.) amplicon targeting the HRV-2 IRES region in PVS-RIPO. Fraction samples were extracted using a Qiagen® (Valencia, CAQ) Viral RNA mini-prep kit prior to the real time RT-qPCR amplification. TaqMan® primers and a dual fluorescent dye-labeled probe were designed with ABI Primer Express software (Applied Biosystems Inc.). The 71-bp HRV-2 IRES (PVS1) amplicon consisted of a forward primer: 5'-(AAC CCA ATG TGT ATC TAG TCG TAA TGA) (SEQ ID NO: 1); reverse primer: 5'-(TGA AAC ACG GAC ACC CAA AG) (SEQ ID NO: 2); and TaqMan® probe: 5'-[6FAM]-(CAA TTG CGG GAT GGG ACC AAC T)-[TAMRA] (SEQ ID NO:3). Primers and probes were diluted to 10 and 5 pmol/μl, respectively, with nuclease free water (NFW). The reaction consisted of 25 μl TaqMan® 1-step RT-PCR 2× Master Mix with ROX dye, 1 μl RNase inhibitor, 1 μl NFW, 1 μl forward primer, 1 μl reverse primer, 1 μl TaqMan® probe and 20 μL of sample for a 50 μl final reaction volume. (1-step RT-PCR 2× Master Mix with ROX dye" is commercially available from Applied Biosystems Inc.) Reaction mixtures were loaded into a 96-well plate, covered with optical film, and amplified with an ABI model 7900HT 96-well Sequence Detection System (Applied Biosystems Inc.) using a 5-step qPCR profile (2:00 min, 50.0° C.; 45 min at 60.0° C. (RT-step); 5:00 min, 95.0° C.; 45 cycles of 20 sec, 94.0° C.; 1:00 min, 62.0° C.). Amplicon cDNA standard curves for quantitation were made from PVS-RIPO plasmid DNA, and were 10-fold serial-diluted into NFW from 1 ng to 1 fg per reaction. PCR inhibition, extraction, buffer/NTC, and reverse transcription controls were employed in each assay.

The purifications products from each of the three purification runs demonstrated consistent results. Table 3 shows the purification yields. Overall PVS-RIPO yield was at or above 60%. The detected recovery variability was likely partially due to the variation of the plaque assay. Consequently, critical stages of the process had samples analyzed by an end point dilution assay. The results of the final formulated purified bulk from this assay were $5.83 \times 10^{11}$, $3.77 \times 10^{11}$, and $2.98 \times 10^{11}$ TCID$_{50}$ respectively. These results show constant yield and concentration across the three purifications.

Figure 6:
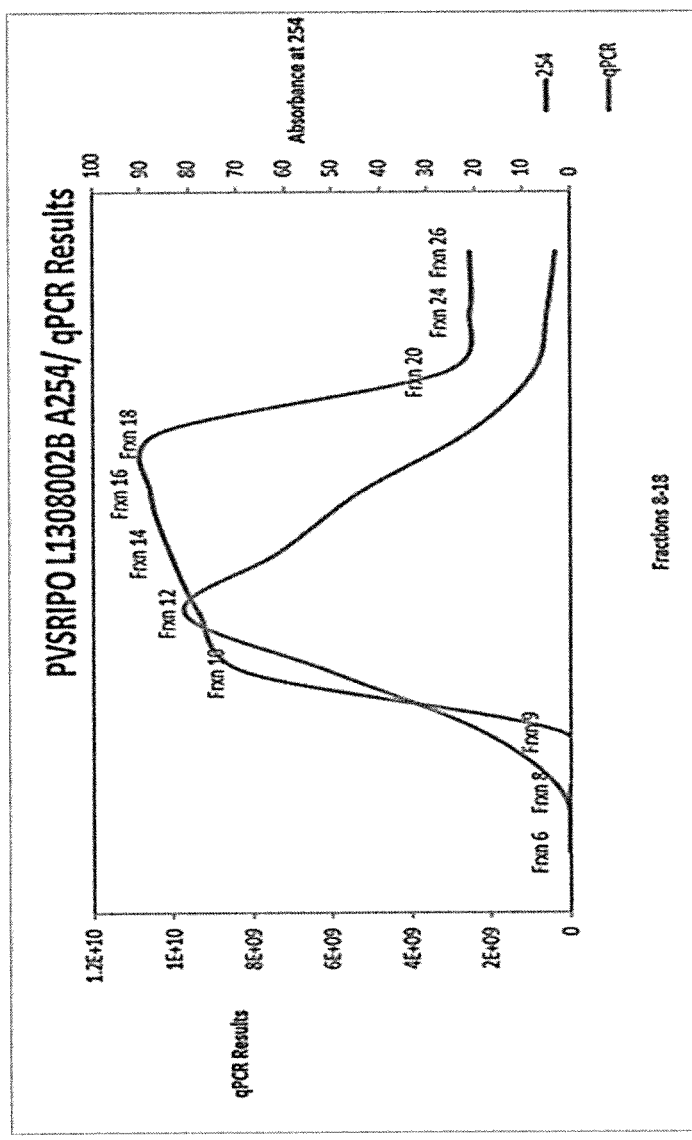

Comparison of the chromatographic profiles from the Sepharose 6 FF column and the Super Q 650M column from the three purification runs showed consistency of purification at both gel filtration and anion exchange chromatography steps. Sepharose 6FF chromatograms contained two defined peaks. Fraction analysis by real time RT-qPCR indicated that the PVS-RIPO main peak was located within the small initial peak, as illustrated in FIG. 6. The large peak immediately following this appeared to be residual salt. When monitored specifically at a wavelength of 254 nm, a comparative overlay of optically monitored chromatogram and real time RT-qPCR results showed that some of the PVS-RIPO-containing fractions did not appear within the optically-detected peak. The real time RT-qPCR results were therefore critical for ascertaining which fractions contained PVS-RIPO (the cutoff of $>10^7$ copies/mL was employed) and should be pooled for further processing. The SuperQ 650M chromatograms displayed one large flow-through peak. In SuperQ 650M purification step, some of extraneous contaminants in a flow through process. Immediately following the main peak collection, a large peak appeared when the column was stripped with 4.7 Mm Na$_2$HPO$_4$, 1M NaCl pH 7.5 buffer. In an effort to confirm that PVS-RIPO material was not lost throughout the process, SDS-PAGE analysis was performed on a sample collected from this peak as well as a sample of the permeate from the concentration step. Both assays indicated that the PVS-RIPO was not present in either sample.

During the final concentration/diafiltration process, the appearance of the virus changed from translucent to opalescent, as it became more concentrated. All three final concentrated samples exhibited the same appearance. When they were pooled together and filtered, the appearance changed from opalescent to a clear/translucent product. TCID$_{50}$ 1.4× of $10^{12}$ before filtration and $2.4 \times 10^{12}$ after filtration indicated that there was no loss of product from the filtration process. The final concentration of PVS-RIPO product prior to portioning in the vials was determined to be $6.09 \times 10^9$ TCID$_{50}$/mL.

TABLE 3

Summary of the purification results.

| Purification Steps | Titer (Pfu/mL) | Volume (mL) | Total Pfu's | % Step Recovery | % Overall Recovery |
|---|---|---|---|---|---|
| 1 × 10 Tier Cell factory, 750 mL per cell factory L1308002B Processed immediately after Harvesting ||||||
| Harvest Benzonase ® | $4 \times 10^8$ | 728 | $2.912 \times 10^{11}$ | | |
| Sepharose 6FF Main Peak | $1.1 \times 10^8$ | 1565 | $1.72 \times 10^{11}$ | 59% | 59% |
| Sepharose Q650M Main Peak | $8 \times 10^7$ | 2005 | $1.6 \times 10^{11}$ | 93% | 55% |
| Formulated w/0.2% human serum albumin (HSA) - final purified bulk | $1.4 \times 10^9$ (Pfu/mL) $4.7 \times 10^9$ TCID$_{50}$/ml | 124 | $1.74 \times 10^{11}$ Pfu $5.83 \times 10^{11}$ TCID$_{50}$ | 109% | 60% |
| 1 × 10 Tier Cell factory, 750 mL per cell factory L1308002C Processed after storage at −70° C. ||||||
| Harvest Benzonase ® | $1.0 \times 10^8$ | 734 | $7.34 \times 10^{10}$ | | |
| Sepharose 6FF Main Peak | $4.17 \times 10^8$ | 1762 | $7.35 \times 10^{10}$ | 100% | 100% |
| Q650M Main Peak | $5.3 \times 10^7$ | 2075 | $1.075 \times 10^{11}$ | 146% | 146% |

TABLE 3-continued

Summary of the purification results.

| | | | | | |
|---|---|---|---|---|---|
| Formulated w/0.2% HSA | 1.4 × 10$^9$ (Pfu/mL) 2.8 × 10$^9$ TCID$_{50}$/ml | 135 | 1.89 × 10$^{11}$ PFU 3.77 × 10$^{11}$ TCID$_{50}$ | 56% | 83% |

1 × 10 Tier Cell factory, 750 mL per cell factory L1308002D
Processed after storage at −70° C.

| | | | | | |
|---|---|---|---|---|---|
| Harvest Benzonase® | 2.96 × 10$^8$ | 762734 | 7.25 × 10$^{11}$ | | |
| Sepharose 6FF Main Peak | 1.22 × 10$^8$ | 1957 | 2.39 × 10$^{11}$ | 106% | 106% |
| Sepharose Q650M Main Peak | 7.17 × 10$^7$ | 2568 | 1.84 × 10$^{11}$ | 77% | 82% |
| Formulated w/0.2% HSA | 1.12 × 10$^9$ (Pfu/mL) 2.35 × 10$^9$ TCID$_{50}$/ml | 127 | 1.42 × 10$^{11}$ Pfu 2.98 × 10$^{11}$ TCID$_{50}$ | 56% | 83% |

Combined Three Purification Lots Lot # L1310001

| | Titer (Pfu/mL) | Volume (mL) | Total Pfu's | Titer (TCID$_{50}$/mL) | Total TCID$_{50}$ |
|---|---|---|---|---|---|
| Purified Bulk | 1.92 × 10$^9$ | 385.0 | 7.40 × 10$^{11}$ | 3.62 × 10$^9$ | 1.39 × 10$^{12}$ |
| Filtered Purified Bulk | 1.42 × 10$^9$ | 396.5 | 5.63 × 10$^{11}$ | 6.09 × 10$^9$ | 2.41 × 10$^{12}$ |

Example 4

Purification of a Vaccine Composition

Purification of herpes simplex virus (HSV-1) for clinical use utilizes Benzonase® enzyme treatment followed by Q-Sepharose XL and Sepharose 4FF chromatography. Sterile filtration is not employed due to the size of the HSV capsid. The issues are the same as with PVS-RIPO in that the location of viral fraction versus host cell DNA/RNA or proteins is not immediately apparent by column A280 or A260 measurements. Thus, qPCR can be used as described herein to aid the in identification of HSV-1-containing fractions. As an alternative to real-time RT-qPCR, a surface plasmin resonance (BIAcore) or surface interferometry (Octet) approach may be used to quantitate HSV-1 capsid epitope (binding) densities on the BIAcore chip or Octet sensor. Thus uniquely identifying the location and quantities of the virus in the column fractions.

Example 5

Chemistry, Manufacturing, and Control Information for Non-Pathogenic Oncolytic Poliovirus Chimeras (PVSRIPO) Final Vialed Product Lot L0904010

Figure 7:
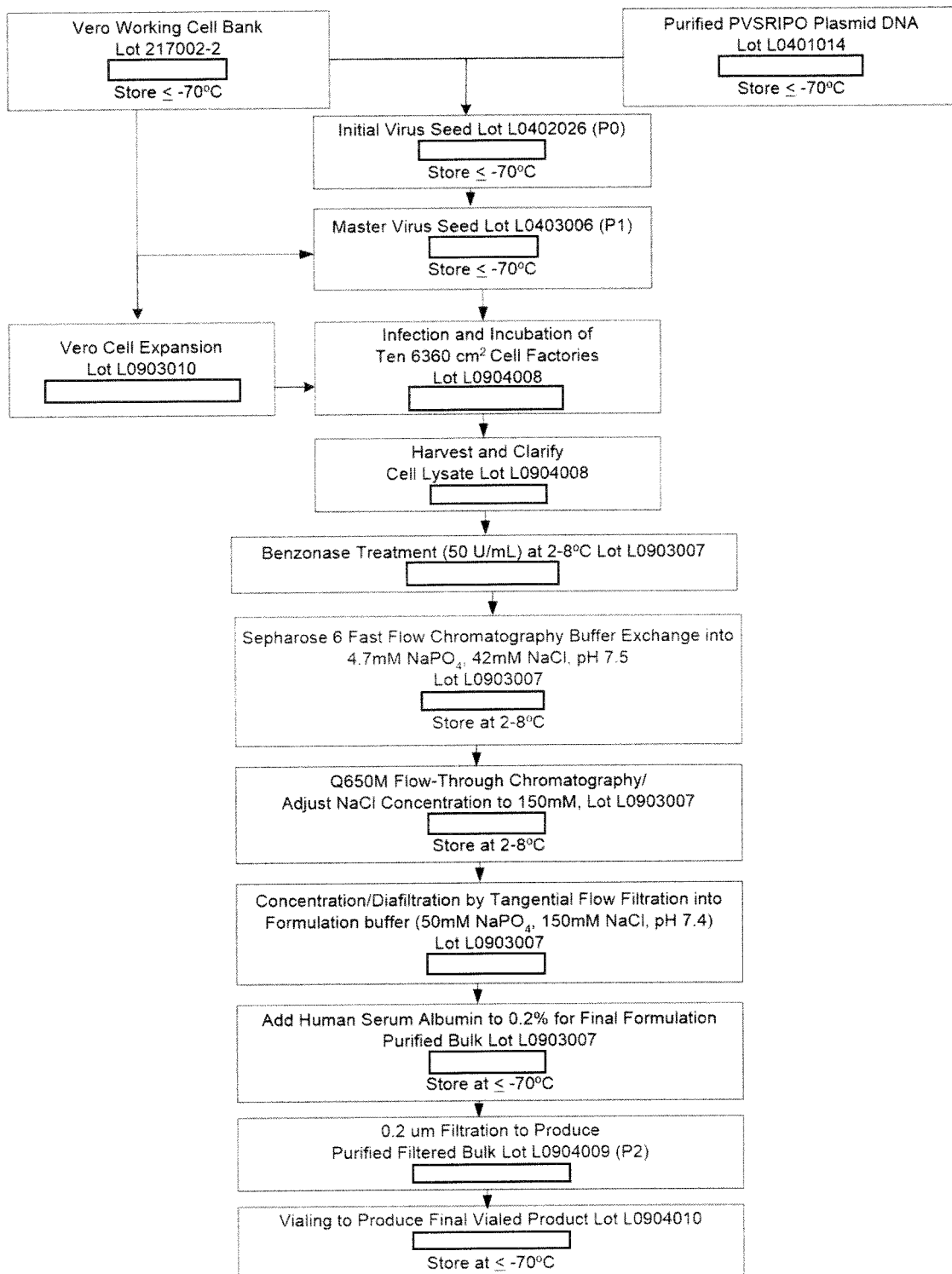
FIG. 7 is a flow chart providing an overview of the production of PVSRIPO final vialed Product Lot L0904010.

This example describes methods used to produce PVS-RIPO lot L0904010 for use in glioblastoma therapy. A summary is provided in FIG. 7. Briefly, purified PVS-RIPO plasmid DNA Lot L0401014 was transcribed to produce PVS-RIPO RNA. The PVS-RIPO RNA was then electroporated into qualified Vero cells and expanded to produce the initial viral seed Lot L0402026 (P0). The initial viral seed Lot L0402026 was expanded in qualified Vero cells to produce the Master Viral Seed Lot L0403006 (P1). The Master Viral Seed Lot L0403006 was expanded and purified to produce the Purified Filtered Bulk Lot L0904009 (P2). The Purified Filtered Bulk Lot L0904009 was filled to produce the FVP Lot L0904010. The resulting concentrated purified virus was formulated in 50 mM sodium phosphate in 0.9% sodium chloride, pH 7.4+0.2% human serum albumin, and sterile filtered.

Full length sequencing was performed for PVSRIPO-kan/pUC19 plasmid DNA sequence (Lot L0401014). Lot L0401014 was produced and purified under current Good Manufacturing Practices (CGMPs) and was further used to produce the Master Virus Seed Lot L0403006 and subsequently the PVS-RIPO Purified Sterile Bulk Lot L0904009 and Final Vialed Product Lot L0904010. The sequence was found to be 100% homologous to PVS-RIPO plasmid reference sequence Lot L0305007. A BLASTn search conducted on the plasmid DNA indicated that no oncogenic, toxin, or unexpected viral sequences were present.

Sequencing of the PVS-RIPO genome sequence was also performed using material from the Master Virus Seed Lot L0403006, the Purified Sterile Bulk Lot L0904009, and the Final Vialed Product Lot L0904010 and confirmed 100% homology to the PVS-RIPO reference sequence Lot L0401014.

Materials

Raw materials of animal origin used in the manufacture of PVSRIPO include Benzonase®, Fetal Bovine Serum (FBS), Human Serum Albumin, and Trypsin-EDTA. Raw material manufacturers supplied documentation indicating that:

(1) The Benzonase® enzyme preparation was produced recombinantly by microbial fermentation using casamino acids from bovine milk in the fermentation growth medium. The milk is sourced from countries with no recorded BSE cases in locally bred animals since 1990 and is considered fit for human consumption.

(2) The FBS was manufactured from fetal bovine blood collected in USDA inspected abattoirs located in the United States and was negative for bovine viruses tested.

(3) The HSA was from Baxter Healthcare Corporation, a facility licensed by the US FDA to manufacture and prepare plasma derivatives for sale for use in humans. Plasma was collected in the USA exclusively from US donors and in accordance with applicable US FDA regulations.

(4) The trypsin was of porcine origin and sourced from the United States/Canada. The raw trypsin was tested and found negative for porcine parvovirus and was irradiated prior to formulation.

Genetic Constructs a. PVSRIPO Plasmid

Figure 8:
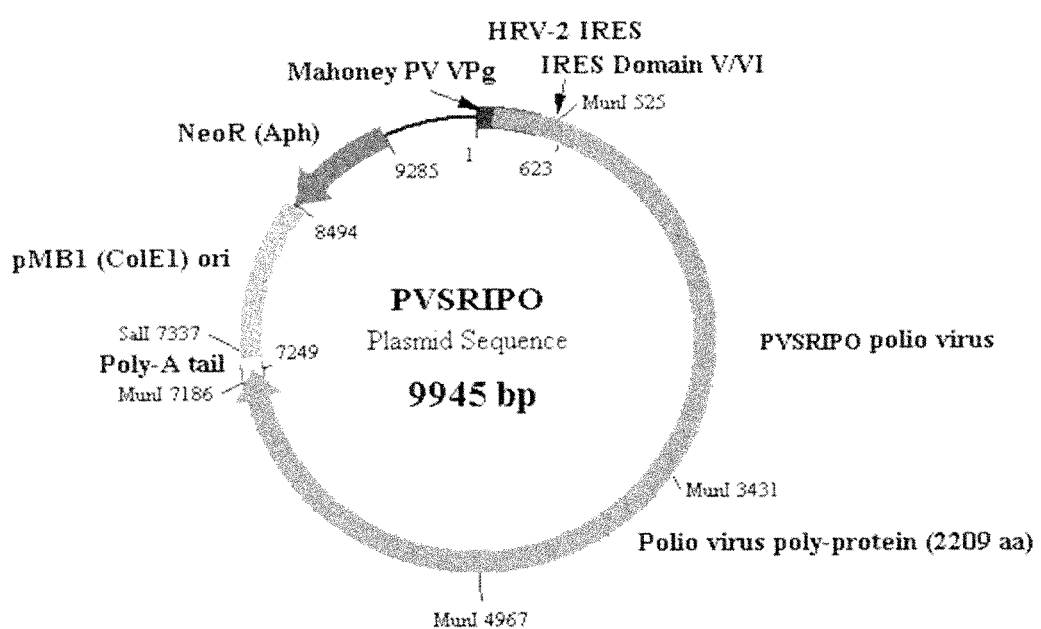
FIG. 8 is a map of PVSRIPO (PVSRIPO-kan/pUC 19) plasmid DNA.

The recombinant PVSRIPO DNA (7.7 kb) was cloned into a modified pUC19 vector (carrying the kanamycin resistance gene instead of the ampicillin resistance gene), and then transformed in the E. coli DH5α competent cells to amplify the plasmid DNA. The PVSRIPO-kan/pUC 19 plasmid map is shown in FIG. 8.

b. PVS-RIPO Virus Genome

The PVS-RIPO virus genome consists of a 5' non-translated region (5'-NTR), a PVS-RIPO open reading frame (ORF), and a 3' non-translated region (3'-NTR). The 5'-NTR contains human rhinovirus type 2 internal ribosomal entry site (HRV-IRES). The PVS-RIPO open reading frame encodes a single protein, which is proteolytically processed into the virus structural protein (P1) and non-structural proteins (P2 and P3). P1, P2 and P3 will be processed further. The PVS-RIPO genome is the same as attenuated poliovirus type I Sabin strain except for the HRV-IRES region. The genotype of PVS-RIPO is 5'-cloverleaf [PV1 (M); Genbank® Accession No. NC_002058; nt 1-109]—cleavage site for restriction endonuclease EcoRI-IRES [HRV2; Genbank® Accession No. XO2316; nt 105-610]—open reading frame [PV1(S); Genbank® Accession No. V01150; nt 743-7369; nt 748 (t to a)]—3'UTR [PV1(S); nt 7370-7441]—poly(A).

PVSRIPO Plasmid DNA Production

Figure 9:
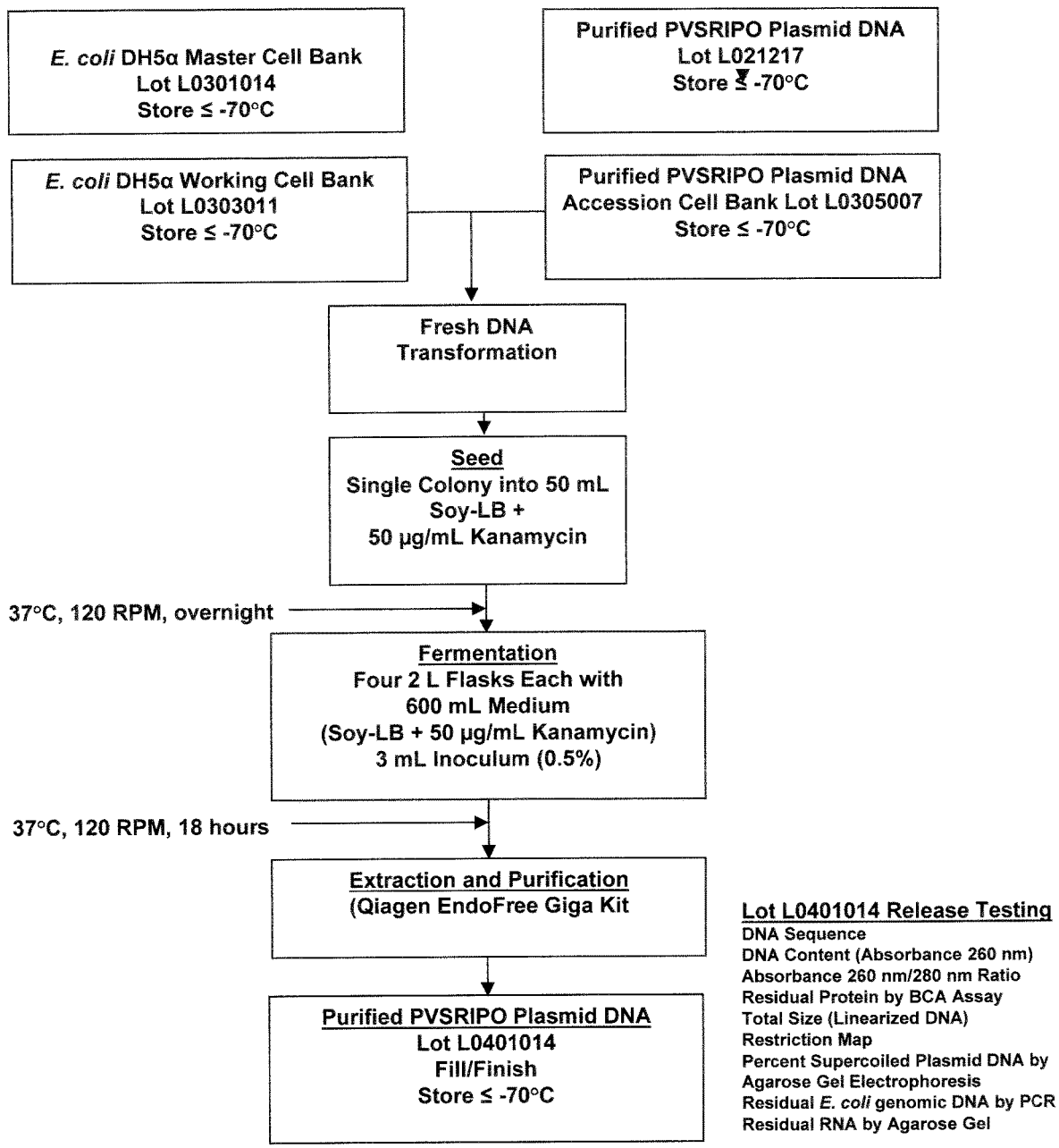
FIG. 9 is a process flowchart showing PVSRIPO Plasmid DNA Lot L0401014 Production.

The Lot L0401014 PVSRIPO plasmid DNA production process is illustrated in FIG. 9.

a. Description and Testing of the Host Cell System

The host cell system, E. coli DH5a, was obtained from Invitrogen and then qualified and expanded at the BDP to produce the E. coli DH5α Master Cell Bank (MCB) Lot L0301014, and subsequently the E. coli DH5α Working Cell Bank (WCB) Lot L0303011.

The E. coli DH5α MCB Lot L0301014 was produced by expansion of one vial (approximately 1 mL) of Invitrogen E. coli DH5α Lot 1159251 in three 500 mL flasks each containing 150 mL sterile, prepared culture medium (sodium chloride 10 g/mL, soytone 10 g/mL, and yeast extract 5 g/mL). The frozen vial was thawed in a 37±1° C. incubator for five minutes. The inoculated culture medium was incubated at 37±1° C. and 150±10 rpm for approximately 18 hours. A glycerol solution was combined with the contents of Flask 1 (OD600=4.31) to a final glycerol concentration of 20%. The cell suspension was vialed at 1.0±0.2 mL/vial yielding 144 filled vials. The filled vials were frozen to ≤−70° C. using a controlled-rate freeze and placed into controlled storage at −70° C. The specifications and release test results for the E. coli DH5 α MCB Lot L0301014 are provided in the Certificate of Analysis in FIG. 10.

The E. coli DH5α WCB Lot L0303011 was produced by expansion of two vials (approximate total in the two vials=2 mL) of E. coli DH5α MCB Lot L0301014 in three 125 mL first stage seed flasks (inoculum volume approximately 400 μL) each containing 40 mL sterile, prepared culture medium (sodium chloride 10 g/mL, soytone 10 g/mL, yeast extract 5 g/mL, and magnesium sulfate heptahydrate 5 g/mL) and then in two two-liter second stage seed flasks (inoculum volume approximately 4 mL) each containing 390 mL of the same sterile, prepared culture medium. The frozen vials were thawed in a 37±1° C. incubator for five minutes. The inoculated cultures were incubated at 37±1° C. and at a speed setting of 235 rpm. The first stage seed flasks were incubated overnight (for approximately 16 hours) to an OD600=2.5, and the second stage seed flasks were incubated approximately 2.6 hours to an OD600=0.361. The contents of second stage seed flask 1 was centrifuged at the following settings for seven minutes: 1600×g and 4° C. The cell pellet was resuspended in a 100 mM calcium chloride/15% v/v glycerol solution and centrifuged at the following settings for five minutes: 1100×g and 4° C. The resulting cell pellet was resuspended in a 100 mM calcium chloride/15% v/v glycerol solution (for a final glycerol concentration of 15%) and vialed at a volume of 0.15 mL/vial yielding 95 filled vials. The filled vials were frozen in a dry ice/ethanol bath and placed into controlled storage at −70° C. The specifications and release test results for the E. coli DH5α WCB Lot L0303011 are provided in the Certificate of Analysis in FIG. 11.

b. Purification of Original PVS-RIPO Plasmid DNA to Produce Purified PVS-RIPO Plasmid DNA Lot L021217

The original PVS-RIPO plasmid DNA was provided by the Duke University Medical School. This material was used to generate additional plasmid DNA that was purified. Ten microliters (μL) of the original PVS-RIPO plasmid DNA was transformed into E. coli DH5α competent cells (Invitrogen Catalog Number 18263-012). Plasmid DNA extracted from the resulting eighteen transformants using Plasmid Mini and Maxi Kits (Qiagen Catalog Numbers 27104 and 12165 respectively) and the original PVS-RIPO plasmid DNA received from Duke University Medical School were analyzed by agarose gel electrophoresis and restriction enzyme digestion. Results of the analyses demonstrated that multiple bands were observed ranging from 2.5 kb to 10.3 kb. Ten of the transformants were selected for further investigation. Based on restriction enzyme digestion analysis, DNA from one of the transformants identified as S-1 was sequenced and found to have a 1.3 kilobase (Kb) insertion that was determined via BLASTn to be the bacterial minitransposon IS10R. Other colonies appeared as either an empty vector (approximately 2.5 kb), a dimer vector (approximately 5.0 kb), or PVSRIPO Plasmid DNA (approximately 10 kb).

Agarose gel electrophoresis was used to further analyze the banding pattern of the original PVS-RIPO plasmid DNA received from Duke University Medical School. Eight bands were excised from the gel then purified using MiniElute Gel Extraction Kit (Qiagen Cat #27104), and stored at −20° C. The purified DNA from each of the eight bands was transformed into DH5α competent cells, and selected transformants were grown at 37° C. overnight in liquid Soy-LB medium supplemented with 50 μg/mL kanamycin. The DNA, purified using QIAprep Spin Mini kit (Qiagen Cat #27106), was analyzed by agarose gel electrophoresis and restriction enzyme digestion. Two clones, identified as #6-3 (from band #6 transformation) and #5-3 (from band #5 transformation), appeared to possess the correct plasmid size and were selected for further investigation.

The two clones, #6-3 and #5-3, were each expanded in Soy-LB medium containing 50 μg/mL kanamycin at 37° C. and 120 Revolutions per Minute (RPM), and the cells collected. QIAfilter plasmid Mega Kit (Qiagen Cat #12281) was used for DNA purification. Restriction digest analysis indicated that the purified plasmid DNA from each of the two clones had the correct restriction pattern and the 1.3 Kb insert was absent. The lot expanded from clone #6-3 was assigned lot number L021217 and the purified Lot L021217 DNA was sequenced. The resulting sequence was found to be 100% homologous to the expected correct sequence. Lot L021217 was frozen at ≤−70° C. in 1 mL aliquots.

c. Purified PVS-RIPO Plasmid DNA Accession Bank Lot L0305007 Production and Testing The purified PVS-RIPO plasmid DNA Lot L0305007 Accession Bank was produced from purified PVS-RIPO Plasmid DNA Lot L021217. Two vials of purified plasmid DNA Lot L0212017 and six vials of DH5α competent working cell bank Lot L030301 were withdrawn from controlled storage at ≤−70° C. and thawed on cool packs (0 to −20° C.). The contents of the six thawed DH5a competent working cell bank Lot L0303011 vials were combined and 100 μL were aliquotted into each of three chilled tubes. Purified DNA Lot L021017 was diluted 5-fold in endotoxin-free 10 mM Tris-HCl, 1 mM EDTA, pH 8.0. One microliter of the diluted DNA Lot L021217 was added to two of the chilled tubes and the third tube was used as a negative control. The three tubes were sealed and incubated for approximately 30 minutes on cool packs. The three tubes were then heat shocked by placing them in a 40±2° C. water bath for approximately 42 seconds. The tubes were allowed to cool on cool packs for approximately 4 minutes. Working in a Biological Safety Cabinet (BSC), approximately 900 μL of Soytone-LB medium (refer to Table 4 for Soy-LB Medium formulation) were added to each of the three tubes and the tubes were incubated at a setting of 37° C. and 120 RPM for approximately one hour. Aliquots (100, 200 and 400 μL) from the each of the two tubes containing the plasmid preparation solutions were uniformly distributed onto Soytone-LB+50 μg/mL Kanamycin agar plate (refer to Table 5 for Soy-LB Agar Plate formulation) for a total of six plates. The contents of the negative control tube (200 μL) were uniformly distributed onto a Soytone-LB+50 μg/mL Kanamycin agar plate. The seven plates were incubated overnight at a setting of 37° C.

TABLE 4

| Soy-LB Medium Formulation | | |
|---|---|---|
| Components | Manufacturer and Catalog Number | Amount per Liter |
| Soytone | Difco SE50MAF | 10.0 g |
| Sodium Chloride | J. T. Baker 3629-07 | 10.0 g |
| Yeast Extract | Difco 0127-08 | 5.0 g |

TABLE 5

| Soy-LB Agar Plate Formulation | | |
|---|---|---|
| Components | Manufacturer and Catalog Number | Amount per Liter |
| Soytone | Difco SE50MAF | 10.0 g |
| Sodium Chloride | J. T. Baker 3629-07 | 10.0 g |
| Yeast Extract | Difco 0127-08 | 5.0 g |
| Agar | Difco 214530 | 15.0 g |

Six starter cultures were prepared using 250 mL shake flasks each containing sterile 50±1 mL of Soytone LB medium supplemented with 50 μg/mL Kanamycin. The inoculated Soytone-LB+50 μg/mL Kanamycin agar plates were examined for growth of colonies and each of the six starter cultures was inoculated with a single colony. The inoculated flasks were incubated at a setting of 37° C. and 120 RPM overnight.

A one milliliter sample was removed from each starter culture flask for DNA analysis by agarose gel electrophoresis and the culture flasks were stored at 2-8° C. One flask was selected to provide an approximately 3 mL (0.5%) inoculum into each of four 2 L culture flasks (containing 600 mL soytone-LB medium supplemented with 50 μg/mL Kanamycin). The inoculated flasks were incubated at a setting of 37° C. and 120 RPM overnight.

The cultures were harvested by centrifugation at a setting of 4° C., 6000×g for approximately 15 minutes. The supernatant was decanted as waste, and a total of 16.1 grams of cell paste were collected. The cell paste was divided into four sub-batches, and purified by using Qiagen EndoFree Plasmid Giga Kit (Qiagen Catalog No. 12391). Following purification, each of the four sub-batches was stored at 2-8° C. The four sub-batches were pooled and diluted to a final concentration of 0.5±0.2 mg/mL using Endotoxin-Free 10 mM Tris-HCl, 1 mM EDTA, pH 8.0. The purified PVS-RIPO plasmid DNA was filled in 1.0±0.1 mL aliquots into 2 mL cryovials, labeled as PVS-RIPO Plasmid DNA Lot L0305007, and stored at ≤−70° C. for further manufacturing use. A testing summary for PVS-RIPO Plasmid DNA Lot L0305007 is provided in Table 6.

TABLE 6

| PVS-RIPO Plasmid DNA Lot L0305007 Testing Summary | | | |
|---|---|---|---|
| Test | Method | Specification | Results/ QC Test Number |
| Identity | | | |
| DNA Sequence | Commonwealth Biotechnologies, Inc. | 100% homologous to PVSRIPO reference sequence | 100% homologous to PVSRIPO plasmid reference (Clone #6-3) QC-018312 |
| Content | | | |
| DNA Concentration by Absorbance at 260 nm | BQC SOP 01114 | ≥0.25 mg/mL $E_{260\ nm}^{1\ mg/mL} = 20$ | 0.345 mg/mL QC-018311 |

TABLE 6-continued

PVS-RIPO Plasmid DNA Lot L0305007 Testing Summary

| Test | Method | Specification | Results/QC Test Number |
|---|---|---|---|
| Purity | | | |
| A260nm/A280nm Ratio | BQC SOP 01114 | 1.75-2.00 | 1.87 QC-018311 |
| Additional Information | | | |
| Total Size (Linearized DNA) | BQC SOP 00676, 00689, 22120 | Report Results, Expected to conform with approximate size predicted from plasmid map following unique site restriction digest with Sal I, Linear, 1 fragment, 9945 bp. | Band patterns and molecular weights are concordant with control lot (Clone #6-3) and expected patterns/weights. Calculated Sal I (linear) band size: 9945 bp QC-018314 |
| Restriction Map | BQC SOP 00676, 00689, 22120 | Report Results, Expected to conform with Mun I restriction pattern predicted by the nucleotide sequence (4 bands, 1537, 2220, 2907, and 3281 bp) | Band patterns and molecular weights are concordant with control lot (Clone #6-3) and expected patterns/weights. Calculated Mun I band sizes: 1537, 2220, 2907, 3281 bp QC-018314 | d. Fermentation and DNA Purification to Produce Purified PVSRIPO Plasmid DNA Lot L0401014

Purified PVS-RIPO plasmid DNA Lot L0305007 and a GMP DH5 alpha competent working cell bank Lot L0303011 were used for DNA transformation to produce purified PVSRIPO Plasmid DNA Lot L0401014. Competent cells (DH5α competent working cell bank Lot L0303011) were thawed, gently mixed, and transferred to chilled polypropylene micro-centrifuge tubes (on wet ice) in 100 μL aliquots.

Purified DNA Lot L0305007 was diluted 10-fold in Endotoxin Free 10 mM Tris-HCl, pH 8.0, 1 mM EDTA. One microliter of the diluted DNA was added to the micro-centrifuge tubes containing the competent cell aliquots. The contents of the micro-centrifuge tubes were gently mixed. The competent cell/purified DNA suspensions were incubated on ice for 30±1 minutes, followed by a heat-shock step for 45±2 seconds in a water bath set at 40±2° C. The competent cell/purified DNA suspensions were placed on wet ice for two minutes. Room temperature Soy-LB medium (0.9 mL) was added to each micro-centrifuge tube. The Soy-LB medium formulation is described in Table 4. The suspensions were shaken at a speed setting of 120 RPM at 37±1° C. for 61 minutes, and spread, in 100 μL, 200 μL, and 400 μL aliquots, onto selective agar plates (Soy-LB Agar plates) prepared with 50 μg/mL kanamycin. The selective agar medium is described in Table 5. The plates were incubated for 20 hours 58 minutes at 37±1° C. and examined the next day for growth of colonies.

Twelve (12) starter cultures were prepared using 50 mL Soy-LB medium containing 50 μg/mL kanamycin in 250 mL baffled flasks. Each of the 12 starter cultures was inoculated with a fresh single colony from a selective agar plate. The 12 starter cultures were grown 22 hours to an optical density at an absorbance of 600 nm (OD600) greater than or equal to 1. Incubation was conducted in a shaker/incubator at 37±1° C. set at a speed of 120 RPM. On the next day, each of the 12 starter cultures was analyzed by restriction digestion using Mun I and the bands were found to be within 10% of the predicted sizes (test report QC-020628). One of the starter cultures was used to provide a 3 mL (0.5%) inoculum into each of four 2 liter shake flasks that contained 600 mL Soy-LB medium enriched with 50 μg/mL kanamycin. The inoculated 2 liter shake flasks were grown in a shaker/incubator for 18.5 hours. Incubation was performed at 37±1° C. set at a speed of 120 RPM. The cultures were tested by restriction digestion and were found to be concordant to controls and expected patterns. The cultures were harvested by centrifugation at 4° C. and 6,000×g for 15 minutes. The cells were collected, divided into four sub-batches, and purified by using Qiagen EndoFree Plasmid Giga Kit (Qiagen Catalog No. 12391). Each of the four sub-batches was tested by restriction digestion and found to be concordant to controls and expected patterns. The four sub-batches were pooled and diluted to a final concentration of 0.3±0.2 mg/mL using Endotoxin-Free 10 mM Tris-HCl, 1 mM EDTA, pH 8.0. The purified PVSRIPO Plasmid DNA was filled in 1.0±0.1 mL aliquots into 2 mL cryovials, labeled as PVSRIPO Plasmid DNA Lot L0401014, and stored at ≤−70° C. for further manufacturing use.

The tests, methods, specifications, and results conducted to qualify PVSRIPO Plasmid DNA Lot L0401014 are shown in the Certificate of Analysis (FIG. 12).

Production of PVSRIPO Initial Virus Seed Lot L0402026 (P0)

The manufacturing process to produce the PVSRIPO initial virus seed Lot L0402026 (P0), performed in the BDP Virus Production Facility, is summarized in FIG. 13 and described below.

a. Description and Testing of the Host Cell System

The Vero MCB Lot 2003-0049 was generated using Vero cells (World Health Organization [WHO] Seed, 134th Passage, October 1987). The Vero cells were harvested by trypsinization. Following centrifugation, the Vero cells were resuspended in a cryoprotectant solution of 90% fetal bovine serum (FBS) and 10% dimethyl sulfoxide (DMSO) at a concentration of approximately 1×10^7 cells/mL. A summary of the release tests, methods, specifications and results for the Vero MCB Lot 2003-0049 is included in the Certificate of Analysis shown in FIG. 14.

The Vero WCB Lot 217002-2 was produced by expansion of the Vero MCB Lot 2003-0049. One vial of the Vero MCB Lot 2003-0049 was used to initiate a Vero WCB. After four passages in Dulbecco's Modified Eagle's Medium (DMEM), High Glucose w/L-Glutamine, with Hepes containing FBS, the WCB was vialed at volume of 1 mL/vial and a concentration of 4.7×106 cells/mL. The vials labeled as Vero Master WCB Lot 217002-2 were placed into vapor phase liquid nitrogen. A summary of the release tests, methods, specifications and results for the Vero WCB Lot 217002-2 is included in FIG. 15. One of the release tests was a tumorigenicity test performed on Vero Working Cell Bank Lot 217002-2 using cells that had been passaged four times. The test results demonstrated that the Vero WCB was non-tumorigenic under these conditions. The Vero WCB, Lot 217002-2 was used throughout the PVSRIPO virus production. The starting passage from the WCB was passage 142.

b. In Vitro Transcription (L0402001) to Synthesize PVS-RIPO RNA

The PVS-RIPO plasmid DNA Lot L0401014 was used to produce PVS-RIPO RNA Lot L0402001 by in vitro transcription. Forty (40) μg of PVS-RIPO plasmid DNA lot L0401014 was linearized by Sal I digestion. The linearized DNA was extracted with phenol and chloroform, and an ethanol precipitation was performed at ≤−70° C. overnight. The DNA was resuspended in 40 μL of DNase/RNase free distilled water. A sample of the plasmid DNA before digestion/purification and after digestion/purification was analyzed by agarose gel electrophoresis to confirm the product size and recovery.

Twenty (20) μg of the linearized DNA was used as the template to synthesize the PVSRIPO RNA in two identical reactions. Each reaction was performed using 10 μg of linearized DNA. To set up the reactions, 10 μg of linearized plasmid DNA was added to the in-vitro transcription reaction mix (RiboMAX Large Scale RNA Production System, Promega, catalog number P1300) to a final volume of 100 μL. The transcription reactions were incubated at 37±1° C. for 2.5-3 hours. When the reactions were complete, the reaction tubes were placed at ≤−70° C. for storage.

To check the product size and estimate the yields of RNA from the reactions, the reaction mixtures were diluted 1 to 10 or 1 to 20 using DNase/RNase free distilled water and RNA sample buffer. The diluted reaction mixtures were then loaded onto a RNA denaturing agarose gel [Reliant Gels, 1.25% SeaKem Gold in 1×MOPS Buffer, Lonza (formerly known as Cambrex) catalog number 54948 along with the RNA ladder standard (RNA Ladder 0.24-9.5 kb, Invitrogen, catalog number 15620-016). The RNA in vitro transcription products observed on the agarose gel were found to have the expected size. The estimated concentration of RNA in the reaction mixture was 6.6 mg/mL.

c. Electroporation to Produce PVSRIPO Initial Virus Seed (Lot L0402026)

Vero cells from a qualified working cell bank (WCB) Lot 217002-2 were used in the electroporation step. The Vero WCB was established at the BDP and is described herein. Two vials of Vero cell WCB Lot L217002-2 were expanded in Dulbecco's Modified Eagle's Medium with L-Glutamine, without Phenol Red (DMEM) enriched with 10% fetal bovine serum and incubated at a setting of 37° C. and 5% $CO_2$ for three passages. The Vero cells were trypsinized by adding Trypsin-EDTA (0.05% Trypsin, 0.53 mM EDTA) and incubating at a setting of 37° C. and 5% $CO_2$ for 4-6 minutes. The trypsinized cells were collected and centrifuged at approximately 4° C. and 1000 RPM for 10 minutes. The collected cells were suspended in 100±2 mL PBS (without calcium and magnesium). A sample of the cell suspension was used to determine the cell count. The remaining cells were collected by centrifugation at a setting of 1000 RPM and 4° C. for 10 minutes. The clarified PBS was removed and the cell pellet resuspended in fresh PBS to a final calculated cell density of $1.25 \times 10^7$ cells/mL.

Approximately 55 μg of PVS-RIPO RNA (in vitro transcription lot L0402001) and 9±0.2 mL of the expanded Vero cells were combined and transferred into cuvettes in 0.8±0.01 mL aliquots. The contents of the cuvettes were subjected to two electrical shocks at 0.5 kilovolts (kv) and 0.25 microFarads (μF) using a Bio-Rad Gene Pulser II electroporation unit. After incubation at room temperature for 15 to 20 minutes, the cuvette contents were then transferred to T75 flasks with DMEM/F12 media (Invitrogen, catalog number 21041-025). The T75 flasks were incubated at a setting of 33° C. and 5% $CO_2$. The same process was repeated to generate a total of twenty T75 flasks of Vero cells transfected with PVS-RIPO RNA. Two additional control flasks contained only the post-electroporation Vero cells and the Vero cells not subjected to electroporation. The contents of the flasks were monitored for cytopathic effects (CPE) during the incubation period. Complete CPE was observed on the third day of incubation in all flasks containing Vero cells transfected with PVS-RIPO RNA.

Working in a Biological Safety Cabinet, the contents of the flasks were harvested and then clarified by centrifugation to yield the Initial Virus Seed Lot L0402026 (P0). After centrifugation at a setting of 2500 RPM for 32 minutes, the supernatants that contained the PVS-RIPO virus were collected. The supernatants were then pooled and transferred into six 125 mL Polyethylene Terephthalate Glycol (PETG) bottles in 60 mL aliquots, and to four 2 mL cryovials in 1 mL aliquots. Samples were submitted to Process Analytics (also known as Biopharmaceutical Quality Control) for in-process testing. The six bottles were labeled as PVS-RIPO Post-Electroporation Seed Lot L0402026, and transferred to ≤−70° C. storage.

Production and Testing of PVSRIPO Master Virus Seed Lot L0403006 (P1)

Figure 16:
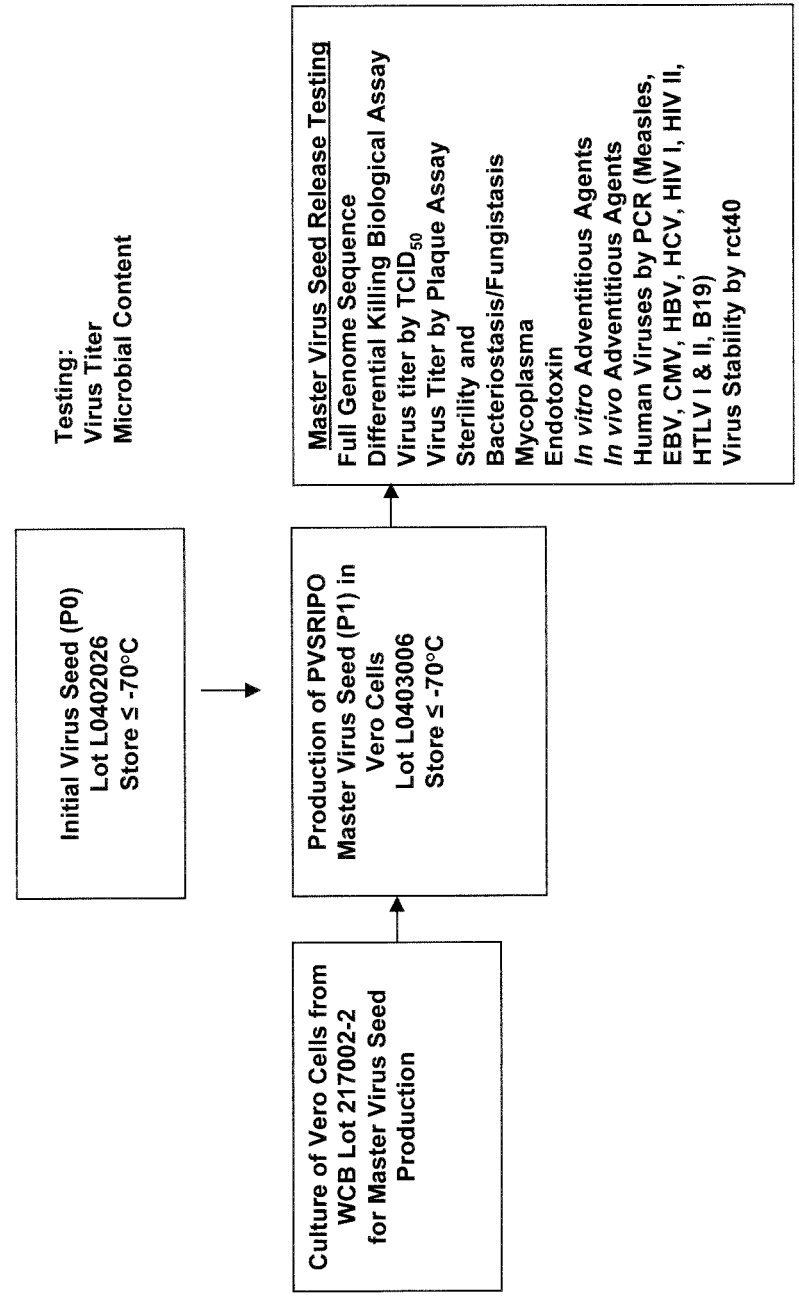
FIG. 16 is a virus Manufacturing Process Flowchart for PVSRIPO Master Virus Seed Lot L0403006 (P1).
Figure 18A:
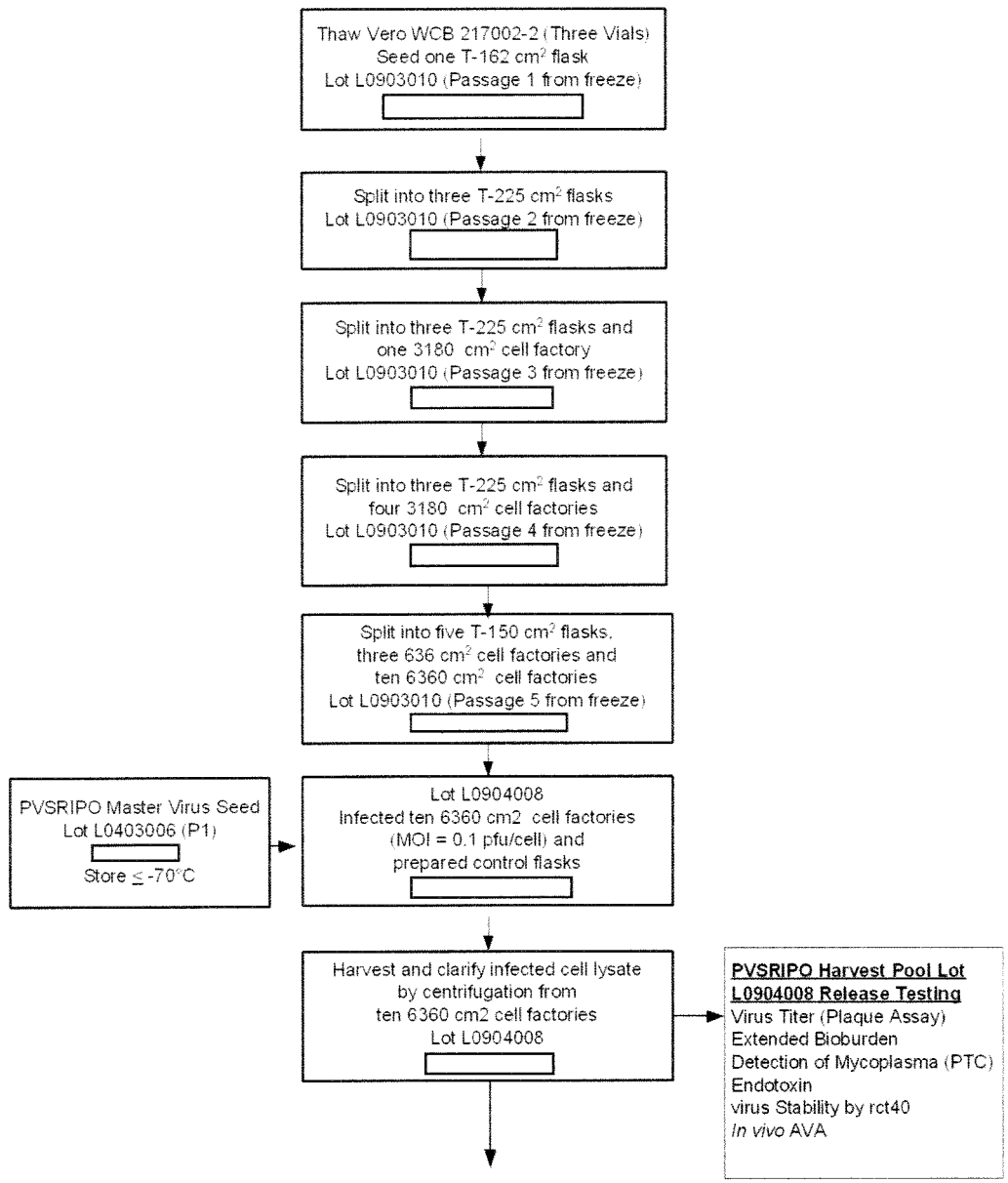
FIGS. 18A-18B is a process flowchart for Cell Expansion Lot L0903010, Infected Cell Lysate Lot L0904008, and Purification of PVSRIPO Purified Sterile Bulk Lot L0904009 (P2).
Figure 18B:
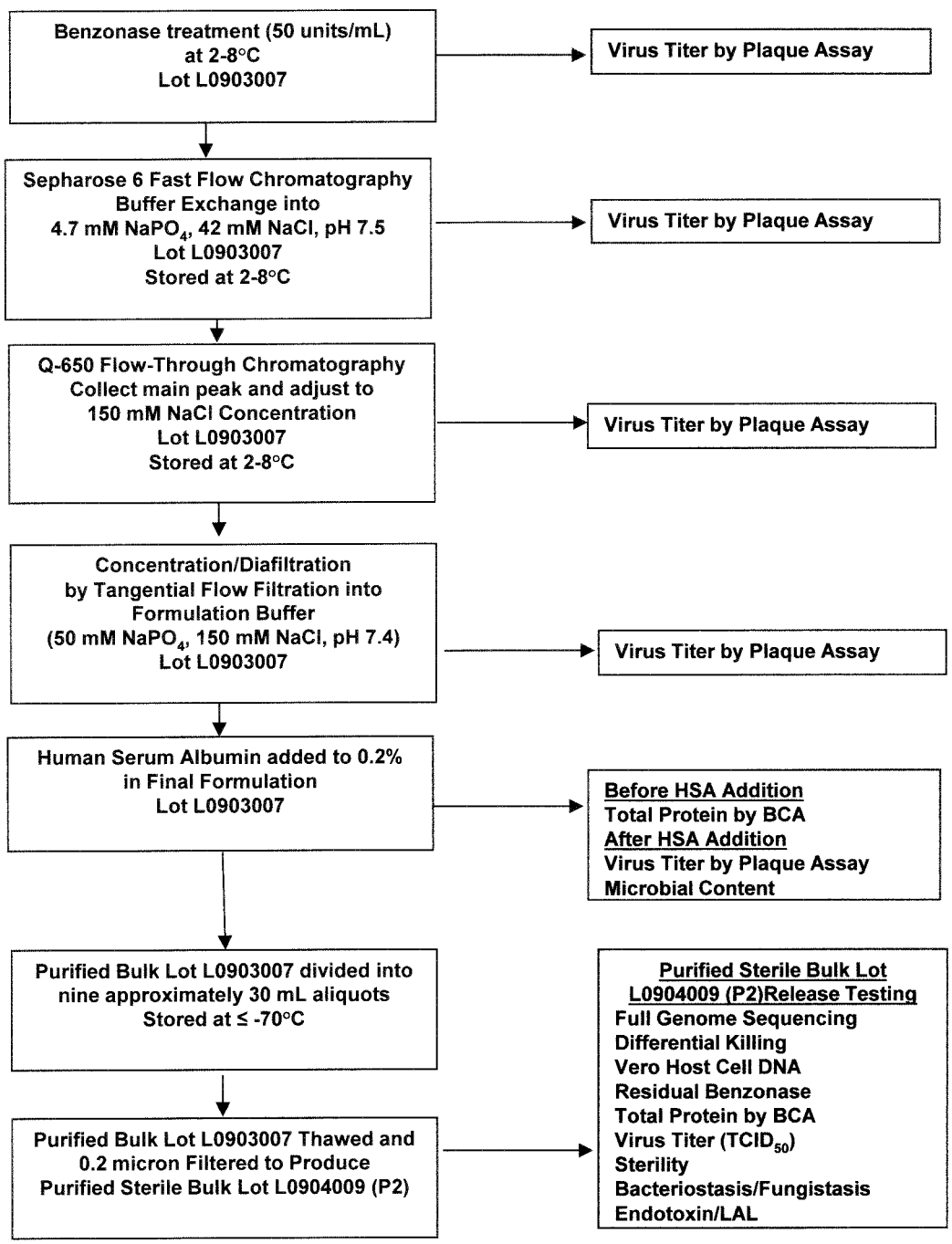

The PVSRIPO Master Virus Seed Lot L0403006 (P1) manufacturing process is summarized in FIG. 16.

a. Expansion of Vero Cells

Two vials of Vero cells (WCB Lot 217002-2) were seeded into two 25 cm² (T25) flasks containing DMEM with L-Glutamine, without phenol red (DMEM, Invitrogen Catalog Number 21063) with 10% FBS (Hyclone Catalog Number SH30070.03IR) and incubated in a $CO_2$ incubator set at 37° C. and 5% $CO_2$. The Vero cells were further expanded to fifty 162 cm² (T162) flasks after passaging the cells three times. On day three of incubation of the third passage, the contents of the fifty T162 flasks were examined under a microscope to determine the condition of the cells. Forty-three (43) flasks were selected that were pure cultures and at least 95% confluent. The cells in one of the selected T162 flasks were examined to determine the cell number and viability, and another one of the selected flasks was incubated as the "Cell quality control" flask. Of the remaining 41 of the selected T162 flasks, one flask was maintained as a negative control after inoculation with DMEM: Nutrient Mixture F12, 1:1 Mixture without phenol red (DMEM/F12, Invitrogen Catalog Number 21041).

b. Infection and Harvest of PVS-RIPO Master Virus Seed (L0403006)

The PVS-RIPO Post-Electroporation Seed Lot L0402026 was removed from storage at ≤−70° C. and thawed at room temperature. The PVS-RIPO Post-Electroporation Seed Lot L0402026 was diluted using DMEM/F12 medium and the forty T162 flasks (containing the expanded Vero cells) were infected with PVS-RIPO post-electroporation seed Lot L0402026 at a multiplicity of infection (MOI) of 0.5. The inoculated flasks were incubated at 33° C. and 5% CO2 after the addition of fresh DMEM/F12 cell culture medium.

Virus infected flasks and control flasks were monitored during incubation for attributes such as visible contamination, the condition of the cells, and percent confluency. At 70 hours post infection, incubation was terminated and the flasks were examined for attributes such as visible contamination, cell condition, and percent confluency, and then transferred into a Biological Safety Cabinet (BSC) for harvesting. The contents of the flasks were transferred into centrifuge bottles and centrifuged at settings of 4° C. and 2500 RPM for 33 minutes to clear cell debris. Supernatants containing the PVS-RIPO virus were pooled into an 850-cm2 roller bottle. The pooled supernatants were transferred into two 30 mL and twenty-four 125 mL PETG bottles in 20±1 mL and 80±5 mL aliquots, respectively. Additionally, twelve 2 mL cryovials were filled with 1±0.2 mL aliquots. The remaining supernatant (3.8 mL total) was transferred into three 2 mL cryovials for a total of fifteen 2 mL cryovials. The PETG bottles and vials were each labeled as PVSRIPO Master Virus Seed Lot L0403006. Eleven 2 mL cryovials, twenty-three 125 mL PETG bottles, and two 30 mL PETG bottles were frozen at ≤−70° C. and subsequently transferred to ≤−70° C. controlled storage. Four of the 2 mL cryovials were submitted to Process Analytics (PA)/Biopharmaceutical Quality Control (BQC) for titer (by pfu and TCID50), virus particle, and DNA sequence release testing. The remainder of the release testing was performed as appropriate assays and PVSRIPO material handling procedures were developed. The remaining 125 mL PETG bottle (20±1 mL fill) was frozen at ≤−70° C.

Supernatants in the mock infection flask (negative control) were also collected and vialed. Two 30 mL PETG bottles each with 20±1 mL of the process control material and four 2 mL cryovials each with 1±0.2 mL of the process control material were made and labeled as "PVSRIPO Process Control". The two 30 mL PETG bottles were transferred to PA/BQC for testing. The four 2 mL cryovials were frozen to ≤−70° C. and placed in controlled storage at ≤−70° C.

Release testing of the PVSRIPO Master Virus Seed Lot L0403006 is summarized in the Certificate of Analysis included in FIG. 17.

c. In Vitro Adventitious Virus Assay

In vitro adventitious virus testing was performed on the PVS-RIPO Master Virus Seed Lot L0403006. The assay was performed to evaluate the test article for the presence of adventitious viral contaminants through the observation of three types of indicator cell lines for cytopathic effects (CPE), hemadsorption (HAD), and hemagglutination (HA). Cells utilized for the detection of adventitious agents are Vero, MRC-5 and A549. All are susceptible to infection by PVS-RIPO with resultant CPE. PVS-RIPO in the test sample must therefore be neutralized in order to perform the test. We included interference controls in the assay and utilized Adenovirus 5, Parainfluenza 3 and Herpesvirus. The viruses were diluted to 10 pfu and 100 pfu and subjected to the same neutralization procedure as the PVS-RIPO. Mock neutralized controls were included. All viruses were detected in the same time period and at the same concentrations as in the mock neutralized controls. There appeared to be no effect detectable by the antibody or the neutralization procedure itself on the detection of these other model viruses.

To perform the test, the three indicator cell cultures used were: MRC-5, a normal male human embryonic cell culture; Vero, an African green monkey (Cercopithecus aethiops) kidney line; and A549, an adult male human lung carcinoma. These indicator cell cultures were inoculated with the test sample that had been neutralized with Poliovirus Type I antiserum and examined at least three times per week for at least 28 days. [The neutralization procedure was performed prior to inoculation using the following procedure: the test article was centrifuged at 1400 rpm for 10 minutes at 2-8° C. and was then mixed with an equal volume (3.0 mL) of a 1:2.5 dilution of Poliovirus Type I antiserum obtained from the FDA (Evgenia Dragunsky/CBER) and incubated at 36±2° C. for one hour. Each cell line was then dosed with 0.2 mL/well of this solution and incubated for one hour at 36±2° C., after which the inoculum was removed and the cells were washed with 2.0 mL of the appropriate medium. This wash solution was then removed and replaced with 2.0 mL of fresh medium and the cells returned to the 36±2° C. incubator.]

The cultures were examined for the development of any changes in morphology attributable to the presence of viral agents. At the end of the incubation period, the cultures were tested for hemagglutination and hemadsorption using chicken, guinea pig and human erythrocytes.

Parainfluenza 3 was used as a positive control in the assay. Viruses utilized for interference controls were Adenovirus 5, Herpesvirus, and Parainfluenza 3 neutralized with Poliovirus Type I antiserum obtained from the FDA. DMEM with 10% FBS was used as the negative control for Vero and MRC-5 cells, and F-12K with 10% FBS was used as the negative control for A549 cells.

d. In Vivo Adventitious Virus Assay (AVA) The PVS-RIPO Master Virus Seed Lot L0403006 was evaluated for adventitious viruses in vivo in guinea pigs (modified European version), adult mice, suckling mice, and embryonated hen eggs following an approved procedure. The purpose of this assay was to evaluate the test sample for the presence of virus which might have been present in the cell line but did not cause any discernable effects in the cell culture system. To complete the in vivo AVA test on the MVS Lot L0403006 the test sample was neutralized to avoid potential non-specific toxicity in test animals due to the high concentration of PVS-RIPO test samples used in the assay. Non-specific toxicity due to the PVS-RIPO viral load could interfere with the detection of other adventitious agents that might be present in the sample. To determine whether the antibody might have an effect on the detection of other adventitious agents, interference controls were set up with the antibody in an in vitro assay, as described above.

Guinea pigs are susceptible to a number of viral agents, including paramyxoviruses (Sendai) and reoviruses. Guinea pigs are inoculated with the test article using both the intramuscular and intraperitoneal routes and kept on test for a minimum of 28 days. The test sample was thawed in a waterbath set at 37° C. and then mixed in equal parts with the neutralizing antibody. The test article/neutralizing antibody mixture was maintained in a waterbath set at 37° C. for an hour with gentle mixing every twenty minutes. Five adult guinea pigs were inoculated with a 0.2 mL intramuscular injection and a 5.0 mL intraperitoneal injection of the prepared test article. Five other adult guinea pigs were inoculated with a 0.2 mL intramuscular injection and 5.0 intraperitoneal injection of Eagles Minimal Essential Medium as a negative control. Each animal was observed daily for 28 days for morbidity or mortality.

Adult mice are susceptible to a number of viral agents, including coxsackie viruses and members of the flavivirus group (St. Louis encephalitis virus and Japanese encephalitis virus). Newborn suckling mice are susceptible to a wide range of viruses including togaviruses, bunyaviruses, flaviviruses, picornaviruses (poliovirus, coxsackie virus groups A and B, echovirus), and herpes viruses. Embryonated hen eggs are inoculated through both the allantois and the yolk sac. Inoculation via the allantoic route favors replication of orthomyxoviruses (influenza virus) and paramyxoviruses (parainfluenza, mumps, and measles) in the entodermal cells of the allantois. Inoculation via the yolk sac favors propagation of herpes viruses, rickettsiae, *mycoplasma*, and bacteria. Subpassage of materials from inoculated suckling mice and inoculated embryonated eggs into new test systems serves to increase the sensitivity of this assay since any viral agents present in the original inoculum would be amplified in the new test systems.

Embryonated Eggs

The test article and neutralizing antibody were thawed using a 37±2° C. water bath. The test article and neutralizing antibody were mixed at a 1:1 ratio and incubated for 60 minutes. Prior to inoculation, both the Eagle's Minimum Essential Medium (EMEM) used for the negative control and the test-article-antibody dilution were filtered through 0.45-micron cellulose acetate low protein-binding filters.

Six (6) eggs/route of inoculation served as delivery controls. These were candled each working day for viability and chilled at the end of the incubation period. These eggs were not harvested or examined after being chilled.

Allantoic Test: The allantoic cavity of twelve eggs (10 days old) was inoculated with 0.5 mL of the prepared test article. The eggs were incubated at 37-38° C. for 3 days. The embryos were candled each working day for viability. Embryos that died prior to the end of the incubation period were chilled and all embryos were examined at the end of the incubation period. The passage 1 (P1) allantoic fluids were harvested, pooled and stored at or below −60° C. until assayed for hemagglutination activity (HA) or until subpassaged into a second set of ten eggs (11 days old). Prior to inoculation into the second set of eggs, the subpassaged material was clarified by low speed centrifugation and filtered through a 0.45 micron cellulose acetate low protein-binding filter. The second set of eggs was incubated under the same conditions as the first set. The passage 2 (P2) allantoic fluids were then harvested, pooled, and stored at or below −60° C. until assayed for HA, after which time the embryos were examined. To establish negative controls, this procedure was run in parallel for two additional sets of embryonated eggs using 0.45-micron filtered EMEM as the initial inoculum.

Yolk Sac Test: The yolk sac of twelve embryonated eggs (6 days old) was inoculated with 0.5 mL of the prepared test article. The eggs were incubated at 37-38° C. for 9 days. The embryos were candled each working day for viability. Embryos that died prior to the end of the incubation period were chilled and all embryos were examined at the end of the incubation period. The P1 yolk sacs were harvested, washed, and pooled. A 10% yolk sac suspension was prepared and stored at or below −60° C. until subpassaged into a second set of twelve (12) eggs (6 days old). Prior to inoculation into the second set of eggs, the subpassaged material was clarified by low-speed centrifugation and filtered through a 0.45-micron cellulose acetate low protein-binding filter. The second set of eggs was incubated under the same conditions as the first set, after which time the embryos were examined. To establish negative controls, this procedure was run in parallel for two additional sets of embryonated eggs using 0.45-micron filtered EMEM as the initial inoculum.

The hemagglutination assay was performed in microtiter plates by making serial two-fold dilutions of both the P1 and P2 pooled allantoic fluids, the corresponding P1 and P2 negative controls, the stock influenza type A virus, which served as the positive control. EMEM served as the assay negative control. Washed chicken, guinea pig, and human type 0 erythrocytes were added separately as 0.5% suspensions. Replicate plates were observed for HA activity after incubation at both 2-8° C. and 37±2° C. for 1-2 hours.

The test article was considered negative for the presence of detectable adventitious viral contaminants if at least 80% of the inoculated embryos survived the test period (excluding those that die due to trauma or bacterial contamination), were normal in appearance; and the allantoic fluids collected from the inoculated embryos did not produce hemagglutination.

Adult and Suckling Mice

The frozen test article was thawed in a waterbath set at 37° C. and then mixed in equal parts with the neutralizing antibody. The test article/neutralizing antibody mixture was maintained in a waterbath set at 37° C. for an hour with gentle mixing every fifteen minutes. Twenty (20) adult mice were inoculated with the prepared test article and five (5) adult mice were inoculated with the control article (EMEM). Each test or control mouse was injected with a 0.03 mL intracerebral injection and a 0.5 mL intraperitoneal injection of the appropriate material. The animals were observed daily for clinical signs suggestive of infection. On day 21 after inoculation, the mice were sacrificed.

Twenty (20) newborn suckling mice were inoculated with the prepared test article and 20 newborn suckling mice were inoculated with the control article. Each mouse was given a 0.01 mL intracerebral and a 0.1 mL intraperitoneal injection of the appropriate material. The animals were observed daily for abnormal clinical signs. On day 14 after inoculation, the mice were sacrificed and tissues were harvested, homogenized and pooled within the test group or the control group. The tissues were homogenized with EMEM and centrifuged at low speed. The tissue homogenates were filtered through a low-protein-binding 0.45-micron cellulose acetate filter loaded into appropriate size syringes for injection. Twenty (20) newborn suckling mice were inoculated with the test mice tissue supernatant and 20 mice were injected with the control mice tissue supernatant (0.01 mL intracerebral and 0.1 mL intraperitoneal injections). On day 14 after the injections of the tissue homogenates, the mice were sacrificed.

The test article was considered negative for the presence of detectable adventitious viral contaminants if at least 80% of the suckling mice and at least 80% of the adult mice survive the test period with no adverse clinical observations consistent with a contaminant adventitious transmissible agent.

Production of PVSRIPO Purified Sterile Bulk Lot L0904009 (P2) The manufacturing process to produce PVS-RIPO Purified Sterile Bulk Lot L0904009 (P2) is illustrated in FIGS. 18A-18B. PVS-RIPO Purified Sterile Bulk Lot L0904009 was manufactured using the Vero Working Cell Bank (WCB) Lot 217002-2 and the MVS Lot L0403006 as the starting materials. Three vials of the Vero WCB Lot 217002-2 were expanded to produce cell expansion Lot L0903010 in ten 6360 cm2 cell factories. The cell expansion Lot L0903010 was infected with the PVSRIPO MVS Lot L0403006 and the harvested material (Harvest Pool Lot L0904008) was used for the production of PVSRIPO Purified Bulk Lot L0903007 and subsequently the PVSRIPO Purified Sterile Bulk Lot L0904009.

a. Initiation and Expansion of Vero Cells Vero cells from cell expansion Lot L0903010 were used for the production of cell harvest Lot L0904008. Throughout the expansion the Vero cells were grown in DMEM supplemented with L-glutamine and 10% irradiated fetal bovine serum (FBS) and incubated at a setting of 37° C. and 5% CO2. Three vials of the Vero Working Cell Bank (WCB) Lot 217002-2, were thawed in a 37±2° C. water bath and used to seed one T-162 cm2 flask at a density of approximately 50,864 cells/cm2 (passage 1 out of freeze). The cells were expanded from T-162 cm2 flasks to 6360 cm2 cell factories, 636 cm2 cell factories and T-150 cm2 flasks using the growth medium and conditions described above for a total of five passages from freeze (refer to FIGS. 18A-18B).

b. Infection of Vero Cells

To produce the infected cell lysate Lot L0904008, Vero Cell Lot L0903010 (ten 6360 cm2 cell factories, three 636 cm2 cell factories, and five T-150 cm2 flasks) containing healthy cells at 95-100% confluence and no visible signs of contamination were used. Four PVS-RIPO Master Virus Seed (MVS) Lot L0403006 bottles (125 mL PETG bottles with 80 mL MVS aliquots) were withdrawn from ≤−70° C. controlled storage, thawed in a 33-38° C. water bath, and used in the infection process at a multiplicity of infection (MOI) of 0.1 pfu/cell. Formulated infection medium was prepared by adding 265 mL of the thawed MVS Lot L0403006 to prepared Infection Medium (DMEM/F12 with L-glutamine without Hepes and Phenol Red) for a total volume of approximately 8 liters.

The ten 6360 cm2 cell factories were prepared for infection by washing with approximately 750 mL of wash medium (DMEM/F12 with L-glutamine without Hepes and Phenol Red) and then filling with approximately 750 mL of the prepared formulated infection medium. Positive and negative controls were also prepared. Infected cell factories and controls were incubated at settings of 33° C., 5% CO2 concentration and 80% humidity. At 70 hours post infection, 100% cytopathic effects (CPE) were noted in nine cell factories and 80% CPE in one cell factory, and the expected results were noted in each of the control flasks.

c. Harvest and Clarification of Infected Cell Lysate

The PVS-RIPO virus-infected cell suspension Lot L0904008 was harvested from each cell factory and pooled into a sterile media bag. The infected cell suspension was sampled for release testing of the PVSRIPO Harvest Pool Lot L0904008. The Certificate of Analysis summarizing the tests, specifications, methods, and results of the PVSRIPO Harvest Pool Lot L0904008 release testing is included in FIG. 19.

The infected cell suspension was transferred into 1 L polycarbonate centrifuge bottles in approximately 750 mL aliquots. The infected cell suspension was centrifuged at a setting of 4° C. and 3800×g for approximately 20 minutes. The clarified supernatant from each of the centrifuge bottles was pooled into a sterile 10 liter media bag and transferred to the Purification Group at room temperature.

d. Benzonase Treatment of Final Harvest

To reduce the level of host genomic DNA during the production of PVS-RIPO Purified Bulk Lot L0903007, the clarified PVSRIPO Lot L0904008 harvest was incubated with Benzonase® enzyme. Prior to the addition of Benzonase® enzyme, magnesium chloride was added, with mixing, to the clarified PVSRIPO Lot L0904008 harvest to a 1 mM final concentration. Benzonase® enzyme was added, with mixing, to a final concentration of 50 units/mL. The bag was incubated at 2-8° C. for 16 hours. The Benzonase® enzyme treated lysate was removed from 2-8° C. and sampled. The sample analyzed using a plaque assay to determine the virus titer.

e. Sepharose 6 Fast-Flow Chromatography

The Sepharose 6 FF Chromatography step provides buffer exchange and partial purification of the virus pool from low molecular weight host cell contaminants during the production of PVS-RIPO Purified Bulk Lot L0903007. A chromatography column packed with Sepharose 6 Fast Flow (FF) resin (GE Healthcare-Biosciences, Piscataway, N.J.) was used to buffer exchange the virus into a low conductivity phosphate buffer in preparation for further purification. Prior to loading the Benzonase® enzyme treated lysate the Sepharose 6FF column was flushed with 5M NaCl, charged with 4.7 mM NaPO4, 1 M NaCl, pH 7.5 and equilibrated with 4.7 mM NaPO4, 42 mM NaCl, pH 7.5 The Benzonase treated lysate was loaded onto the Sepharose 6FF column in two equal injections on May 19, 2009. The product was eluted with 4.7 mM NaPO4, 42 mM NaCl, pH 7.5 and the PVS-RIPO main peak fraction from both injections was collected into the same receiving bag. A sample of the collected eluate was analyzed using a plaque assay to determine the virus titer. The PVS-RIPO Main Peak was stored at 2-8° C.

f. Q650M Flow-Through Chromatography

After the Sepharose 6 FF step, the Lot L0903007 eluate was applied to a Q650M Flow Through chromatography column to remove the remaining host cell protein contaminants from the non-binding virus. The chromatography column was packed with Super Q 650M resin and prepared by flushing with 5M NaCl, followed by charging with 4.7 mM NaPO4, 1 M NaCl, pH 7.5 and equilibration using 4.7 mM NaPO4, 42 mM NaCl, pH 7.5. The column was loaded with the PVS-RIPO Sepharose 6FF Main Peak and the flow through containing the virus product was collected. The buffer used during elution was 4.7 mM NaPO4, 42 mM NaCl, pH 7.5. The NaCl concentration of the collected Q650M main peak was adjusted to 150 mM NaCl using 5M NaCl. The Q650M main peak material was sampled and then stored at 2-8° C. A sample was analyzed using a plaque assay to determine virus titer.

g. Concentration and Diafiltration by Tangential Flow Filtration

The Q650M main peak Lot L0903007 material was removed from 2-8° C. storage and concentrated using an ultrafiltration hollow-fiber membrane (GE Healthcare UFP-50-C-4MA). The concentrated virus material was then diafiltered against the formulation buffer (50 mM NaPO4, 150 mM NaCl, pH 7.4). Samples of the diafiltered PVS-RIPO solution were analyzed by plaque assay to determine virus titer. HSA (25%) was added to the diafiltered PVS-RIPO Lot L0903007 to a final concentration of 0.2%. Samples of the formulated PVS-RIPO were analyzed by plaque assay and microbial content.

h. Bulk Aliquot, Sampling and Storage of PVS-RIPO

The formulated PVS-RIPO Purified Bulk Lot L0903007 was moved into a class 100 Biological Safety Cabinet and dispensed into nine 125 mL PETG bottles at a volume of approximately 30 mL each. The nine bottles of PVS-RIPO Purified Bulk Lot L0903007 were labeled, frozen in an ethanol/dry ice bath, and stored at ≤−70° C. for further manufacturing use. The PVS-RIPO Purified Bulk Lot L0903007 was transferred to controlled storage at ≤−70° C.

i. Purified Sterile Bulk Lot L0904009 (P2)

Nine bottles of the PVS-RIPO Purified Bulk Lot L0903007 were withdrawn from ≤−70° C. controlled storage and transferred to a ≤−70° C. freezer. The nine bottles of the PVS-RIPO Purified Bulk Lot L0903007 were thawed in a water bath at 24-31° C.; the product temperature was 11-17° C.). The total thaw time was 43 minutes. The contents of the nine containers were pooled into a 1 L PETG bottle to yield a final total volume of 271.09 mL. The pooled PVS-RIPO Purified Bulk Lot L0903007 was pumped through a 0.2 micron sterile Millipak 20 (Millipore) filter that had passed pre-use testing and had been pre-wetted with diluent (50 mM NaPO4 in 0.9% NaCl, pH 7.4+0.2% HSA). The filter was flushed using the same diluent following product filtration yielding a total amount of 283.24 mL filtered product. The filter passed post-filtration integrity testing. Samples were collected (25.5 mL) and submitted to Process Analytics/Biopharmaceutical Quality Control for Purified Sterile Bulk Lot L0904009 release testing leaving a total final volume of 257.74 mL. The Purified Sterile Bulk Lot L0904009 then proceeded to the filling step. Release testing, methods, specifications and results for the PVSRIPO Harvest Pool Lot L0904008 are provided in FIG. 19.

Test Method Descriptions for PVSRIPO Harvest Pool Lot L0904008 a. Virus Titer (TCID50 Assay)

This assay was performed to determine the PVS-RIPO virus titer in the PVS-RIPO Harvest Pool Lot L0904008, Purified Sterile Bulk Lot L0904009 and Final Vialed Product Lot L0904010 by TCID50 on Hep-2C indicator cells. One hundred microliters (100 µL) of dilution medium (RPMI-1640 with 4 mM L-Glutamine and 1% FBS) were added to each well of separate 96-well plates (providing separate plates for each reference standard, positive control and test samples). Initial dilutions of the FDA Poliovirus Type 1 Reference Standard (1:10000), Sabin Original Type 1 Positive Control Poliovirus (1:1000000) and Test Samples (1:1000000) were prepared with the dilution medium (RPMI-1640 with 4 mM L-Glutamine and 1% FBS). A 100 µL aliquot of each final dilution was added to each of the eight wells in the first column of the respective 96-well plate. Using a calibrated multichannel pipettor, serial 1:2 dilutions were made on each 96-well plate by removing 100 µL from each well in column 1, transferring to the adjacent wells in column 2, mixing thoroughly and repeating the process for the next column in the series. For the FDA Reference Standard the dilution terminated at column 11 with column 12 used as Negative Control wells (containing dilution medium only). The excess 100 µL from the column 11 were discarded. For the Positive Control and Test Articles, the dilution scheme continued onto a second 96-well plate, terminating at column 23 with column 24 used as Negative Control wells. Ten thousand Hep-2C cells in growth medium (RPMI-1640 with 4 mM L-Glutamine and 10% FBS) (0.1 mL at $1\times10^5$ cells/mL) were then added to each well of each 96-well plate and incubated at 36±1° C. in a humidified, 5% $CO_2$ incubator for 10 days. The plates were examined for Cytopathic Effects (CPE) on Days 1, 3, 7 and 10. Upon completion of the assay, the number of wells exhibiting CPE for each sample was entered into the appropriate fields of the calculation program template provided by the FDA. The program calculates the $TCID_{50}$/mL for each sample, based on the response of the FDA Poliovirus Type 1 Reference Standard.

b. Extended Bioburden

Bioburden is an estimation of the number of viable aerobic microorganisms present in an aqueous sample. Bioburden testing of the PVS-RIPO Harvest Pool Lot L0904008 was performed using a Milliflex-Sensor II system, a fast and high throughput filtration device for detection and enumeration of microorganisms.

Duplicate test samples (2.5 mL) were diluted to 50 mL with sterile phosphate buffered saline (PBS) and added directly into the top of separate Milliflex filtration funnels. A negative control was prepared by filtering 100 mL of PBS. A vacuum was applied to each filtration device to absorb the test sample or control into the filter membrane. The funnel was removed and the filter membrane was applied to the appropriate type of agar to promote growth of any microorganisms present. One of the filter membranes from the duplicate test samples was applied to Tryptic Soy Agar (TSA) (used to aid in the growth of bacteria) and the other filter membrane was applied to Sabouraud Dextrose Agar (SDA) (used to aid in the growth of yeast and mold). Both the TSA and SDA media were tested for growth promotion as part of the raw material release testing. The TSA sample was incubated at 30-35° C. for 120 hours and the SDA sample was incubated at 20-25° C. for 120 hours in the inverted position. After the incubation period, the agar plates were examined for growth and the number of colonies (if observed) were enumerated and reported as colony forming units/mL.

c. Detection of *Mycoplasma* (PTC) Using NIH/3T3 Cells

Detection of *mycoplasma* was performed on Harvest Pool Lot L0904008 using both an indirect and direct procedure.

The indirect method of detection allows visualization of *mycoplasma*, particularly non-cultivable *mycoplasma*, by growing the *mycoplasma* on NIH/3T3 cells (Swiss mouse embryo cell line) and then staining using a DNA-binding fluorochrome stain. Both negative and positive controls were used in the assay. Positive controls included both a strong cyto-adsorbing (*M. hyorhinis*) and a poor cyto-adsorbing (*M. orale*) *mycoplasma* species. Staining the cultures with DNA-binding fluorochrome allows for the detection of *mycoplasma* based on the staining pattern observed. In the negative cultures only the cell nuclei fluorescence is observed, while nuclear and extra-nuclear fluorescence are observed in positive cultures.

Direct cultivation is a sensitive and specific method for the detection of *mycoplasma*. The agar and broth media used supply nutrients along with carbon and energy needed for the growth of cultivatable mycoplasmas. Both positive and negative controls were used in the direct assay. Positive controls included a fermentative *mycoplasma* (*M. pneumoniae*) and a non-fermentative *mycoplasma* (*M. orale*). This procedure is based on the protocol described in the 1993 "Points to Consider in the Characterization of Cell Lines Used to Produce Biologicals" in Attachment #2 as recommended by the FDA, Center for Biologics Evaluation and Research.

d. Endotoxin by Limulus Amoebocyte Lysate (LAL)

The endotoxin (LAL) content of the PVSRIPO Harvest Pool Lot L0904008, Purified Sterile Bulk Lot L0904009 and the PVSRIPO Final Vialed Product Lot L0904010 was determined using kinetic chromogenic testing. The test is based upon the reactivity of Limulus Amoebocyte Lysate, a derivative of Limulus polyphemus amoebocytes, to determine endotoxin in the test article. The procedure is designed to meet recommendations stated in the FDA's Guidance on Validation of the Limulus Amebocyte Lysate Test (LAL) as an End-Product Endotoxin Test for Human and Animal Parenteral Drug, Biological Products, and Medical Devices, issued December 1987.

Pyrogens are fever-producing materials that most often originate from Gram-negative bacterial cell walls. Pyrogens from bacterial cell walls are referred to as bacterial endotoxin and are readily detected by kinetic chromogenic LAL testing systems. The kinetic chromogenic LAL method provides direct quantification of the detected endotoxin level and is especially useful for detection of low levels of endotoxin. Reagents and standards are prepared in accordance with the manufacturer's instructions.

The test is performed by pipetting 25 μL of the test sample into each of the four sample reservoirs in the Endosafe-Licensed PTS Endotoxin Cartridge. The PTS draws and mixes the test sample with the LAL reagent in two channels and with the LAL reagent and Positive Product Control (PPC) in the other two channels. The sample is incubated and then combined with the Chromogenic Substrate. After mixing, the optical density of the wells is measured and analyzed against an internally-archived, batch specific standard curve. The PTS simultaneously performs testing in duplicate and averages the results in keeping with USP guidelines. The assay is valid if the coefficient of variation (CV) is <25% between the two sample replicates and the CV is <25% between the two PPC replicates. The results are valid if the PPC recovery is 50-200%. The limit of detection of this assay is 0.005 EU/mL.

e. Virus Stability by rct40

The assay was used to determine the titer of PVSRIPO in the Harvest Pool Lot L0904008, Final Vialed Product Lot L0904010 and controls at 36° C. and 40° C. by plaque formation on Vero indicator cells. The log 10 titers of the virus at 36° C. and 40° C. are compared and if the log reduction between 36° C. and 40° C. is at least five, the sample is determined to be sensitive to growth at 40° C. and is considered to have passed the test. The titer of the sample at 33° C. is also determined so that it can be compared to the previously determined titer of the sample at 33° C. The positive controls included RCT 40+ control: Poliovirus 1 Sabin Clone S33 Lot L0406008 and RCT 40-Control: Poliovirus 1 Sabin Clone S71 Lot L0406004. The negative control was DMEM containing 10% FBS.

Vero cells were plated and allowed to grow until 80 to 100 percent confluence had been attained. The growth medium was removed and the Vero cells were dosed with 0.2 mL of test or control sample. Replicate dishes were then incubated at 33° C., 36° C. and 40° C. for approximately one hour. The inoculum was removed and the cell sheet overlaid with agarose/2× Eagle's Minimum Essential Medium (EMEM). The agarose was allowed to solidify and replicate dishes were incubated at 33° C., 36° C. and 40° C. until plaques were fully formed in the positive controls (2 days). The dishes are then overlaid with agarose/2×EMEM containing neutral red in the dark and the plaques were counted when the neutral red had stained the cell sheet. The mean plaque value was determined. The titer (pfu/mL) was calculated using the formula: Mean plaque value×dilution factor/volume inoculated.

f. In Vivo Adventitious Agents

The PVS-RIPO Harvest Pool Lot L0904008 was evaluated for adventitious viruses in vivo in adult mice, suckling mice, and embryonated hen eggs. The purpose of this assay was to evaluate the test sample for the presence of virus which might have been present in the cell line but did not cause any discernable effects in the cell culture system. Prior to in vivo AVA testing of the PVS-RIPO Harvest Pool Lot L0904008, R&D studies were performed under QC-040664 to evaluate the approach used to complete this test. These R&D studies demonstrated that no adverse effects in suckling mice were observed when dosed with PVS-RIPO virus lysate preparations at a concentration of $2 \times 10^8$ pfu/mL. Therefore, the in vivo AVA test was conducted on the PVS-RIPO Harvest Pool Lot L0904008 without including a neutralizing antibody treatment. The material was tested undiluted ($2.14 \times 10^9$ $TCID_{50}$/mL) in embryonated hen eggs. The material was then diluted to $2 \times 10^8$ pfu/mL and tested in adult and suckling mice.

Adult mice are susceptible to a number of viral agents, including coxsackie viruses and members of the flavivirus group (St. Louis encephalitis virus and Japanese encephalitis virus). Suckling mice are susceptible to a wide range of viruses including togaviruses, bunyaviruses, flaviviruses, picornaviruses, (poliovirus, coxsackie virus groups A and B, echovirus), and herpes viruses. Embryonated hen eggs are inoculated through both the allantois and the yolk sac. Inoculation via the allantoic route favors replication of orthomyxoviruses (influenza virus) and paramyxoviruses (parainfluenza, mumps, and measles) in the entodermal cells of the allantois. Inoculation via the yolk sac favors propagation of herpes viruses, rickettsiae, *mycoplasma*, and bacteria. Subpassage of materials from inoculated suckling mice and inoculated embryonated eggs into new test systems serves to increase the sensitivity of this assay since any viral agents present in the original inoculum would be amplified through this serial passage.

Embryonated Eggs

Six (6) eggs/route of inoculation served as delivery controls. These were candled each working day for viability and chilled at the end of the incubation period. These eggs were not harvested or examined after being chilled.

Allantoic Test: The allantoic cavity of twelve (12) eggs (10 days old) was inoculated with 0.5 mL of test article. The eggs were incubated at 37-38° C. for 3 days. The embryos were candled each working day for viability. Embryos that died prior to the end of the incubation period were chilled and all embryos were examined at the end of the incubation period. The passage 1 (P1) allantoic fluids were harvested, pooled and stored at or below −60° C. until assayed for hemagglutination activity (HA) or until subpassaged into a second set of twelve (12) eggs (10 days old). Prior to inoculation into the second set of eggs, the subpassaged material was clarified by low speed centrifugation and filtered through a 0.45 micron cellulose acetate low protein binding filter. The second set of eggs was incubated under the same conditions as the first set. The passage 2 (P2) allantoic fluids were then harvested, pooled, and stored at or below −60° C. until assayed for HA, after which time the embryos were examined. To establish negative controls, this procedure was run in parallel for two additional sets of embryonated eggs using 0.45 micron filtered EMEM as the initial inoculum. The HA assay was performed in microtiter plates by making serial two-fold dilutions of both the P1 and P2 pooled allantoic fluids, the corresponding P1 and P2 negative controls, and stock influenza type A virus, which served as the positive control. EMEM served as the assay negative control. Washed chicken, guinea pig and human type 0 erythrocytes were added separately as 0.5% suspensions. Replicate plates were observed for HA activity after incubation at both 2-8° C. and 37±2° C. for 1-2 hours.

Yolk Sac Test: The yolk sac of twelve (12) embryonated eggs (6 days old) was inoculated with 0.5 mL of 0.45-micron filtered test article. The eggs were incubated at 37-38° C. for 9 days. The embryos were candled each working day for viability. Embryos that died prior to the end of the incubation period were chilled and all embryos were examined at the end of the incubation period. The P1 yolk sacs were harvested, washed, and pooled. A 10% yolk sac suspension was prepared and stored at or below −60° C. until subpassaged into a second set of twelve (12) eggs (6 days old). Prior to inoculation into the second set of eggs, the subpassaged material was clarified by low-speed centrifugation and filtered through a 0.45-micron cellulose acetate low protein-binding filter. The second set of eggs was incubated under the same conditions as the first set, after which time the embryos were examined. To establish negative controls, this procedure was run in parallel for two additional sets of embryonated eggs using 0.45-micron filtered EMEM as the initial inoculum.

The test article was considered negative for the presence of detectable adventitious viral contaminants if at least 80% of the inoculated embryos survived the test period (excluding those that die due to trauma or bacterial contamination), were normal in appearance; and the allantoic fluids collected from the inoculated embryos did not produce hemagglutination.

Adult and Suckling Mice

Twenty (20) adult mice were inoculated with the prepared test article and five (5) adult mice were inoculated with the control article. The animals were observed daily for clinical signs suggestive of infection. On day 21 after inoculation, the mice were sacrificed. Twenty (20) newborn suckling mice were inoculated with the prepared test article and 20 newborn suckling mice were inoculated with the control article. The animals were observed daily for abnormal clinical signs. On day 14 after inoculation, the mice were sacrificed and tissues were harvested, liquefied and pooled within the test group or the control group. The tissues were homogenized with EMEM and centrifuged at low speed. Twenty (20) newborn suckling mice were inoculated with the test mice tissue supernatant and 20 mice were injected with the control mice tissue supernatant. The tissue supernatants were first filtered through a 0.45-µm filter and loaded into appropriate sized syringes for injection. On day 14 after the injection, the mice were sacrificed. The test article was considered negative for the presence of detectable adventitious viral contaminants if at least 80% of the suckling mice and at least 80% of the adult mice survive the test period with no adverse clinical observations consistent with the presence of a transmissible agent.

Release testing, methods, specifications and results for the PVSRIPO Purified Sterile Bulk Lot L0904009 are provided in the Certificate of Analysis in FIG. 20.

Test Method Descriptions for PVSRIPO Purified Sterile Bulk Lot L0904009 a. Full Genome Sequencing

A comprehensive 4× sequence analysis of PVS-RIPO Purified Sterile Bulk Lot L0904009 and Final Vialed Product Lot L0904010 was performed according to an approved procedure. The viral RNA was isolated from the test article, and the genome was reverse transcribed and amplified in approximately 1200 bp sections. DNA sequence analysis of the amplicons was obtained using oligonucleotides. The primers were designed approximately 250 bases apart, to have approximately 50% GC content, be between 18-24 bp in length, and positioned such that both strands of amplified viral cDNA were sequenced with two reads from each strand.

Fluorescent dye-terminator DNA cycle sequencing of the test articles and the pGEM3Z control plasmid was carried out using the BigDye v1.1 Sequencing Kit. For the test samples: 2.0 µL of 5× Big Dye Sequencing Buffer was combined with 2 µL of 2 µM primer, 20 ng of purified PCR product and ddH2O to a final volume of 10 µL. For the pGEM3Z control reactions that serve as the reaction and instrument controls: 200 ng of pGEM3Z were sequenced with 20 ng (approximately 3.2 pmol) M13F-20 primer (5' GTAAAACGACGGCCAGT-3', SEQ ID NO: 4). Control reactions were performed with each sequencing set-up and analyzed on the ABI3130x1. Cycle sequencing reactions were performed using the PTC-225 Peltier thermal cycler. Before analysis, sequence reactions were purified from unincorporated dye terminators, salts, and low molecular weight compounds using Centriflex Gel Filtration Cartridges. Sequence data were gathered from the sequencing computers and the data was trimmed and aligned into a contiguous series of fragments (known as a "contig") using Sequencher software version 4.7 (GeneCodes, Ann Arbor, Mich.). The aligned DNA sequence was compared to the reference sequence and base mismatches or polymorphisms, if any, between the test sample and the reference sequences were identified.

DNA sequence analysis used a reference sequence obtained from Process Analytics/Biopharmaceutical Quality Control Test Report QC037657 (Toxicology Xenograph Study Virus Lot 022208, sample provided by Dr. M. Gromeier, Duke University, Durham, N.C.). The sequence of the PVSRIPO Purified Sterile Bulk Lot L0904009 and Final Vialed Product Lot L0904010 was found to be 100% homologous at all 7303 base positions when compared to the cloned viral plasmid sequence contained in the PVSRIPO plasmid reference sequences from QC020658 (GMP plasmid lot L0401014), and to the viral cDNA sequence from the master viral seed (MVS) sequence, lot L0403006, QC022271.

b. Host Cell DNA (Vero)

The PVSRIPO Purified Sterile Bulk Lot L0904009 was tested for Vero genomic DNA load using a TaqMan®-based quantitative polymerase chain reaction (qPCR) (Applied Biosystems Inc., Foster City, Calif.) amplicon targeting the *Cercopithecus aethiops* (Vero) specific nectin-1α gene intragene duplication, a single-copy gene (GenBank® Accession No. AF308635). The limit of detection for the assay is 1 ng Vero genomic DNA per mL. Vero cell genomic DNA (gDNA) was used as the positive control (100 ng-1 pg), a 5 ng Vero gDNA spike of the test article was used as the PCR inhibition control, the negative control result desired was no test control reaction with nuclease free water, and the extraction control was phosphate buffered saline (PBS) buffer/PBS buffer containing equivalent of 100 pg Vero gDNA per reaction.

Real-time qPCR is a sensitive quantitative amplification method that can be utilized for gene expression analysis, genotyping, pathogen detection/quantitation, mutation screening and precise DNA detection, including the quantitation of low copy residual DNA or RNA in a sample. An Applied Biosystems 7900HT 96-well instrument was used to detect the accumulation of PCR amplification product continuously during the amplification process, allowing accurate target quantitation in the exponential phase of PCR. The use of a 96-well block allows for greater reaction volumes than a 384-well block and thus increases the assay sensitivity for residual DNA and contaminant DNA studies.

TaqMan® qPCR chemistry utilizes a dual-labeled fluorogenic oligonucleotide TaqMan® probe. The TaqMan® probe used for detection of human genomic DNA is composed of an oligonucleotide end labeled with two fluorescent dyes with distinguishable emission maxima. The probe 5' terminus is labeled with a reporter dye, 6-Carboxyfluorescein (6-FAM), and the 3' probe terminus is labeled with a quenching dye, Carboxytetramethylrhodamine (TAMRA). The oligonucleotide probe is homologous to an internal target sequence within the *Cercopithecus aethiops* (Vero) nectin-1α gene PCR amplicon and is highly specific to Vero and CV-1 cells. A high rejection ratio of Vero to human gDNA is achieved by utilizing a nine base sequence duplication event unique to *C. aethiops* that is not present in human gDNA, as a portion of the probe target. While intact and in free solution, the probe quenching dye reduces the fluorochrome reporter emission via fluorescent resonant energy transfer (FRET). During the extension phase of a TaqMan® PCR reaction the probe is cleaved by the 5' nuclease activity of the Taq DNA polymerase, releasing the reporter dye from the probe and allowing an increase in reporter emission.

The ABI Prism 7900HT uses a dual-axis scanning head to distribute the excitation light from an argon-ion (488 nm) laser to all 96 wells. A Charge Coupled Device (CCD) imager measures the fluorescence spectrum and intensity from each well to generate real-time spectral data during PCR amplification. ABI Sequence Detection Software (SDS) deconvolutes the fluorescence intensity of reporter, quencher, and normalizer (ROX) dyes and calculates the increase in normalized reporter emission intensity over the course of the amplification.

Precise quantification of initial target in each PCR reaction occurs during the exponential (log 2) phase of the amplification prior to reagent exhaustion or by-product inhibition of the reaction. However due to signal to noise limits of the reaction and general background fluorescence, the most accurate data are typically generated late in log phase. Normalized reporter fluorescence is plotted versus time, represented by the PCR cycle number. Target copy numbers or mass values are generated by assigning a fluorescence threshold above background and determining the cycle point at which each sample's amplification plot reaches the threshold (defined as the threshold cycle or Ct). Threshold cycle values for each reaction are used to quantitate the amount of target initially contained within each test article reaction compared to known standards.

PVS-RIPO Purified Sterile Bulk Lot L0904009 was tested for VERO genomic DNA load using a TaqMan®-based qPCR amplicon targeting the *Cercopithecus aethiops* (VERO) specific nectin-1a gene intra-gene duplication, a single-copy gene (GenBank® Accession No. AF308635). TaqMan® primers and a dual fluorescent dye-labeled probe were designed with ABI Primer Express software (Version 2.0.0). The 111-bp amplicon consists of a forward primer: 5'-(CCT CTG CCC AGC GTG AAG; SEQ ID NO: 5); reverse primer: 5'-(CAC AGA CAC GCC CAT GGA T SEQ ID NO: 6); and TaqMan® probe: 5'-[6FAM]-(CAC CCA AGC CAC CAA TGG CTC CAA)-[TAMRA] SEQ ID NO: 7. Primers and probe were diluted to 10 and 5 pmol/μL respectively with nuclease free water (NFW). The reaction mixture consisted of 25 μL TaqMan® PCR 2× Master Mix with UNG and ROX dye, 2 μL NFW, 1 μL forward primer, 1 μL reverse primer, 1 μL TaqMan® probe and 20 μL sample (50 μL final reaction volume). Reaction mixtures were loaded into a 96-well plate, covered with optical film, and amplified with an ABI model 7900HT 96-well Sequence Detection System using a 2-step qPCR profile (2:00 min, 50.0° C.; 10:00 min, 95.0° C.; 40 cycles of 0:15 min, 95.0° C.; 1:00 min, 60.0° C.). A VERO genomic DNA standard curve made from purified DNA (ATCC, Part #1587D) was 10-fold serial-diluted into NFW from 100 ng to 1 pg. Positive response from the 10 and 1 pg/rxn standards, equivalent to approximately 2.6 and 0.26 gene copies/rxn, are rarely observed. Total test sample DNA was inactivated 1:2 with buffer AL and extracted using a Qiagen DNA mini-prep method prior to the qPCR reaction. Potential PCR inhibition due to sample composition was monitored by spiking 5 ng of genomic DNA into the extracted test article sample. Efficiency of extraction was monitored through the use of a PBS buffer blank and a PBS buffer sample spiked with the equivalent of 100 pg VERO gDNA per qPCR reaction. A buffer (NFW no template) control sample was performed for the test. Contamination (sentinel) controls are included periodically. The initial genomic DNA contamination level in the test sample was calculated using the ABI 7900HT software by comparing the sample threshold cycle value with the human DNA standard curve equation. The initial DNA level was converted to pg DNA/mL using the formula: Sample dilution factor (2)*[(Average Test Sample Mass (pg)−Average No Template Mass (pg))÷(Average Pre-extraction Spike Recovery Efficiency (set to 100% if the extraction control has 10% recovery))]÷[(Sample Volume, μL per Reaction (20 μL))*1000 μL per mL].

The PVSRIPO virus harvest pool was Benzonase® enzyme treated prior to purification. Nuclease treatment typically generates average oligonucleotide fragments 12 nucleotides, with the post-digestion fragment population following a chi distribution. The *C. aethiops* (Vero and CV-1 cell lines) nectin-1 qPCR amplicon used in this assay was 111 bp. The result generated from the assay represents a worst-case estimate for residual host cell DNA concentration based on the mass of intact haploid *C. aethiops* genomic DNA (~3.88 pg/haploid copy).

c. Residual Benzonase® Enzyme

Because Benzonase® endonuclease was used in the purification process to produce the PVSRIPO Purified Sterile Bulk Lot L0904009, a test sample was examined using approved procedures to determine the residual level of Benzonase® endonuclease. The concentration of residual Benzonase® endonuclease was determined using the Merck KGaA Benzonase® endonuclease ELISA Kit II. The assay was initiated by adding the standards, samples, and controls to microtiter strips which were pre-coated with affinity purified polyclonal capture antibody. The wells were incubated at room temperature for a two hour period and then washed. A secondary horseradish peroxidase (HRP) conjugated antibody directed against the Benzonase® endonuclease was added to each well and the plate incubated at room temperature for one hour. This resulted in the formation of the following sandwich complex: solid phase antibody-Benzonase®, endonuclease-HRP, conjugated antibody. The wells were washed and aspirated to remove any unbound reactants. Residual Benzonase® was detected by the addition of 3,3',5,5'-Tetramethylbenzidine (TMB), a HRP substrate, to each well. The wells were developed for a 15 minute incubation period. The resulting color intensity, which correlated to the amount of analyte, was quantitated using a calibrated Spectra MAX 340 plate reader. Accurate measurement was achieved by comparing the signal of the sample to the Benzonase endonuclease standards assayed at the same time. The positive controls were the Benzonase® endonuclease standards ranging from 0.25 to 10 ng/mL. The assay diluent was used as the negative control. The limit of detection of the assay was 0.25 ng/mL.

d. Total Protein by BCA

The detection of total protein in a solution that cannot be directly quantitated spectrophotometrically due to interference from nucleic acids and/or low protein concentrations can be accomplished through the use of a bicinchoninic acid (BCA) reaction and colorimetric quantitation at 562 nm. A water-soluble blue-purple colored reaction product is formed when $Cu+2$ is reduced to $Cu+1$ by the presence of protein under high pH conditions and two molecules of BCA chelate a single cuprous $Cu+1$ ion. The BCA $Cu+1$ chelate exhibits a λmax of 562 nm with absorbance strongly correlated over three logs (<0.5 µg/mL to >500 µg/mL) of protein concentration, although specific reaction conditions and instrumentation often limit the effective linear range to only two logs. The absorbance of a protein solution reacted with BCA in the presence of $Cu+2$ is known to be dependent upon the solution's aggregate protein structure, total number of peptide bonds, and the relative proportion of cysteine/cystine, tryptophan, and tyrosine residues in the solution.

The test sample, PVS-RIPO Purified Bulk Lot L0903007, in a buffer solution of 20 mM Tris, 42 mM NaCl was analyzed for total protein using the BCA assay. The test sample did not contain buffer components at concentrations that would interfere with a BCA assay and was taken prior to the addition of HSA to the PVS-RIPO Purified Bulk Lot L0903007. A BCA working reagent and a BSA stock solution and standard curve were generated from a Pierce BCA Protein Assay kit immediately prior to the assay. The lack of interference from the sample buffer was verified by the generation of a sample-BSA spike reaction that was generated by adding 100 µL of the test sample with 500 µL of BSA (50 µL/mL) and 400 µL of buffer diluent to 1 mL of BCA working reagent, for a 25 µg/mL effective spike concentration. Duplicate test samples of 100 µL were added to 900 µL of buffer diluent and 1 mL of BCA working reagent. Upon addition of BCA working reagent, samples and controls were incubated for two hours at room temperature prior to measuring absorbance at 562 nm. The spectrophotometer was set to zero (blank) using the buffer diluent-BCA working reagent sample. Each reaction was measured in duplicate, and the BSA standards averaged prior to further analysis. A linear regression fit of the BSA standard curve (0 µg/mL to 100 µg/mL) was generated with the result of $R2=0.989$, no point on the standard curve was found to be an outlier and the results were valid. Test sample replicates did not exhibit excessive variance compared to the averaged value. The control 25 µg/mL BSA spike sample exhibited a recovery of 114.61% (28.65 µg/mL total), indicating the sample composition did not interfere with the assay. The PVS-RIPO Purified Bulk Lot L0903007 test sample grand average was calculated as −0.0197 AU562 equating to a protein concentration below the level of detection (<1 µg/mL) when calculated using the BSA standard curve equation $X=(((Y-A)/B)*10)$, where "X" is the protein concentration, "Y" is the absorbance value, "A" and "B" are the curve parameters, and 10 refers to the use of 100 µL sample per reaction. The method's limit of quantitation is 5 µg/mL, therefore the test result is reported as <5 µg/mL protein as determined by BCA.

e. Differential Killing

Differential killing activity of PVS-RIPO Purified Sterile Bulk Lot L0904009 on U87-MG human glioblastoma and HEK 293 human embryonic kidney cells was determined. The assay was performed using the Promega CellTiter96® AQueous One Solution Cell Proliferation Assay with the (3-(4,5-dimethylthiazol-2-yl)-5-(3-carboxymethoxyphenyl)-2-(4-sulfophenyl)-2H-tetrazolium, inner salt (MTS) and an electron coupling reagent phenazine ethosulfate (PES).

To perform the assay, U87-MG cells were cultured in DMEM with L-Glutamine supplemented with 10% fetal bovine serum and 1% Non-Essential Amino Acids Solution. HEK 293 cells were cultured in DMEM with L-Glutamine supplemented with 10% FBS. The cells were plated in a 96-well plate at $4 \times 10^4$ cells/well ($4 \times 10^5$ cells/mL, 0.1 mL/well). Test articles were diluted to an initial estimated titer of $2 \times 10^7$ PFU/mL followed by serial 4-fold dilutions. The diluted virus samples (100 µL/well) were transferred into the plates with the cells. The final virus titer (MOI) of test articles ranged from approximately 50 to 0.0002 PFU/Cell (MOI calculated based on $TCID_{50}$). The plates were incubated at 37° C. in a 5% $CO_2$ and 80% humidity environment for 48 hours. After the 48 hour incubation period, CellTiter96® AQueous One Solution was added (20 µL/well) and incubated for another four hours at 37° C. in a 5% $CO_2$ and 80% humidity environment. SDS (25 µL/well of 10% solution) was added to the wells. The plates were read within five minutes at an absorbance of 490 nm on a plate reader (Molecular Devices). The background readings in the wells with cell growth medium only (no cells) were subtracted from the test sample well readings. The data were analyzed using a non-linear 4-parameter curve fit (SoftMax Pro from Molecular Devices). Controls used in the assay included PVSRIPO Toxicology Lot L0603006 (positive control) and cell growth medium (negative control).

f. Sterility (Direct Inoculation)

The PVSRIPO Purified Sterile Bulk Lot L0904009 and Final Vialed Product Lot L0904010 sterility test by the Direct Inoculation Method was performed.

g. Bacteriostasis/Fungistasis (Post-Sterility)

Bacteriostasis/Fungistasis (B & F) testing was performed on the PVSRIPO Purified Sterile Bulk Lot L0904009 post-sterility testing using the United States Pharmacopoeia (USP) immersion method according to 21 CFR 610.12. B & F testing was performed to ensure that any bacteriostatic and/or fungistatic activity inherent in the test article did not adversely affect the reliability of the sterility test method.

Stability of PVS-RIPO Purified Sterile Bulk Lot L0904009

The PVS-RIPO Purified Sterile Bulk Lot L0904009 was not placed into storage prior to vialing to produce the PVS-RIPO Final Vialed Biological Product Lot L0904010. Therefore, stability testing was not performed for the PVSRIPO Purified Sterile Bulk Lot L0904009 since it was vialed the same day as final filtration.

Final Vialed Product

The PVSRIPO Purified Sterile Bulk Lot L0904009, formulated in 50 mM Sodium Phosphate in 0.9% Sodium Chloride, pH 7.4+0.2% HSA was sterile filtered using a 0.2 µm PVDF membrane filter to produce the final vialed product. The final vialed product was manufactured and tested and maintained in accordance with current Good Manufacturing Practices (CGMP) as described in the United States Code of Federal Regulations, 21 CFR 210, 211, and 600, and FDA/ICH Guidelines as they pertain to the manufacture and testing of Phase I/II investigational products.

The PVSRIPO Purified Sterile Bulk Lot L0904009 was filled to produce the Final Vialed Product Lot L0904010. The filling operation was performed in a Biological Safety Cabinet (BSC) following approved procedures. Two mL-13 mm Type I Borosilicate glass vials were used (Wheaton Catalog Number 223683, Lot Number 1438174). The target dispensing volume for each vial was 0.57 mL (0.564 to 0.576 mL). In-process weight checks were performed.

After filling 442 vials, B2 Flurotec Westar RS stoppers (West Pharma Catalog Number 1970-0002, Lot Number J8281) were inserted, and crimping operations were performed. The integrity of the crimp was visually inspected during crimping operations and no vials were rejected.

Following completion of the filling, stoppering, and crimping operations, the unlabeled vials (442) were inspected.

Release testing, methods, and specifications for the PVS-RIPO Final Vialed Product Lot L0904010 are provided in the Certificate of Analysis below in FIG. 21. Methods used for testing the PVS-RIPO Final Vialed Product Lot L0904010 [except Virus Titer (TCID50 Assay), Endotoxin by LAL, and Virus Stability by rct40, Full Genome Sequence, and Sterility (Direct Inoculation)] are described below. Methods for Virus Titer (TCID50 Assay), Endotoxin by LAL, and Virus Stability by rct40 were described for the PVS-RIPO Harvest Pool Lot L0904008 and can be found herein. Methods for Full Genome Sequence and Sterility (Direct Inoculation) were described for PVS-RIPO Purified Sterile Bulk Lot L0904009 and can be found herein.

a. Appearance

A sample of the PVS-RIPO Final Vialed Product Lot L0904010 was examined visually. The product was examined for the integrity of the container, the clarity of the solution and the accuracy of the container label. The container was inspected for any cracks or deterioration, and to assure that the top was securely closed. The clarity of the solution was evaluated by visual inspection to determine if the soluble product in the liquid formulation was free from any particulate matter, opaqueness, and tint of fluid in the container, or any turbidity or cloudiness of the fluid in the container. The container label was inspected to confirm that the cryovial was appropriately labeled and the label was securely applied.

b. RT-qPCR (HRV-2 IRES and Polio Polyprotein)

The Recombinant Poliovirus PVSRIPO Final Vialed Product Lot L0904010 was tested for PVSRIPO HRV-2 IRES (PVS-1), and Polio Polyprotein (P01) RNA load using a TaqMan®-based RT-qPCR amplicon targeting the HRV-2 IRES (PVS-1) and Polio polyprotein genes (P01) in PVSRIPO. Real-time quantitative PCR (qPCR) is a sensitive quantitative amplification method that can be utilized for gene expression analysis, genotyping, pathogen detection/quantitation, mutation screening and precise DNA detection, including the quantitation of low copy residual DNA or RNA in a sample. The Process Analytics/Biopharmaceutical Quality Control laboratory used an Applied Biosystems 7900HT 96-well instrument to detect the accumulation of PCR amplification product continuously during the amplification process, allowing accurate target quantitation in the exponential phase of PCR. The use of a 96-well block allowed for greater reaction volumes than a 384-well block and thus increased the assay sensitivity for residual DNA and contaminant DNA studies.

TaqMan® qPCR chemistry utilizes a dual-labeled fluorogenic oligonucleotide TaqMan® probe with each amplicon. The TaqMan® probe used for detection of human genomic DNA are composed of an oligonucleotide end labeled with two fluorescent dyes with distinguishable emission maxima. The probe 5' terminus is labeled with a reporter dye, 6-Carboxyfluorescein (6-FAM), and the 3' probe terminus is labeled with a quenching dye, Carboxytetramethylrhodamine (TAMRA). The oligonucleotide probes are homologous to internal target sequences within the PVSRIPO HRV-2 derived IRES and the Polio Polyprotein RT-PCR amplicons and when used together are specific for PVSRIPO. Since PVSRIPO is a single-stranded RNA virus, samples are reverse transcribed using the amplification primers to cDNA as part of the thermocycle protocol prior to qPCR amplification. While intact and in free solution, the probe quenching dye reduces the fluorochrome reporter emission via fluorescent resonant energy transfer (FRET). During the extension phase of a TaqMan® PCR reaction the probe is cleaved by the 5' nuclease activity of the Taq DNA polymerase, releasing the reporter dye from the probe and allowing an increase in reporter emission.

The ABI Prism 7900HT uses a dual-axis scanning head to distribute the excitation light from an argon-ion (488 nm) laser to all 96 wells. A CCD imager measures the fluorescence spectrum and intensity from each well to generate real-time spectral data during PCR amplification. ABI Sequence Detection Software (SDS) deconvolutes the fluorescence intensity of reporter, quencher, and normalizer (ROX) dyes and calculates the increase in normalized reporter emission intensity over the course of the amplification.

Precise quantification of initial target in each PCR reaction occurs during the exponential (log 2) phase of the amplification prior to reagent exhaustion or by-product inhibition of the reaction. However due to signal to noise limits of the reaction and general background fluorescence, the most accurate data are typically generated late in log phase. Normalized reporter fluorescence is plotted versus time, represented by the PCR cycle number. Target copy numbers or mass values are generated by assigning a fluorescence threshold above background and determining the cycle point at which each sample's amplification plot reaches the threshold (defined as the threshold cycle or Ct). Threshold cycle values for each reaction are used to quantitate the amount of target initially contained within each test article reaction compared to known standards.

To perform the assay at the BDP, TaqMan® primers and a dual fluorescent dye-labeled probe were designed with ABI Primer Express software (Version 2.0.0). The 71-bp HRV-2 RES (PVS-1) amplicon consists of a forward primer: 5'-(AAC CCA ATG TGT ATC TAG TCG TAA TGA, SEQ ID NO: 1); reverse primer: 5'-(TGA AAC ACG GAC ACC CAA AG SEQ ID NO: 2); and TaqMan® probe: 5'-[6FAM]-(CAA TTG CGG GAT GGG ACC AAC T SEQ ID NO: 3)-[TAMRA]. The 70-bp amplicon for P01 consists of a forward primer: 5'-(TTG GTG GGA ACG GTT CAC A SEQ ID NO: 8); reverse primer: 5'-(TCA CCT TGA CTC TGA GTG AAG TAT GA SEQ ID NO: 9); and TaqMan® probe: 5'-[6FAM]-(TTG CAG CGG CCC TGA AGC G SEQ ID NO: 10)-[TAMRA]. Primers and probes were diluted to 10 and 5 pmol/μL respectively with nuclease free water (NFW). The reaction mixture consisted of 25 μL TaqMan® 1-step RT PCR 2× Master Mix with ROX dye, 1 μL RNase inhibitor, 1 μL NFW, 1 μL forward primer, 1 μL reverse primer, 1 μL TaqMan® probe and 20 μL test sample (50 μL final reaction volume). Reaction mixtures were loaded into a 96-well plate, covered with optical film, and amplified with an ABI model 7900HT 96-well Sequence Detection System using a 3-step qPCR profile (2:00 minutes, 50.0° C.; 30 minutes at 48.0° C. (RT-step); 10:00 minutes, 95.0° C.; 40 cycles of 0:15 minutes, 95.0° C.; 1:00 minutes, 60.0° C.). Amplicon cDNA standard curves were made from PVSRIPO plasmid DNA and were 10-fold serial-diluted into NFW from 1 ng to 10 fg. Total test sample RNA was inactivated 1:4 with buffer AVL and extracted using a Qiagen Viral RNA mini-prep method prior to the RT-qPCR reaction. Potential PCR inhibition due to sample composition was monitored by spiking 500 pg of PVSRIPO plasmid DNA into the extracted test sample. A buffer (NFW no template) negative control sample was performed for the test. PVSRIPO plasmid DNA Lot L0305006 was used as a positive control. Both PVSRIPO amplicons were run on the same 96-well plate to eliminate inter-assay variation. The initial PVSRIPO RNA concentration in the test sample was calculated using the ABI 7900HT software by comparing the sample threshold cycle value with the plasmid DNA standard curve equation. The initial RNA level was converted to pg RNA/mL using the formula: Sample dilution factor (2)*[(Average Test Sample Mass (pg)−Average No Template Mass (pg))÷(Average Pre-extraction Spike Recovery Efficiency (set to 100%))]÷[(Sample Volume, μL per Reaction (20 μL))*1000 μL per ml].

c. pH pH testing was performed on the PVSRIPO Final Vialed Product Lot L0904010. The pH value was obtained from a properly standardized potentiometric instrument (pH meter) capable of reproducing pH values to 0.02 pH unit using an indicator electrode sensitive to hydrogen-ion activity, the glass electrode, and a suitable reference electrode. The instrument is capable of sensing the potential across the electrode pair and able to control the change in millivolts per unit change in pH reading through a temperature and/or slope control. Measurements are made at 25±2° C. To perform the assay, the pH meter was standardized using two sets of two standardization buffers: pH 4.0 and 7.0, and pH 7.0 and 10.0. The probe was then rinsed and blotted dry before determining the pH of the test sample. The assay was valid because the slope value of the two standardizations fell within the range of 92.0%-102.0%. The positive controls were pH 4.0 standard, pH 7.0 standard, pH 10.0 Standard.

e. Ratio of Virus Particles Per Infectious Units

The ratio of virus particles per infectious units (vp/IU) was calculated for the PVS-RIPO Final Vialed Product Lot L0904010 by dividing the virus particle concentration, 1.01×1011 vp/mL (QC-042172) by the virus titer, 3.98×109 TCID50/mL (QC-042165).

f. Stability Testing

1. PVSRIPO Final Vialed Product Lot L0904010

Stability testing of PVSRIPO Final Vialed Product Lot L0904010 is being conducted under Protocol SP-137 for a four year time period. Vials designated for stability testing are stored in controlled storage at ≤−70° C. Attributes of the final vialed PVS-RIPO product tested for stability include visual appearance, potency (virus titer by $TCID_{50}$), and safety (Endotoxin/LAL, pH and Bioburden). Appearance and virus titer by $TCID_{50}$ are tested at the 0, 6, 12, 24, 36, and 48 month stability time points. Safety (Endotoxin/LAL, pH and Bioburden) testing is performed at 0, 12, 24, 36, and 48 month stability time points. A summary of the stability data collected through the 6-month stability time point for the PVSRIPO Final Vialed Product Lot L0904010 is included in Table 8. The results indicate that the PVSRIPO Final Vialed Product Toxicology Lot L0904010 is stable at ≤−70° C. for 6-months.

TABLE 8

PVSRIPO Final Biological Product Lot L0904010 Stability Results

| Test | Specification | 0 Months | 6 Months |
|---|---|---|---|
| Appearance | Clear to translucent, colorless liquid with no evidence of particulate matter | Clear, colorless liquid with no particulate matter QC-042169 | Clear, colorless liquid with no evidence of particulate matter QC-045043 |
| Virus Titer by $TCID_{50}$ | Report Results | 9.60 $TCID_{50}$/mL~3.98 × $10^9$ IU/mL QC-042165 | 9.56 $TCID_{50}$/mL~3.63 × $10^9$ IU/mL QC-045044 |
| Endotoxin/ LAL | Report Results | <0.05 EU/mL QC-042163 | Not Required |
| pH | Report Results | 7.4 QC-042171 | Not Required |
| Bioburden | No Growth | No Growth (Sterility) QC-042174 | Not Required | d. Virus Particle by Electron Microscopy (EM)

This assay, designed to quantitate the number of viral particles/mL in a test sample (PVSRIPO Final Vialed Product Lot L0904010) by negative stain electron microscopy. Ten grid spaces were photographed and the number of viral particles in each section were enumerated and used to calculate the viral particles/mL. The test sample was fixed by dilution with an equal volume of fixative (8% formaldehyde in 2×PBS). The test sample (0.5 μL) was placed on a Formvar-treated/carbon coated grid and allowed to air dry. The sample was then washed with 5 μL of double distilled water (DDH2O) to wash salt/phosphate buffer from the sample. Then 1% phosphotungstic acid (PTA, pH 7.0) aqueous solution was added (0.5 μL) onto the grid and allowed to air dry. The grid was examined by electron microscopy. Ten grid spaces were photographed and the number of viral particles determined by the following calculation:

virus particles (vp)=(average #vp)×(area of grid/area of photo)×(1 mL/the amount of virus added in μL)

2. PVSRIPO Final Vialed Product Toxicology Lot L0603006

A previous pilot lot (PVS-RIPO Toxicology Lot L0603006) was manufactured. PVS-RIPO Toxicology Lot L0603006 was used in the Range-Finding Study of PVS-RIPO in Cynomolgus Monkeys. PVS-RIPO Toxicology Lot L0603006 was manufactured using a process equivalent to the Clinical Lot L0904010 differing only in issues related to process scale. The Certificate of Analysis for PVS-RIPO Toxicology Lot L0603006 is included in FIG. 22.

Stability testing of the PVS-RIPO Final Vialed Product Lot L0603006 stored at ≤−70° C. was conducted for 48-months. The protocol was revised to remove the virus particle by electron microscopy assay (because the method is not considered stability indicating), to remove determination of the ratio of virus particles to infectious units (Ratio VP/IU), and to add annual bioburden testing. A summary of the complete stability data collected through the 48-month stability time point for the PVSRIPO Final Vialed Product Toxicology Lot L0603006 is included in Table 9. The results indicate that the PVSRIPO Final Vialed Product Toxicology Lot L0603006 is stable at ≤−70° C. for 48-months.

TABLE 9

PVSRIPO Final Biological Product Lot L0603006 Summary of Stability Results

| Test | Specification | 0 Months | 3 Months | 6 Months | 9 Months | 12 Months | 18 Months |
|---|---|---|---|---|---|---|---|
| Appearance | Clear to translucent, colorless liquid with no evidence of particulate matter | Clear, colorless liquid with no foreign or particulate matter QC029922 | Clear, colorless liquid with no particulates or foreign matter QC030997 | Clear, colorless liquid with no particulates or foreign matter QC031806 | Clear, colorless liquid with no particulates or foreign matter QC032908 | Clear, colorless liquid with no particulates or foreign matter QC033759 | Clear, colorless liquid with no particulates or foreign matter QC035751 |
| Virus Titer by $TCID_{50}$ | Report Results | 10.31 $TCID_{50}$/mL ~2.05 × $10^{10}$ IU/mL QC029921 | 10.09 $TCID_{50}$/mL ~1.22 × $10^{10}$ IU/mL QC030998 | 10.49 $TCID_{50}$/mL ~3.12 × $10^{10}$ IU/mL QC031807 | 10.27 $TCID_{50}$/mL ~1.88 × $10^{10}$ IU/mL QC032909 | 10.61 $TCID_{50}$/mL ~4.10 × $10^{10}$ IU/mL QC033760 | 10.27 $TCID_{50}$/mL ~1.88 × $10^{10}$ IU/mL QC035752 |
| Virus Particle by EM[1,2] | Report Results | 3.98 × $10^{12}$ vp/mL QC029928 | 5.71 × $10^{12}$ vp/mL QC030999 | 2.2 × $10^{13}$ vp/mL QC031808 | 3.6 × $10^{11}$ vp/mL QC032910 | 3.6 × $10^{12}$ vp/mL QC033761 | Not Required |
| Ratio VP/IU[1] | Report Results | 194 | 468 | 705 | 19.1 | 88 | Not Required |
| Endotoxin/LAL | Report Results | 0.0859 EU/mL QC029925 | Not Required | Not Required | Not Required | 0.184 EU/mL QC033762 | Not Required |
| pH | Report Results | 7.4 QC029923 | Not Required | Not Required | Not Required | 7.4 QC033763 | Not Required |
| Bioburden[3] | No Growth | Not Required | Not Required | Not Required | Not Required | Not Required | Not Required |

| Test | 24 Months | 30 Months | 36 Months | 42 Months | 48 Months |
|---|---|---|---|---|---|
| Appearance | Clear, colorless liquid with no particulates or foreign matter QC037473 | Clear, colorless liquid with no evidence of particulate matter QC039019 | Clear, colorless liquid with no evidence of particulate matter QC040161 | Clear, colorless liquid with no evidence of particulate matter QC041966 | Clear, colorless liquid with no evidence of particulate matter QC043800 |
| Virus Titer by $TCID_{50}$ | 10.18 $TCID_{50}$/mL ~1.50 × $10^{10}$ IU/mL QC037474 | 10.31 $TCID_{50}$/mL ~2.04 × $10^{10}$ IU/mL QC039020 | 10.12 $TCID_{50}$/mL ~1.32 × $10^{10}$ IU/mL QC040162 | 9.82 $TCID_{50}$/mL ~6.61 × $10^{9}$ IU/mL QC041967 | 9.86 $TCID_{50}$/mL ~7.24 × $10^{9}$ IU/mL QC043801 |
| Virus Particle by EM[1,2] | Not Required | Not Required | Not Required | Not Required | Not Required |
| Ratio VP/IU[1] | Not Required | Not Required | Not Required | Not Required | Not Required |
| Endotoxin/LAL | <0.5 EU/mL QC037475 | Not required | <0.5 EU/mL QC040163 | Not required | <0.5 EU/mL QC043802 |
| pH | 7.5 QC037476 | Not required | 7.1 QC040164 | Not required | 7.7 QC043803 |
| Bioburden[3] | Not Required | Not Required | No Growth QC040165 | Not Required | No Growth QC043804 |

[1] The Virus Particle by EM and the Ratio VP/IU tests were removed from Stability Protocol
[2] Aggregation of samples was noted during completion of this assay and an optimized sample preparation procedure is being evaluated. Therefore, sample handling/preparation differed at 0, 3, and 6 months; To date, the values from the test results are 12.5 logs +/− 1 logs.
[3] The Bioburden test was added to Stability Protocol SP-043 in Revision 02. The change to the protocol was reflected beginning at the 30-month stability time point.

Vial labels were generated and one label was attached to each vial. This process yielded 435 labeled filled vials. The labeled vials were boxed and placed into storage at ≤−70° C. Samples (52 labeled vials) were designated for BQC release testing. The remaining 383 labeled vials were designated as product. The 383 product vials were transferred to controlled storage at ≤−70° C.

One bag label was inserted into each of 383 Minigrip bags. Thirty-six Minigrip bags (each containing the inserted bag label) were placed into each labeled packaging box. The labeled packaging boxes were placed into a Biological Safety Cabinet (BSC) onto a tray filled with dry ice and allowed to cool and remain on dry ice throughout the packaging operations. A total of 383 PVSRIPO Final Vialed Product Lot L0904010 labeled vials were withdrawn from controlled storage at ≤−70° C. and placed in the same BSC on dry ice. This included 349 product vials, 3 retains and 31 product vials designated for stability testing. Each PVSRIPO Final Vialed Product Lot L0904010 vial was placed into an individual minigrip bag (each containing the inserted bag label).

Each box of packaged vials along with absorbent material was placed into a Biohazard bag and returned to ≤−70° C. storage. A total of 383 vials were placed into controlled storage at ≤−70° C.

Example 6

Chemistry, Manufacturing, and Control Amendment for PVSRIPO Final Vialed Product Lot L1402001

FIG. 23 provides a history of the PVSRIPO Final Vialed Product lots produced by the Applicant. The PVSRIPO Final Vialed Product Lot L1402001 was manufactured using the same procedures described in Example 5, with the following changes. Real-time RT-qPCR testing was used during the Sepharose 6 FF chromatography step to identify fractions containing high titer ($\geq 1 \times 10^7$ copies/mL) PVSRIPO viral RNA. This resulted in a slightly different range of fractions being selected which resulted in higher residual protein and free-viral RNA for this lot. It also allowed for an increase in the total infectious ($TCID_{50}$ IU) viral yield by a factor of approximately 6. Two additional *mycoplasma* tests were added to the Harvest pool testing. One was a test for detection of *mycoplasma* for viral products using Vero cells and the other detection of *mycoplasma* by Touch-down (TD)-PCR. All *mycoplasma* tests were performed for the Harvest pool initially used Vero cells instead of NIH/3T3 cells. The assay was subsequently performed using NIH/3T3 cells which are refractory to infection by PVSRIPO. A touch-down PCR assay was also performed to verify the absence of *mycoplasma* DNA following frozen sample storage. An additional RT-qPCR test for the Polio virus IRES was added to the final vialed product release testing to ensure the absence of wild type virus. The genomic sequencing method for the Purified Sterile Bulk and Final Vialed Product release tests used Illumina Next Generation Sequencing (NGS) method.

Figure 24:
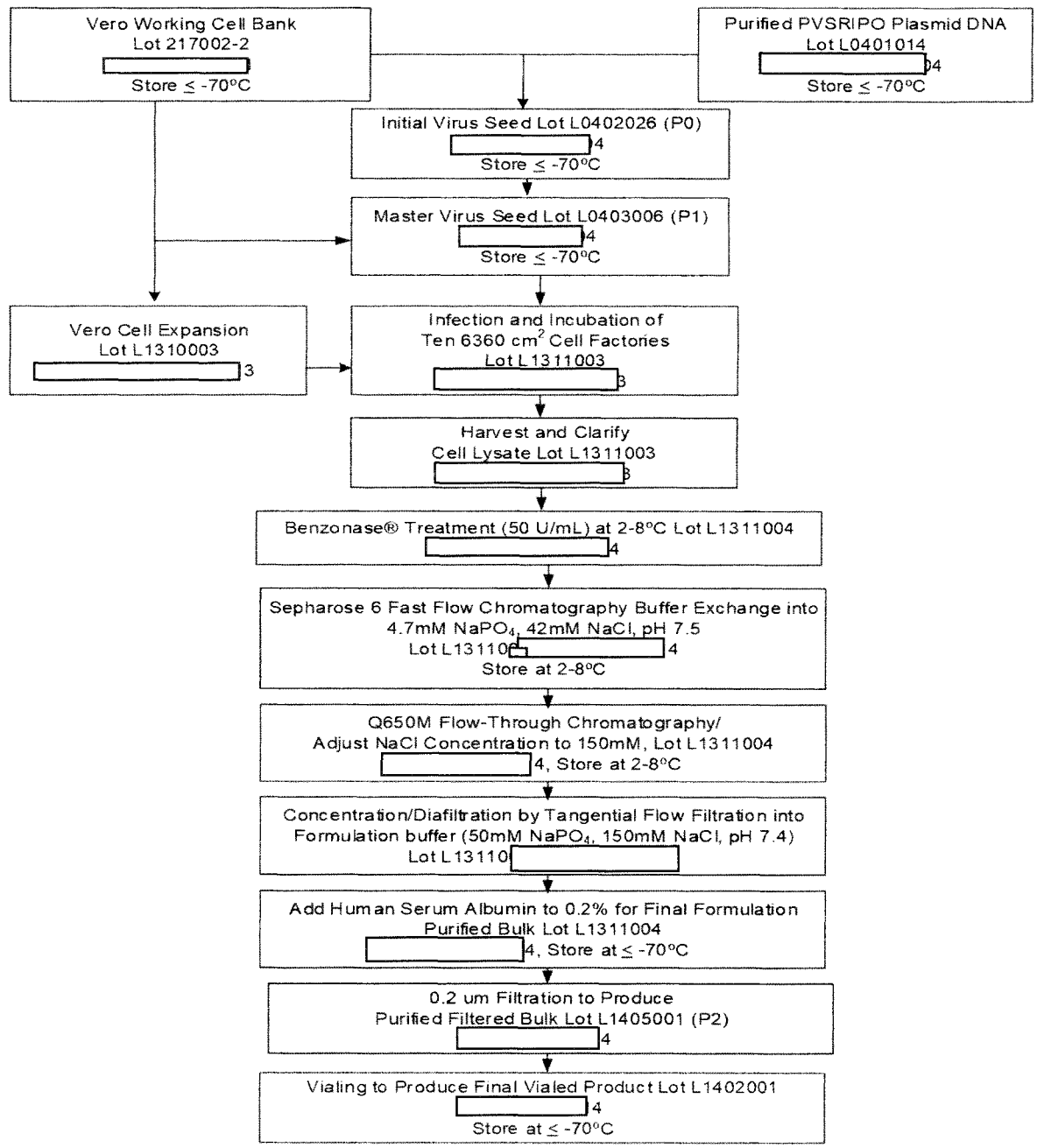
FIG. 24 is a flow chart showing the production process summary for final vialed product Lot L1402001.

FIG. 24 provides an overview of the manufacturing process. PVSRIPO Final Vialed Product Lot L1402001 was made from the same Master Virus Seed Lot L0403006 and Vero Working Cell Bank Lot 217002-2 as used for the previous PVSRIPO Final Vialed Clinical Lot L0904010. Following the same procedures as used for the previous clinical lot (see Example 5), Vero cells were expanded and infected with the master virus seed in ten tier cell factories. The virus was harvested by centrifugation and pooled. The harvest pool was treated with Benzonase® enzyme to reduce the level of host genomic DNA and purified using two column chromatography steps (Sepharose 6 FF chromatography and Q650M Flow-Through chromatography). The material was then concentrated using an ultrafiltration hollow-fiber membrane and diafiltered against the formulation buffer (50 mM $NaPO_4$, 150 mM NaCl, pH 7.4). This material was frozen at $\leq -70°$ C. for approximately three months. After thawing, the material was pooled, 0.2 micron sterile filtered, and filled into 2 mL glass vials. A brief summary of the manufacturing process is outlined below.

The PVSRIPO final vialed product is a colorless liquid formulated in 50 mM sodium phosphate, 0.9% sodium chloride, pH 7.4 buffer containing 0.2% HSA(HSA). The PVSRIPO Final Vialed Product is filled at a volume of 0.5 mL per vial and a concentration of $4.48 \times 10^9$ $TCID_{50}$/mL ($2.2 \times 10^9$ $TCID_{50}$/vial). The product is stored at $\leq -70°$ C.

Production Materials

The production materials/reagents used in the manufacture of PVSRIPO Final Vialed Product Lot L1402001 were the same as those described in Example 5. The Benzonase® enzyme is of vegetable origin and produced by fermentation. Casein acid hydrolysate is used in the fermentation medium. Milk used for the production of casein acid hydrolysate is sourced from healthily animals from Australia and New Zealand under the same conditions as milk collected for human consumption. Casein acid hydrolysate is prepared with no other ruminant material than milk. The FBS was manufactured from Fetal Bovine blood collected in USDA inspected abattoirs located in the United States and was negative for bovine viruses tested. The HSA was purchased from Octapharma. The HSA is manufactured according to GMP regulations and fulfills the criteria of production and product testing according to U.S. and European Pharmacopoeia. All donations of plasma were individually tested and non-reactive to $HB_sAg$, HIV-1/HIV-2 Ab and HCV Ab. Each plasma pool was tested and found negative for $HB_sAg$, HIV-1/HIV-2 Ab and HCV-RNA by Polymerase Chain Reaction method (PCR). The trypsin was sourced from porcine pancreas glands collected from animals of Canadian origin. The animals receive ante- and post-mortem inspections under a veterinarian's supervision and are apparently free from infectious and contagious diseases. The raw material trypsin is irradiated. The vendor used bovine lactose as a diluent to achieve the 1:250 strength. This lactose is sourced from milk fit for human consumption from healthy cows of U.S. origin. The raw trypsin used in this production was tested and found negative for porcine parvovirus, *mycoplasma*, and PCV 1 and 2.

Production Summary

Figure 25A:
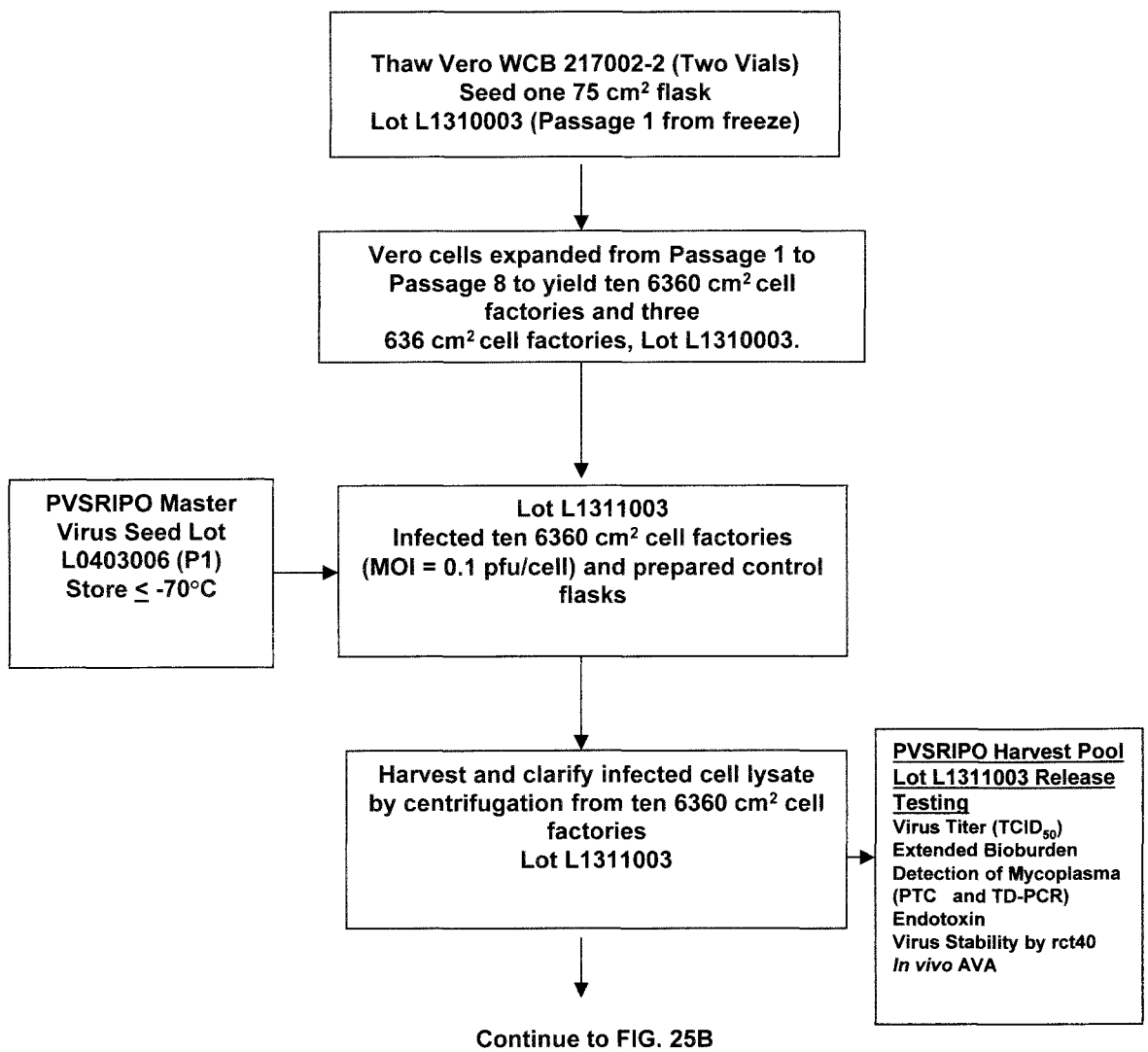
FIGS. 25A-25B is a process flow chart showing Cell Expansion Lot L1310003, Infected Cell Lysate Lot L1311003, and Purification of PVSRIPO Purified Sterile Bulk Lot L1405001.
Figure 25B:
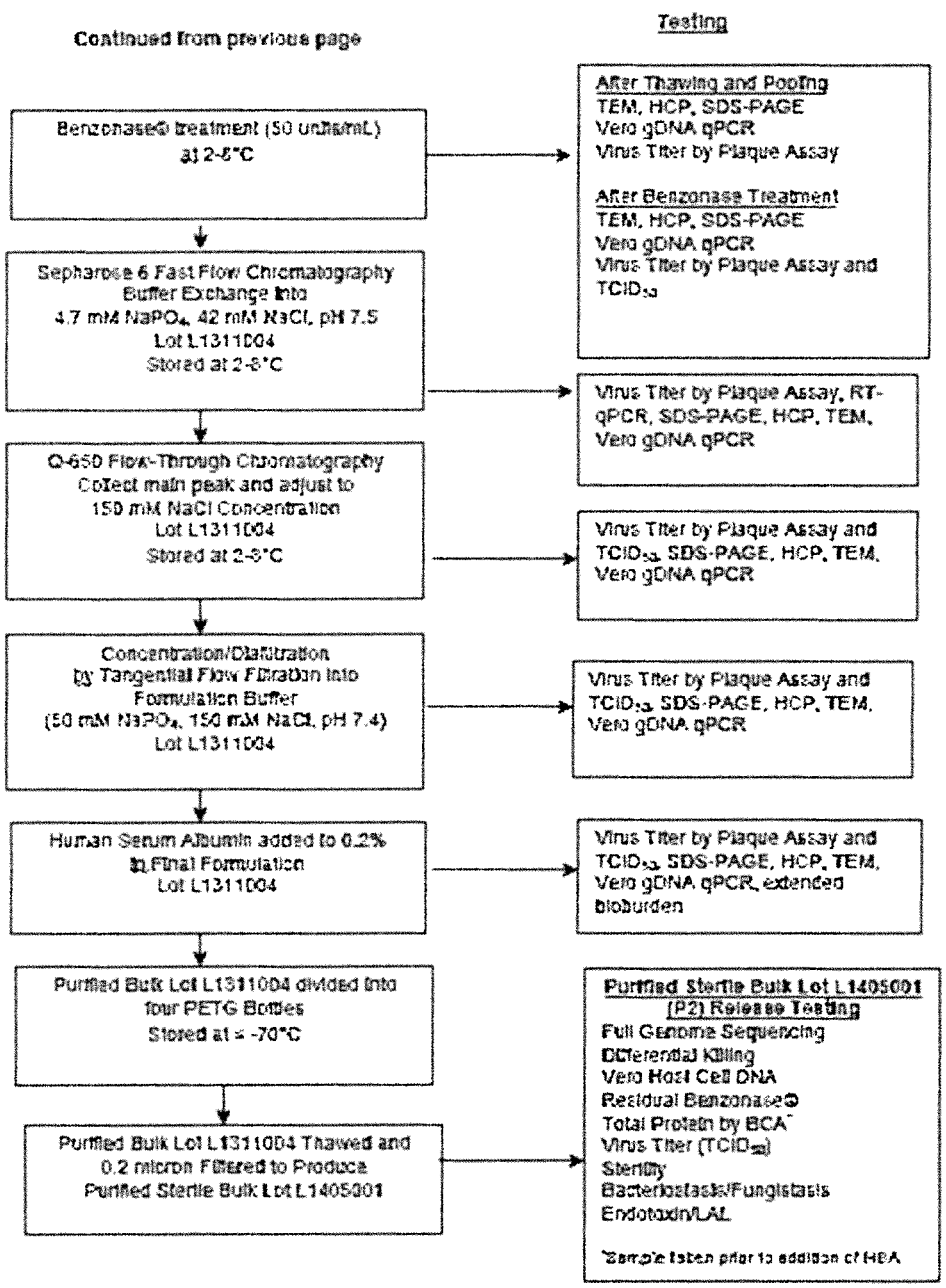

The manufacturing process to produce PVSRIPO Purified Sterile Bulk Lot L1405001 (P2) is illustrated in FIGS. 25A-25B. PVSRIPO Purified Sterile Bulk Lot L1311004 was manufactured at the BDP using the Vero Working Cell Bank (WCB) Lot 217002-2 and the MVS Lot L0403006 as the starting materials. Two vials of the Vero WCB Lot 217002-2 were expanded to produce cell expansion Lot L1310003 in ten 6360 $cm^2$ cell factories. The cell expansion Lot L1310003 was infected with the PVSRIPO MVS Lot L0403006 and the harvested material (Harvest Pool Lot L1311003) was used for the production of PVSRIPO Purified Sterile Bulk Lot L1405001.

a. Initiation and Expansion of Vero Cells

Vero cells from cell expansion Lot L1310003 were used for the production of cell harvest Lot L1311003. Cell expansion activities were performed at the BDP in the ATRF Building A, GMP Virus Production Facility. Throughout the expansion the Vero cells were grown in DMEM supplemented with L-glutamine and HEPES without Phenol Red. Fetal bovine serum (HyClone catalog #SH30070.03IR) was added at a concentration of 10%. Cells were incubated at a setting of 37° C. and 5% $CO_2$ for the entire cell expansion process.

Two vials of the Vero Working Cell Bank (WCB) Lot 217002-2 were thawed in a 37±2° C. water bath under constant agitation. The cells from each vial were added to 9 mL complete warmed medium in a 15 mL centrifuge tube. After mixing a sample was taken to count and determine the viability (79% and 84%). The cells were then centrifuged at a setting of 1000 rpm for 10 minutes at 4° C. After centrifugation the supernatant was discarded and the cell pellets were resuspended in a total combined volume of 30 mL DMEM media (as described above) in a 75 $cm^2$ flask. The cells were expanded from the 75 $cm^2$ flask up to 6360 $cm^2$ cell factories using the growth medium and conditions described above for a total of eight passages from the freeze.

An additional tumorigenicity test was performed on the EOP cells out 10 passages from the initial thaw to model additional scale-up passages needed for production. Porcine circovirus testing was also added. In addition, a test for the wild-type Polio Virus IRES was added.

b. Infection of Vero Cells Vero Cell Lot L1310003 (ten 6360 cm$^2$ cell factories, three 636 cm$^2$ cell factories) was used after confirming that each vessel contained healthy cells at 95-100% confluence and no visible signs of contamination to produce the infected cell lysate. Four PVSRIPO Master Virus Seed (MVS) Lot L0403006 bottles (125 mL PETG bottles with 80 mL MVS aliquots) were withdrawn from ≤−70° C. controlled storage, thawed in a 33-38° C. water bath, and used in the infection process at a multiplicity of infection (MOI) of 0.1 pfu/cell. Formulated infection medium was prepared by adding 226 mL of the thawed MVS Lot L0403006 to prepared Infection Medium (DMEM/F12 with L-glutamine without Hepes and Phenol Red) for a total volume of approximately 8 liters.

The ten 6360 cm$^2$ cell factories were prepared for infection by washing with approximately 750 mL of wash medium (DMEM/F12 with L-glutamine without Hepes and Phenol Red) and then filling with approximately 750 mL of the prepared formulated infection medium. Positive and negative controls were also prepared. Infected cell factories and controls were incubated at settings of 33° C., 5% CO$_2$ concentration and 80% humidity. At 70 hours post infection, 95-100% cytopathic effects (CPE) were noted in all ten cell factories and the expected results were noted in each of the control flasks.

c. Harvest and Clarification of Infected Cell Lysate

The PVSRIPO virus-infected cell suspension Lot L1311003 was harvested from each cell factory and pooled together into a sterile media bag. The infected cell suspension was sampled for release testing of the PVSRIPO Harvest Pool Lot L1311003. The Certificate of Analysis summarizing the tests, specifications, methods, and results of the PVSRIPO Harvest Pool Lot L1311003 release testing is included shown in FIG. 26.

The infected cell suspension was transferred into 1 L polycarbonate centrifuge bottles in approximately 750 mL aliquots. The infected cell suspension was centrifuged at a setting of 4° C. and 3800×g for approximately 20 minutes. The clarified supernatant from each of the centrifuge bottles was pooled together in a 10 L bag and dispensed into 10×1 L sterile PETG bottles, frozen, and transferred to MMIC for storage at ≤−70° C.

d. Benzonase® Treatment of Final Harvest

To reduce the level of host genomic DNA during the production of PVS-RIPO Purified Bulk Lot L1311004, the clarified PVS-RIPO Lot L1311003 harvest was thawed at room temperature for 21 hours after storage for approximately three months at ≤−70° C. The thawed PVS-RIPO was pooled into two 10 Liter bags and gently mixed. Three milliliter samples from each individual bag were combined into one 15 mL conical tube. Samples were taken from each bag for the following tests: TEM, Vero gDNA qPCR, plaque assay, HCP, SDS-PAGE, and full genomic sequencing.

Prior to the addition of Benzonase® enzyme, 100 mM MgCl$_2$ was added with mixing, to each bag (two bags) of the clarified PVSRIPO Lot L1311003 harvest to a 1 mM MgCl$_2$ final concentration. Benzonase® enzyme was added to each bag, with mixing, to a final concentration of 50 units/mL. Bags were incubated at 2-8° C. for 18-21 hours. The Benzonase® treated lysate was removed from 2-8° C. and sampled. The sample was analyzed by SDS-PAGE, full genomic sequencing, HCP, TEM, Vero gDNA qPCR, plaque assay and TCID$_{50}$.

e. Sepharose 6 Fast-Flow Chromatography

The Sepharose 6 FF Chromatography step provides buffer exchange and partial purification of the virus pool from low molecular weight host cell contaminants during the production of PVSRIPO Purified Bulk Lot L1311004. A chromatography column packed with Sepharose 6 Fast Flow (FF) resin (GE Healthcare-Biosciences, Piscataway, N.J.) was used to buffer exchange the virus into a low conductivity phosphate buffer in preparation for further purification. Prior to loading the Benzonase® treated lysate, the Sepharose 6FF column was flushed with 5M NaCl, charged with 4.7 mM NaPO$_4$, 1 M NaCl, pH 7.5 and equilibrated with 4.7 mM NaPO$_4$, 42 mM NaCl, pH 7.5.

The Benzonase® treated lysate was loaded onto the Sepharose 6FF column in two equal injections. The product was eluted with 4.7 mM NaPO$_4$, 42 mM NaCl, pH 7.5 and the PVS-RIPO main peak fractions from each injection were collected in several 2 L PETG bottles. Samples of the individual fractions from the two chromatographic runs were analyzed by real time reverse transcription qPCR (RT-qPCR). The PVS-RIPO main peak fractions were stored at 2-8° C. for 8-17 hrs. Selected fractions based on real-time RT-qPCR results and UV absorbance from both Sepharose 6 FF runs were pooled into a 20 L sterile bag. Samples of the pooled chromatography runs were analyzed for the following: plaque assay, RT-qPCR, SDS-PAGE, HCP, TEM and Vero gDNA qPCR.

f. Q650M Flow-Through Chromatography

After the Sepharose 6 FF step, the Lot L1311004 eluate was applied to a Q650M Flow Through chromatography column to remove the remaining host cell protein contaminants from the non-binding virus. The chromatography column was packed with Super Q 650M resin and prepared by flushing with 5M NaCl, followed by charging with 4.7 mM NaPO$_4$, 1 M NaCl, pH 7.5 and equilibration using 4.7 mM NaPO$_4$, 42 mM NaCl, pH 7.5.

The column was loaded with the PVS-RIPO Sepharose 6FF Main Peak and the flow through containing the virus product was collected. The buffer used during elution was 4.7 mM NaPO$_4$, 42 mM NaCl, pH 7.5. The NaCl concentration of the collected Q650M main peak was adjusted to 150 mM NaCl using 5M NaCl. The Q650M main peak material was sampled and then stored at 2-8° C. for approximately 16 hours. A sample was analyzed for the following: a plaque assay to determine virus titer, TCID$_{50}$, SDS-PAGE, HCP, TEM, and Vero gDNA qPCR.

g. Concentration and Diafiltration by Tangential Flow Filtration

The Q650M main peak Lot L1311004 material was removed from 2-8° C. storage and concentrated using an ultrafiltration hollow-fiber membrane (GE Healthcare UFP-50-C-4MA). The concentrated virus material was then diafiltered against the formulation buffer (50 mM NaPO$_4$, 150 mM NaCl, pH 7.4). Samples of the diafiltered PVS-RIPO solution were analyzed for: plaque assay to determine virus titer, TCID$_{50}$, SDS-PAGE, HCP, TEM, and Vero gDNA qPCR. HSA (25%) was added to the diafiltered PVS-RIPO Lot L1311004 to a final concentration of 0.2%. Samples of the formulated PVS-RIPO were analyzed for: extended bioburden, plaque assay, TCID$_{50}$, SDS-PAGE, HCP, TEM, and Vero gDNA qPCR.

h. Bulk Aliquot, Sampling and Storage of PVS-RIPO

The formulated PVS-RIPO Purified Bulk Lot L1311004 was moved into a class 100 BSC and dispensed into four 500 mL PETG bottles at a volume of approximately 3×250 mL and 1×167 mL each. The four bottles of PVS-RIPO Purified Bulk Lot L1311004 were labeled, frozen in an ethanol/dry ice bath, and stored at ≤−70° C. for further manufacturing use. The PVS-RIPO Purified Bulk Lot L1311004 was transferred to a controlled storage freezer at ≤−70° C.

i. Purified Sterile Bulk Lot L1405001 (P2)

3×250 mL and 1×167 mL bottles of the PVS-RIPO Purified Bulk Lot L1311004 were withdrawn from ≤−70° C. controlled storage in MMIC and transferred to ≤−70° C. Subsequently, the four bottles of the PVSRIPO Purified Bulk Lot L1311004 were thawed in a water bath at 21-25° C.; the room and product temperatures were 20° C. The total thaw time was 195 minutes. The contents of the four containers were pooled into a 2 L PETG bottle to yield a final total volume of 934.3 mL. A 2.5 mL sample of the purified PVS-RIPO was dispensed into 0.5 mL aliquots and stored at ≤−70° C. One hundred twenty two mL of freshly made 0.2% HSA in 50 mM NaPO$_4$, 150 mM NaCl, pH 7.4 was added to the pooled PVS-RIPO Purified Bulk Lot L1405001. PVS-RIPO Purified Bulk Lot L1405001 in 50 mM NaPO$_4$, 150 mM NaCl, pH 7.4 containing 0.2% HSA was pumped through a 0.2 micron sterile Millipak 20 (Millipore) filter that had passed pre-use integrity testing and had been pre-wetted with diluent (50 mM NaPO$_4$, 150 mM NaCl, pH 7.4+0.2% HSA). The filter was also flushed using the same diluent following product filtration yielding a total amount of 1,054 mL final filtered product. The filter passed post-filtration integrity testing. Using a sterile pipette, 27 mL of the Purified Sterile Bulk Lot L1405001 were removed and dispensed into sterile sample containers. Samples were submitted for Purified Sterile Bulk Lot L1405001 release testing leaving a total final volume of approximately 1027 mL. The Purified Sterile Bulk Lot L1405001 then proceeded to the filling step.

Vialing to Produce PVSRIPO Final Vialed Product Lot L1402001

The PVSRIPO Purified Sterile Bulk Lot L1405001 was filled to produce the Final Vialed Product Lot L1402001. The manual filling operation was performed in a Biological Safety Cabinet (BSC) following approved procedures. Two milliliter, 13 mm USP/EP Type I Borosilicate glass vials were used (West Pharmaceutical, Cat #6800314, Lot 6102124826). The target dispensing volume for each vial was 0.55 mL (0.545 to 0.556 mL). In-process weight checks were performed.

After filling 1792 vials, B2 Flurotec Westar RS stoppers (West Pharmaceutical, Cat #1970-0002, Lot D3161200) were inserted, and crimping operations were performed. The integrity of the crimp was visually inspected during crimping operations and five vials were rejected. Following completion of the filling, stoppering, and crimping operations, the unlabeled vials were inspected. Twenty-one unlabeled vials were rejected during inspection leaving a total of 1766 vials.

The process continued with labeling operations which yielded 1712 labeled filled vials for use after removal of 54 vials set aside for testing and retains. All vials were placed into labeled storage boxes and stored at ≤−70° C. Two additional vials were subsequently withdrawn for testing leaving 1710 vials.

PVSRIPO was packaged. Additional labels with the virus concentration were inserted into plastic Minigrip bags. Thirty-six Minigrip bags (each containing the inserted bag label) were placed into each labeled packaging box. The labeled packaging boxes were placed into a BSC onto a tray filled with dry ice and allowed to cool and remain on the dry ice throughout the packaging operations. A total of 1710 PVSRIPO Final Vialed Product Lot L1402001 labeled vials were withdrawn from controlled storage at ≤−70° C. and packaged into the Minigrip bags (one vial per bag) in the same BSC on dry ice. During the packaging into Minigrip bags, all vials and boxes were kept on dry ice. Each of thirty-six of the packaged vials were placed into labeled boxes. Boxes were placed into controlled storage at ≤−70° C.

Acceptable Limits and Analytical Methods

Tests and specifications for the PVSRIPO Harvest Pool, Purified Sterile Bulk, and Final Vialed Product were the same as described in Example 5, with the exception of the following changes. Two additional *mycoplasma* tests were added to the Harvest pool testing. One was a test for detection of *mycoplasma* for viral products using Vero cells and the other detection of *mycoplasma* by Touch-down (TD)-PCR. *Mycoplasma* detection for the Harvest pool initially used Vero cells instead of NIH/3T3 cells. The assay was subsequently performed using NIH/3T3 cells which are refractory to infection by PVSRIPO. A touch-down PCR assay was also performed to verify the absence of *mycoplasma* DNA following frozen sample storage. An RT-qPCR test for the Polio virus IRES was added to the final vialed product release testing to ensure the absence of wild type or vaccine strain polio virus. The genomic sequencing method for the Purified Sterile Bulk and Final Vialed Product release tests changed to the more advanced Illumina Next Generation Sequencing (NGS) method.

Release tests, methods, specifications, and results for PVSRIPO Harvest Pool Lot L1311003, Purified Sterile Bulk Lot L1405001, and Final Vialed Product Lot L1402001 can be found on the Certificates of Analysis in FIGS. 27-28.

Analytical Method Changes and Assay Descriptions

Testing of the PVSRIPO Harvest Pool, Purified Sterile Bulk, and Final Vialed product was performed as described in Example 5, with the exception that some additional *mycoplasma* tests were performed on the harvest pool sample. These methods along with the additional *mycoplasma* tests and new Next Generation Sequencing method are described below.

a. *Mycoplasma* for Viral Products Using Vero Cells

Detection of *mycoplasma* was performed on Harvest Pool Lot L1311003 using both an indirect and direct procedure. This test with the Vero cells was performed accidently on this harvest pool lot only; prior tests had used the NIH/3T3 cells which are refractory to Polio infection (the test on the NIH/3T3 cells was performed as well). Since the harvest pool samples used with the NIH/3T3 cells were stored frozen for an additional period of time relative to the Vero cell assay, a touch-down PCR (TD-PCR) assay was also performed to verify the absence of *mycoplasma* DNA in the harvest pool.

The indirect method of detection allows visualization of *mycoplasma*, particularly non-cultivable *mycoplasma*, by inoculation onto Vero cells and then staining using a DNA-binding fluorochrome stain. Both negative and positive controls were used in the assay. Positive controls included both a strong cyto-adsorbing (*M. hyorhinis*) and a poor cyto-adsorbing (*M. orale*) *mycoplasma* species. Staining the cultures with DNA-binding fluorochrome allows for the detection of *mycoplasma* based on the staining pattern observed. In the negative cultures only the cell nuclei fluorescence is observed, while nuclear and extra-nuclear fluorescence are observed in positive cultures.

Direct cultivation is a sensitive and specific method for the detection of *mycoplasma*. The agar and broth media used supply nutrients along with carbon and energy needed for the growth of cultivatable mycoplasmas. Both positive and negative controls were used in the direct assay. Positive controls included a fermentative *mycoplasma* (*M. pneumoniae*) and a non-fermentative *mycoplasma* (*M. orale*).

For the indirect method of detection, the harvest pool sample was thawed at 37±2° C. and 1:5 and 1:10 dilutions were prepared using sterile phosphate buffered saline. The undiluted test sample and each dilution were inoculated onto each of two coverslips (per sample/dilution) containing Vero cells. The coverslips were incubated for 1-2 hours at 36±1° C. and 5-10% $CO_2$. Then 2 mL of EMEM containing 8% fetal bovine serum was added to each coverslip. The coverslips were incubated at 36±1° C. and 5-10% $CO_2$ After 3 days of incubation, the coverslips were fixed, stained (Hoechst stain), and then read using an epifluorescent microscope.

Two milliliters of the undiluted test article was inoculated onto each of two SP-4 agar plates and 10 mL was inoculated into a 75 $cm^2$ flask containing 50 mL of SP-4 broth. The plates were incubated anaerobically at 36±1° C. for a minimum of 14 days. The flask was incubated anaerobically at 36±1° C. and subcultured on days 3, 7, and 14 onto each of two SP-4 agar plates (0.2 mL/plate). These plates were incubated anaerobically at 36±1° C. for a minimum of 14 days. The broth flask was observed each working day for 14 days for changes in color or turbidity. In general, growth of *mycoplasma* causes the broth to become turbid. The agar plates were observed after 14 days of incubation (Day 0). The SP-4 broth subcultured plates (Days 3, 7, and 14) were observed after 14 days of incubation. *Mycoplasma* colonies grow down into the agar causing the center of the colony to appear opaque and the peripheral surface growth to appear translucent. These colonies can be readily observed under a light microscope.

b. *Mycoplasma* by TD-PCR

Detection of *mycoplasma* was performed on Harvest Pool Lot L1311003 using Touchdown polymerase chain reaction (TD-PCR) test. This test was conducted in case the sample hold time at ≤−70° C. between the performance of the PTC *mycoplasma* Vero and NIH-3T3 cell tests may have resulted in a loss of any potential live *mycoplasma* in the retained harvest pool samples. The PCR based *mycoplasma* assay would be unaffected by the freeze-thaw and ultra-cold storage of the harvest pool retains.

PCR is a very sensitive tool for detection of *mycoplasma* DNA in cell, serum, or tissue samples. PCR amplifies the *mycoplasma* DNA regardless of its infectivity. By defining the borders of the selected conserved region of the *mycoplasma* sequence with a set of primers, it is possible to amplify the target sequence by a factor of greater than 10 million in a few hours. The presence of the amplified target DNA is confirmed by ethidium-stained gel electrophoresis. The assay can be used to detect as few as 1 cfu of *mycoplasma* DNA. Touchdown PCR is a modified cycling method that uses an annealing gradient to greatly increase specificity and sensitivity.

Test sample DNA is obtained by lysis of cells or supernatant and purification. The resulting DNA is resuspended in a volume of nuclease free water to generate 0.1 µg/µl of DNA. For PCR amplification, a master mix of reagents containing the appropriate primers, dNTPs, buffer, water, $MgCl_2$, and the Taq DNA polymerase were prepared and added to every reaction in the assay. Reactions were treated with 8-methoxypsoralen and exposed to U/V light to reduce occurrences of false priming events. Six aliquots of the test article were dispensed into PCR reaction tubes. Three aliquots were processed with no additional control DNA spiking. The other three aliquots were spiked with 1, 10, and 100 cfu of *mycoplasma* DNA. Four aliquots of reagent control were processed; one reaction contained all components of the reaction mix except sample. The other reaction tubes were spiked with 1, 10, and 100 cfu of *mycoplasma* DNA. One aliquot of purified human cellular H9 DNA was used as a negative control. Three aliquots of H9 DNA were spiked with 1, 10, and 100 cfu of *mycoplasma* DNA. After TD-PCR amplification, amplicons were separated by gel electrophoresis and examined by UV light.

c. Virus Titer ($TCID_{50}$)

The virus titer by $TCID_{50}$ was performed to determine the PVSRIPO virus titer in the PVSRIPO Harvest Pool, Purified Sterile Bulk, and Final Vialed Product using Hep-2C indicator cells. One hundred microliters (100 µL) of dilution medium (RPMI1640 with 4 mM L-Glutamine and 1% FBS) was added to each well of separate 96-well plates (providing separate plates for each reference standard, positive control and test samples). Initial dilutions of the FDA Poliovirus Type 1 Reference Standard, FDA Lot TA4 (1:10,000), Sabin Original Type 1 Positive Control Poliovirus (1:1,000,000) and Test Samples (1:1,000,000) were prepared with the dilution medium (RPMI1640 with 4 mM L-Glutamine and 1% FBS). A 100 µL aliquot of each final dilution was added to each of the eight wells in the first column of the respective 96-well plate. Using a calibrated multichannel pipettor, serial 1:2 dilutions were made in each 96-well plate by removing 100 µL from each well in column 1, transferring to the adjacent wells in column 2, mixing thoroughly and repeating the process for the next column in the series. For the FDA Reference Standard the dilution was terminated at column 11, with column 12 used as Negative Control wells (containing dilution medium only). The excess 100 µL from column 11 was discarded. For the Positive Control and Test Articles, the dilution scheme continued onto a second 96-well plate, terminating at column 23, with column 24 used as Negative Control wells. Ten thousand Hep-2C cells in growth medium (RPMI1640 with 4 mM L-Glutamine and 10% FBS) (0.1 mL at $1 \times 10^5$ cells/mL) were added to each well of each 96-well plate and incubated at 36±1° C. in a humidified, 5% $CO_2$ incubator for 10 days. The plates were examined for Cytopathic Effects (CPE) on Days 1, 3, 7 and 10. Upon completion of the assay, the number of wells exhibiting CPE for each sample was entered into the appropriate fields of the calculation program template provided by the FDA. The program calculates the $TCID_{50}$/mL for each sample, based on the response of the FDA Poliovirus Type 1 Reference Standard. Other well characterized PVSRIPO and Sabin-strain standards may be used as a positive control virus dependent on the availability of the FDA Reference Standard.

d. Virus Stability by rct40

The assay determines viral titer of PVSRIPO harvest pool and Final Vialed Product, and controls at 33° C., 36° C. and 40° C. by plaque formation on Vero indicator cells. The assay is an indirect measure of the stability of the virus using temperature related changes in growth properties as an indication of potential genetic changes. The assay is based on the WHO Technical Report Series No. 904, 2002. It states that the filtered bulk suspension of virus should be tested for the property of reproducing at temperatures of 36° C. and 40° C. in comparison with appropriate rct/40- and rct/40+ strains of poliovirus of the same viral type. The incubation temperatures should be controlled to within +0.1° C. The filtered bulk would pass the test if the titer of the bulk suspension and an appropriate reference standard at 36° C. was at least 5.0 logs greater than that determined at 40° C. All titers for the reference materials should be within the expected values.

The $log_{10}$ titers of the virus at 36° C. and 40° C. are compared and if the log reduction between 36° C. and 40°

C. is at least five, the sample is determined to be sensitive to growth at 40° C. and is considered to have passed the test. The titer of the sample at 33° C. is also determined so that it can be compared to the previously determined titer of the sample at 33° C. The positive controls include RCT 40+ control: Poliovirus 1 Sabin Clone S33 Lot L0406008 and RCT 40-Control: Poliovirus 1 Sabin Clone S71 Lot L0406004. The negative control is DMEM containing 10% FBS.

Vero cells were plated and allowed to grow until 80 to 100 percent confluence had been attained. The growth medium was removed and the Vero cells were dosed with 0.2 mL of test or control sample. Replicate dishes were then incubated at 33° C., 36° C. and 40° C. for approximately one hour. The inoculum was removed and the cell sheet overlaid with 1.5% agarose/2×EMEM/20% FBS. The agarose was allowed to solidify and replicate dishes were incubated at 33° C., 36° C. and 40° C. until plaques were fully formed in the positive controls (two days). The dishes were then overlaid with agarose/2×EMEM containing neutral red in the dark and the plaques were counted when the neutral red had stained the cell sheet. The mean plaque value was determined. The titer (pfu/mL) was calculated using the formula: Mean plaque value×dilution factor/volume inoculated.

e. Full Genome Sequence

Comprehensive deep sequence analysis of the PVSRIPO Purified Sterile Bulk and Final Vialed Product lots was performed.

1. RNA Extraction and Reverse Transcription

Genomic RNA was isolated from the test samples using the QIAamp Viral RNA Mini Kit from Qiagen (Germantown, Md.) as per a modified version of the standard Qiagen protocol. Briefly, 560 μl of Buffer AVL without Carrier RNA was added to 140 μl of the sample. The sample was vortexed and incubated at room temperature (23°±2° C.) for 10 minutes. Five hundred and sixty microliters of 100% ethanol was added to the sample, vortexed, and then half the sample (~630 μl) was added to the QIAamp Mini column and centrifuged for one minute at 6000×g. The rest of the sample was added to the column and the centrifugation was repeated. The column was then washed with two buffers. A double elution of 40 μl of elution buffer each was performed for a total final volume of about 80 μl. The total RNA was quantitated photospectometrically using a NanoDrop 8000 spectrophotometer. The RNA was then used to make cDNA using the ThermoScript™ RT-PCR System from Life Technologies (Carlsbad, Calif.). Briefly, 9 μl of RNA, 1 μl of oligo (dT)20 primer, and dNTPs were incubated at 65° C. for five minutes. Following incubation, cDNA synthesis buffer, DTT, RNase Out, and ThermoScript RT were added to the sample and the sample was incubated at 50° C. for 45 minutes, and then 85° C. for five minutes to terminate the reaction. RNase H was added to the sample and incubated at 37° C. for 20 minutes. The cDNA was quantitated photospectometrically using a NanoDrop 8000 spectro-photometer. A second strand reaction was then performed using the NEBNext Second Strand Synthesis Kit from New England BioLabs using 5 μl of the cDNA product. The cDNA was combined with second strand synthesis buffer and second strand synthesis enzyme mix and incubated at 16° C. for 2.5 hours. The product was purified using the QIAquick PCR purification kit from Qiagen and eluted in 30 μl of nuclease-free water (NFW). The ds-cDNA was quantitated photospectometrically using a NanoDrop 8000 spectrophotometer and stored at −20±4° C. for short-term storage.

2. Library Preparation

The prepared dscDNA was used to prepare libraries for sequencing on the Illumina HiSeq 2500. One library was prepared from each original sample. The libraries were prepared using the Nextera XT library preparation kit from Illumina (San Diego, Calif.). The starting total input of dscDNA was 1 ng for each library based on prior development range finding efforts using between 1 pg and 1 ng of input ds-cDNA. The libraries were prepared following the Illumina Nextera XT library preparation protocol. Briefly, each sample was fragmented enzymatically and tagged (ligated) with adapter sequences simultaneously using the Nextera Tagmentation chemistry. The process fragments the input DNA and adds adapter sequences to the ends of the fragments for use in downstream processing. The ligation enzyme was then neutralized and a brief, 12 cycle amplification was performed to add barcodes on to each sample at the 5' and 3' ends. Each library was assigned a different barcode to identify and delineate different samples during analysis. The PCR reactions were cleaned up using a double round of AMPure XP bead washes and then eluted in TE buffer. Each of the libraries was then analyzed on the Agilent Bioanalyzer using high sensitivity DNA chips to assess for quality and quantity of the libraries. The sample libraries were stored at −20±4° C. for short-term storage.

3. Illumina cDNA Sequencing and Analysis

For each sample, one Rapid flow cell was run on the Illumina HiSeq 2500. For each flow cell, the library was denatured and diluted for on-instrument clustering. Paired end 2×150 bp sequencing was then performed on each of the libraries using Illumina SBS sequencing technology and reagents. The resulting data was de-multiplexed using the Illumina HiSeq software and then analyzed. Each flow cell was run using a single sample. FastQ files were generated for all sequenced fractions. Samtools and mpileup software are used to convert the output files from a SAM to BAM format and index output files for viewing in the Integrated Genome Viewer. Mpileup was used with a flag to increase the depth of each position in order to examine coverages of the virus and look for potential variations. Since 12 cycles of PCR pre-amplification were required for the Nextera XT library preparation, the threshold for calling a viral sequence variant at a given position was established to be 212=4096 or 0.1% of reads, whichever was greater. Variants are defined according to the following criteria: if sequencing depth at a given base position was equal to or exceeds 4,096,000, potential variations were called at greater than 0.1%; if depth was less than 4,096,000 but greater than 4096, variants exceeding a frequency of 4096 or greater were called; if the depth of coverage at a given base position was less than 4096 reads, potential variants were called if they consisted of greater than 1.0%. The minimum read coverage per base position was set at 4× (regulatory minimum), before additional sequencing efforts (Illumina, Sanger, or other NGS methods) would be required.

Reads were aligned for each sample to the PVSRIPO reference sequence using Bowtie (short read reference aligner). The values for the total number of bases, the coverage, and the mean read length and the percent of reads aligned to the reference for each sample were calculated and compared to pre-established specifications for assay validity. The estimated genome coverage was found by taking the total sequenced bases and dividing by the size of the PVSRIPO reference sequence (7303 base pairs). Plots of coverage compared to location across the reference for each sample were prepared, as well as plots of sample read length for each sample. Analysis was performed to examine variants in each sample when compared to the reference sequence. Elevated levels of polymorphism were expected (and observed) at the 5' end (base positions 1-34) of each viral lot since this region of the Polio genome (VPg binding and Stem a/b) is known to exhibit high sequence variability in vivo. Non-aligned read sequences were analyzed by NCBI BLASTn to determine their identity; it is expected that non-aligned reads, especially those from unpurified viral samples, will be from Vero host cell genomic or mitochondrial DNA sequences, although rare human DNA or other laboratory contaminant DNA sequences may be observed as well.

f. Host Cell DNA

The PVS-RIPO Purified Sterile Bulk lot was tested for Vero genomic DNA load using a TaqMan®-based quantitative polymerase chain reaction (qPCR) (Applied Biosystems Inc., Foster City, Calif.) amplicon targeting the *Cercopithecus aethiops* (Vero) specific nectin-1α gene intra-gene duplication, a single-copy gene (GenBank® Accession No. AF308635). The limit of detection for the assay was <5 ng Vero genomic DNA per mL. Vero cell genomic DNA (gDNA) was used as the positive control (100 ng-10 pg) and a spike of the test article with ~2250 copies of the internal positive control (IPC) was used as the PCR inhibition control. Negative No Test Control (NTC) controls were performed using nuclease free water (NFW) and the nucleic acid extraction controls for each sample contained an equivalent of ~10,000 copies of the IPC per reaction. The IPC utilizes a VIC-labeled probe, allowing both the test and IPC amplicons to be quantitated in the same PCR reaction. The IPC results from the Vero host cell DNA method also serve as the extraction and inhibition controls for the concomitantly performed viral quantitation RT-qPCR methods.

Real-time qPCR is a sensitive quantitative amplification method that can be utilized for gene expression analysis, genotyping, pathogen detection/quantitation, mutation screening and precise DNA detection, including the quantitation of low copy residual DNA or RNA in a sample. An Applied Biosystems 7900HT 96-well instrument was used to detect the accumulation of PCR amplification product continuously during the amplification process, allowing accurate target quantitation in the exponential phase of PCR. The use of a 96-well block allows for greater reaction volumes than a 384-well block and thus increases the assay sensitivity for residual DNA and contaminant DNA studies.

TaqMan® qPCR chemistry utilizes a dual-labeled fluorogenic oligonucleotide TaqMan® probe. The TaqMan® probe used for detection of human genomic DNA is composed of an oligonucleotide end labeled with a fluorescent dye with a distinguishable emission maxima. The probe 5' terminus was labeled with a reporter dye, 6-FAM, and the 3' probe terminus was labeled with a quenching dye. The internal positive control (IPC) amplicon used a VIC-labeled probe with a non-fluorescent quencher to avoid emission interference from the target amplicon. The oligonucleotide probe was homologous to a target sequence within the *Cercopithecus aethiops* (Vero) nectin-1α gene PCR amplicon and is highly specific to Vero cells. A high rejection ratio of Vero to human gDNA was achieved by utilizing a nine base sequence duplication event unique to *C. aethiops* that is not present in human gDNA, as a portion of the probe target. While intact and in free solution, the probe quenching dye reduces the fluorochrome reporter emission via FRET. During the extension phase of a TaqMan® PCR reaction the probe was cleaved by the 5' nuclease activity of the Taq DNA polymerase, releasing the reporter dye from the probe and allowing an increase in reporter emission.

Precise quantification of initial target in each PCR reaction occurs during the exponential ($log^2$) phase of the amplification prior to reagent exhaustion or by-product inhibition of the reaction. However, due to signal to noise limits of the reaction and general background fluorescence, the most accurate data are typically generated late in log phase. Normalized reporter fluorescence is plotted versus time, represented by the PCR cycle number. Target copy numbers or mass values are generated by assigning a fluorescence threshold above background and determining the cycle point at which each sample's amplification plot reaches the threshold (defined as the threshold cycle or Ct). Threshold cycle values for each reaction are used to quantitate the amount of target initially contained within each test article reaction compared to known standards.

PVS-RIPO Purified Sterile Bulk was tested for VERO genomic DNA load using a TaqMan®-based qPCR (Applied Biosystems Inc., Foster City, Calif.) amplicon targeting the *Cercopithecus aethiops* (VERO) specific nectin-1α gene intra-gene duplication, a single-copy gene (GenBank AF308635). TaqMan® primers and a dual fluorescent dye-labeled probe are designed with ABI Primer Express software (Version 2.0.0). The 111-bp amplicon consists of a forward primer: 5'-(CCT CTG CCC AGC GTG AAG, SEQ ID NO: 5); reverse primer: 5'-(CAC AGA CAC GCC CAT GGA T, SEQ ID NO: 6); and TaqMan® probe: 5'-[6FAM]-(CAC CCA AGC CAC CAA TGG CTC CAA)-[Quencher], SEQ ID NO: 7. Primers and probe were diluted to 10 and 5 pmol/μL respectively with nuclease free water (NFW). The reaction mixture consisted of 25 μL TaqMan® PCR 2× Master Mix with UNG and ROX dye, 1.5 μL IPC amplicon primers/probe (or NFW), 0.5 μL IPC DNA (or NFW), 1 μL forward primer, 1 μL reverse primer, 1 μL TaqMan® probe and 20 μL sample (50 μL final reaction volume). Reaction mixtures were loaded into a 96-well plate, covered with optical film, and amplified with an ABI model 7900HT 96-well Sequence Detection System using a 2-step qPCR profile (2:00 min, 50.0° C.; 10:00 min, 95.0° C.; 40 cycles of 0:15 min, 95.0° C.; 1:00 min, 60.0° C.). A Vero genomic DNA standard curve made from a purified and optically quantitated DNA extract was 10-fold serial-diluted into NFW from 100 ng to 10 pg. A positive response from the 10 pg/rxn standard, equivalent to approximately 2.6 gene copies/rxn, is rarely observed. Total test sample DNA was extracted using an approved Qiagen detergent spin-column mini-prep method prior to the qPCR reaction. Potential PCR inhibition due to sample composition was monitored by spiking ~2250 equivalent copies of the IPC target DNA into the appropriate extracted test article samples (i.e., not samples previously spiked with IPC to monitor extraction efficiency). Efficiency of extraction was monitored through the use of test samples spiked with the equivalent of 10,000 copies of IPC DNA. Negative (NTC) control samples were performed for the test using NFW. All standards, test samples, IPC spikes, and control PCR reactions were performed in duplicate. Method controls and system suitability criteria must be met in order to report the sample results, including: NTC Ct scores, standard curve Ct scores and fit ($R^2$), and IPC extraction and interference spike recovery. The initial genomic DNA contamination level in the test sample was calculated using the ABI software by comparing the sample threshold cycle value with the Vero DNA standard curve equation.

The PVS-RIPO virus harvest pool was Benzonase® enzyme treated prior to purification. Nuclease treatment typically generates average oligonucleotide fragments ≤12 nucleotides, with the post-digestion fragment population following a chi distribution. The *C. aethiops* (Vero cell line) nectin-1 qPCR amplicon used in this assay is 111 bp in length. Therefore the result generated from the assay represents a worst-case estimate for residual host cell DNA concentration based on the mass of intact haploid *C. aethiops* genomic DNA (~3.88 pg/haploid copy).

RT-qPCR for Polio Virus IRES

The PVSRIPO Final Vialed Product lot was tested for the presence of wild-type Polio virus type-1 and type-2 IRES sequences using a TaqMan®-based reverse transcribed quantitative polymerase chain reaction (RT-qPCR) amplicon "POSA" targeting the native Polio IRES sequence. The IRES region in PVSRIPO was derived from HRV-2 and is heterologous to the POSA amplicon primer and probe sequences. The limit of detection for the assay was <100 copies of wild-type Polio IRES per $2.6 \times 10^7$ copies PVSRIPO in each PCR reaction. The copy number of the PVSRIPO test article was determined prior to testing through the use of TaqMan amplicons "PVS F" and "P01" targeting the HRV-2 IRES and polyprotein CDS regions in PVSRIPO which are described elsewhere. The method's LOD was verified at the time of the assay by sample spiking with Sabin type-1 Polio virus. Extracted Polio Sabin type-1 viral RNA was used to generate the standard curve (100 pg to 1 fg per reaction) and a 100 copy spike (~0.41 fg) with Polio Sabin type-1 RNA of the test article was used as the amplicon inhibition control and as a means of establishing the limit of detection for the assay. Test sample viral RNA was extracted using an approved Qiagen mini-prep method prior to the qPCR reaction. All standards and test sample reactions were performed in duplicate. The negative control was a no test control (NTC) reaction with nuclease free water. The general PCR inhibition and extraction controls consisted of heterologous internal positive control (IPC) DNA and associated IPC-specific primers and probe analyzed with the sample extracts during the concomitantly performed TaqMan qPCR analysis for residual Vero Host Cell DNA.

An Applied Biosystems 7900HT 96-well instrument is used to detect the accumulation of PCR amplification product continuously during the amplification process, allowing accurate target quantitation in the exponential phase of PCR. The use of a 96-well block allows for greater reaction volumes than a 384-well block and thus increases the assay sensitivity for residual DNA and contaminant RNA studies. TaqMan® qPCR chemistry utilizes a dual-labeled fluorogenic oligonucleotide TaqMan® probe. The TaqMan® probe used for detection of human genomic DNA is composed of an oligonucleotide end labeled with two fluorescent dyes with distinguishable emission maxima. The probe 5' terminus is labeled with a reporter dye, 6-FAM, and the 3' probe terminus is labeled with a non-fluorescent quenching dye. The oligonucleotide probe is homologous to an internal target sequence within the Polio type-1 and type-2 IRES region and is not cross-reactive to the HRV-2 derived IRES in PVSRIPO. A high rejection ratio of HRV-2 IRES to Polio IRES sequences is achieved by utilizing a highly heterologous region of the Polio IRES not present in HRV-2. While intact and in free solution, the probe quenching dye reduces the fluorochrome reporter emission via FRET. During the extension phase of a TaqMan® PCR reaction the probe is cleaved by the 5' nuclease activity of the Taq DNA polymerase, releasing the reporter dye from the probe and allowing an increase in reporter emission. Precise quantification of initial target in each PCR reaction occurs during the exponential ($\log^2$) phase of the amplification prior to reagent exhaustion or by-product inhibition of the reaction. However, due to signal to noise limits of the reaction and general background fluorescence, the most accurate data are typically generated late in log phase. Normalized reporter fluorescence is plotted versus time, represented by the PCR cycle number. Target copy numbers or mass values are generated by assigning a fluorescence threshold above background and determining the cycle point at which each sample's amplification plot reaches the threshold (defined as the threshold cycle or Ct). Threshold cycle values for each reaction are used to quantitate the amount of target initially contained within each test article reaction compared to known standards. Method controls and system suitability criteria must be met in order to report the sample results, including: NTC Ct scores, standard curve Ct scores and fit ($R^2$), and wild-type Polio RNA recoveries.

PVS-RIPO Final Vialed Product was tested for wild-type (or vaccine strain) Polio type-1 and type-2 IRES cDNA sequences using a TaqMan®-based RT-qPCR (Applied Biosystems Inc., Foster City, Calif.) amplicon targeting the Polio IRES. TaqMan® primers and a fluorescent dye-labeled probe were designed with ABI Primer Express software (Version 2.0.0). The 109-bp amplicon consists of a forward primer: 5'-(TTG GCG GCC TAC CTA TGG, SEQ ID NO: 11); reverse primer: 5'-(TGG GAT TAG CCG CAT TCA, SEQ ID NO: 12); and TaqMan® probe: 5'-[6FAM]-(AGC CTA TTG AGC TAC ATA AGA ATC CTC CGG C)-[Quencher], SEQ ID NO: 13. Primers and probe were diluted to 10 and 5 pmol/µL respectively with nuclease free water (NFW). The reaction mixture consisted of 25 µL TaqMan® RT-PCR Universal Master Mix without UNG, 1.5 µL NFW, 1 µL forward primer, 1 µL reverse primer, 0.5 µL TaqMan® probe and 20 µL sample (containing ~$2.6 \times 10^7$ copies PVSRIPO), for a 50 µL final reaction volume. Reaction mixtures were loaded into a 96-well plate, covered with optical film, and amplified with an ABI model 7900HT 96-well Sequence Detection System using a 4-stage qPCR profile (2:00 min, 50.0° C.; 45:00 min, 60.0° C.; 5:00 min, 95.0° C.; 45 cycles of 0:20 min, 94.0° C.; 1:00 min, 62.0° C.). A Polio Sabin type-1 strain standard curve made from purified viral RNA (WHO std., BDP Part #30374) was 10-fold serial-diluted into NFW from 100 pg to 1 fg (~$2.43 \times 10^7$ to ~243 copies/rxn).

RT-qPCR for HRV-2 IRES and Polio Polyprotein

The PVS-RIPO Final Vialed Product lot was tested to determine the PVSRIPO HRV-2 IRES (PVS-1), and Polio Polyprotein (P01) RNA load using a TaqMan®-based RT-qPCR (Applied Biosystems Inc., Foster City, Calif.) amplicon targeting the HRV-2 IRES (PVS-1) and Polio polyprotein genes (P01) in PVSRIPO.

The TaqMan® oligonucleotide probes are homologous to internal target sequences within the PVSRIPO HRV-2 derived IRES and the Polio Polyprotein RT-PCR amplicons and when used together are specific for PVSRIPO. Since PVSRIPO is a single-stranded RNA virus, sample extracts are reverse transcribed to cDNA using the amplification primers as part of the thermocycle protocol prior to qPCR amplification. While intact and in free solution, the probe quenching dye reduces the fluorochrome reporter emission via FRET. During the extension phase of a TaqMan® PCR reaction the probe is cleaved by the 5' nuclease activity of the Taq DNA polymerase, releasing the reporter dye from the probe and allowing an increase in reporter emission.

The ABI Prism 7900HT uses a dual-axis scanning head to distribute the excitation light from an argon-ion (488 nm) laser to all 96 wells. A CCD imager measures the fluorescence spectrum and intensity from each well to generate real-time spectral data during PCR amplification. ABI Sequence Detection Software (SDS) deconvolutes the fluorescence intensity of reporter, quencher, and normalizer (ROX) dyes and calculates the increase in normalized reporter emission intensity over the course of the amplification. The negative control was a no test control (NTC) reaction with nuclease free water, while the general PCR inhibition and extraction controls consist of a heterologous internal positive control (IPC) and associated IPC amplicon used with the sample extracts and performed concomitantly during the Vero host cell DNA amplification.

Precise quantification of initial target in each PCR reaction occurs during the exponential ($\log^2$) phase of the amplification prior to reagent exhaustion or by-product inhibition of the reaction. However due to signal to noise limits of the reaction and general background fluorescence, the most accurate data are typically generated late in log phase. Normalized reporter fluorescence is plotted versus time, represented by the PCR cycle number. Target copy numbers or mass values are generated by assigning a fluorescence threshold above background and determining the cycle point at which each sample's amplification plot reaches the threshold (defined as the threshold cycle or Ct). Threshold cycle values for each reaction are used to quantitate the amount of target initially contained within each test article reaction compared to known standards.

To perform the assay at the BDP, TaqMan® primers and a fluorescent dye-labeled probe were designed with ABI Primer Express software (Version 2.0.0). The 71-bp HRV-2 IRES (PVS-1) amplicon consists of a forward primer: 5'-(AAC CCA ATG TGT ATC TAG TCG TAA TGA, SEQ ID NO: 1); reverse primer: 5'-(TGA AAC ACG GAC ACC CAA AG, SEQ ID NO: 2); and TaqMan® probe: 5'-[6FAM]-(CAA TTG CGG GAT GGG ACC AAC T)-[BHQ], SEQ ID NO: 3. The 70-bp amplicon for P01 consists of a forward primer: 5'-(TTG GTG GGA ACG GTT CAC A, SEQ ID NO: 8); reverse primer: 5'-(TCA CCT TGA CTC TGA GTG AAG TAT GA, SEQ ID NO: 9); and TaqMan® probe: 5'-[6FAM]-(TTG CAG CGG CCC TGA AGC G)-[BHQ], SEQ ID NO: 10. Primers and probes were diluted to 10 and 5 pmol/µL respectively with nuclease free water (NFW). The reaction mixture consisted of 25 µL TaqMan® 1-step RT PCR 2× Master Mix with ROX dye, 1 µL RNase inhibitor, 1 µL NFW, 1 µL forward primer, 1 µL reverse primer, 1 µL TaqMan® probe and 20 µL test sample (50 µL final reaction volume). Reaction mixtures were loaded into a 96-well plate, covered with optical film, and amplified with an ABI model 7900HT 96-well Sequence Detection System using a 3-step qPCR profile (2:00 minutes, 50.0° C.; 30 minutes at 48.0° C. (RT-step); 10:00 minutes, 95.0° C.; 40 cycles of 0:15 minutes, 95.0° C.; 1:00 minutes, 60.0° C.). Amplicon cDNA standard curves were made from PVS-RIPO plasmid DNA and were 10-fold serial-diluted into NFW from 100 pg to 1 fg. Standard control samples were run in duplicate while three serial $\log_{10}$ dilutions (10 to 1000-fold dilutions) of the various PVS-RIPO test sample extracts were used to verify the performance of the RT step and quantitate the viral target copy numbers at the 1000-fold sample dilution. Control and sample viral RNA was extracted using a Qiagen mini-prep method following an approved procedure prior to the RT-qPCR reaction. The general PCR inhibition and extraction controls consisted of heterologous internal positive control (IPC) DNA and associated IPC-specific primers and probe analyzed with the sample extracts during the concomitantly performed TaqMan qPCR analysis for residual Vero Host Cell DNA. Buffer (NFW, no template) negative control samples were performed for the test. Both PVS-RIPO amplicons were run on the same 96-well plate to eliminate inter-assay variation. The PVS-RIPO RNA concentration in the test samples was calculated using the ABI 7900HT software by comparing the sample threshold cycle value with the plasmid DNA standard curve equation. Conversion from mass to viral copy numbers is based on the PVSRIPO plasmid (PCR standard) mass of ~10.8 ag/copy and the PVSRIPO viral genome mass of ~4.1 ag/copy.

Virus Particle by EM

Negative stain transmission electron microscopy (TEM) is used to quantitate the number of viral particles/mL in a test sample (PVSRIPO Final Vialed Product). Ten grid spaces were photographed and the number of viral particles in each section were enumerated and used to calculate the viral particles/mL.

The test sample was fixed by dilution with an equal volume of fixative (8% formaldehyde in 2×PBS). The test sample (0.5 µL) was placed on a prepared EMS CF200-Cu coated grid and allowed to air dry. The sample was then washed three times with 5 µL of double distilled water (DDH2O) to wash salt/phosphate buffer from the sample. Then 0.5% Uranyl Acetate aqueous solution was added (5 µL) onto the grid and allowed to air dry. The grid was examined by electron microscopy. Ten grid spaces were photographed and the number of viral particles determined by the following calculation:

virus particles (vp)=(average #vp)×(area of grid/area of photo)×(1 mL/the amount of virus added in µL)

Stability Testing for Final Vialed Product Lot L1402001

Stability testing of PVSRIPO Final Vialed Product Lot L1402001 (stored at ≤−70° C.) includes appearance, virus titer by $TCID_{50}$, endotoxin, pH, and bioburden. All tests are performed at 12, 24, 36, 48, 60, and 72 months. Virus titer is be performed at 6 months. Bioburden will not be performed at the zero time point because sterility is already performed as part of product release.

Stability results available are included in Table 10. Based on the $TCID_{50}$ results, PVSRIPO Final Vialed Product Lot L1402001 is stable for at least 6 months at ≤−70° C.

TABLE 10

Stability Results for PVSRIPO Final Vialed Product Lot L1402001, Stored at ≤−70° C.

| | | Time Point | |
|---|---|---|---|
| Test | Specification | 0 Months | 6 Months |
| Appearance | Clear to translucent, colorless liquid with no evidence of particulate matter | Clear to translucent colorless liquid with no particulate matter QC-053194 | Not Required |

TABLE 10-continued

Stability Results for PVSRIPO Final Vialed Product Lot L1402001, Stored at ≤−70° C.

| Test | Specification | Time Point | |
|---|---|---|---|
| | | 0 Months | 6 Months |
| Virus Titer by TCID$_{50}$ | Report Results | 4.48 × 10$^9$ TCID$_{50}$/mL QC-053192 | 3.98 × 10$^9$ TCID$_{50}$/mL QC-053848 |
| Endotoxin/LAL | ≤10 EU/mL | <0.5 EU/mL QC-053191 | Not Required |
| pH | 7.4 ± 0.5 | 7.2 QC-053196 | Not Required |
| Bioburden | No Growth | No Growth (Sterility) QC-053197 | Not Required |

In view of the many possible embodiments to which the principles of the disclosure may be applied, it should be recognized that the illustrated embodiments are only examples of the disclosure and should not be taken as limiting the scope of the invention. Rather, the scope of the invention is defined by the following claims. We therefore claim as my invention all that comes within the scope and spirit of these claims.

The invention claimed is:

1. A purification process for obtaining a composition comprising a live non-naturally occurring poliovirus, comprising:

separating an aqueous fluid comprising the live non-naturally occurring poliovirus on a size separation chromatography column;

measuring by quantitative polymerase chain reaction (qPCR) one or more nucleic acid sequences found in the live non-naturally occurring poliovirus in at least one fraction of the eluate from said size separation column;

collecting at least one positive fraction of the eluate from said size separation column containing the one or more nucleic acid sequences found in the live non-naturally occurring poliovirus;

pooling the at least one positive fraction;

separating the pooled at least one positive fraction on an anion exchange chromatography column; and collecting in at least one positive fraction of the flow-through eluate from said anion exchange chromatography column containing the live non-naturally occurring poliovirus.

2. A purification process for obtaining a composition comprising a live non-naturally occurring poliovirus, comprising:

separating an aqueous fluid comprising the live non-naturally occurring poliovirus on a Sepharose 6 fast flow (FF) separation chromatography column, collecting at least one positive fraction of the eluate from said Sepharose 6 FF separation column containing the one or more nucleic acid sequences found in the live non-naturally occurring poliovirus;

pooling the at least one positive fraction;

separating the pooled at least one positive fraction on a Super Q 650M resin anion exchange chromatography column, and collecting in at least one positive fraction of the flow-through eluate from said Super Q 650M resin anion exchange chromatography column containing the live non-naturally occurring poliovirus.

3. The method of claim 1, further comprising:

introducing plasmid DNA comprising a template sequence of the live non-naturally occurring poliovirus into one or more bacterial cells, thereby generating the one or more bacterial cells transformed with the plasmid DNA;

growing a solid phase culture of the one or more transformed bacterial cells, thereby generating one or more bacterial colonies;

detecting the presence of one or more nucleic acid sequences from the template sequence of the live non-naturally occurring poliovirus in at least one of the one or more bacterial colonies;

propagating a culture of bacterial cells from the at least one bacterial colony in which the presence of the one or more nucleic acid sequences was detected;

extracting the plasmid DNA comprising the template sequence of the live non-naturally occurring poliovirus from the propagated bacterial cells, wherein the bacterial cells are not frozen between the propagating and the extracting steps;

infecting mammalian host cells with the plasmid DNA;

culturing the mammalian host cells with the plasmid DNA;

obtaining liquid cell culture medium from the mammalian host cells, debris of the mammalian host cells, or both, which comprise the live non-naturally occurring poliovirus; and incubating the liquid cell culture medium from the mammalian host cells, debris of the mammalian host cells or both, with a nuclease enzyme capable of digesting free nucleic acids in solution but not encapsulated viral nucleic acids, thereby generating an aqueous fluid comprising the live non-naturally occurring poliovirus.

4. The purification process of claim 1, wherein the process does not contain any further chromatography separation steps after the anion exchange chromatography separation step.

5. The purification process of claim 1, wherein the process contains two chromatography separation steps.

6. The purification process of claim 1, further comprising concentrating by diafilatration the live non-naturally occurring poliovirus eluted in the flow-through eluate.

7. The purification process of claim 1 wherein the purification process is conducted in less than 8 hours.

8. The purification process of claim 1, wherein the purification yield of the purification process is at least 50%, wherein the yield of live non-naturally occurring poliovirus from the process is at least $5 \times 10^{11}$ pfu, wherein the infectivity of the live non-naturally occurring poliovirus eluted in the flow-through eluate is at least $1 \times 10^{12}$ Tissue Culture Infectious Dose $(TCID)_{50}$, or combinations thereof.

9. The purification process of claim 1, wherein the aqueous fluid comprising the live non-naturally occurring poliovirus is a liquid cell culture medium obtained by a process comprising culturing, in a one or more rounds of cell culture, host cells infected with the live non-naturally occurring poliovirus.

10. The purification process of claim 9, wherein the liquid cell culture medium is obtained by a process further comprising, after culturing, separating the liquid cell culture medium from the host cells, debris of the host cells or both.

11. The purification process of claim 9, wherein the liquid cell culture medium is obtained by a process further comprising incubating the liquid cell culture medium with a nuclease enzyme capable of digesting free nucleic acids in solution but not encapsulated viral nucleic acids.

12. The purification process of claim 9, wherein the live non-naturally occurring poliovirus is obtained by a process comprising:

introducing plasmid DNA comprising a template sequence of the live non-naturally occurring poliovirus into one or more bacterial cells, thereby generating the one or more bacterial cells transformed with the plasmid DNA;

growing a solid phase culture of the one or more transformed bacterial cells, thereby generating one or more bacterial colonies;

detecting the presence of one or more nucleic acid sequences from the template sequence of the live non-naturally occurring poliovirus in at least one of the one or more bacterial colonies;

propagating a culture of bacterial cells from the at least one bacterial colony in which the presence of the one or more nucleic acid sequences was detected; and extracting the plasmid DNA comprising the template sequence of the live non-naturally occurring poliovirus from the propagated bacterial cells, wherein the bacterial cells are not frozen between the propagating and the extracting steps.

13. The purification process of claim 9, wherein the host cells infected with the live non-naturally occurring poliovirus are obtained by a process comprising:

introducing plasmid DNA comprising a template sequence of the live non-naturally occurring poliovirus into one or more bacterial cells, thereby generating the one or more bacterial cells transformed with the plasmid DNA;

growing a solid phase culture of the one or more transformed bacterial cells, thereby generating one or more bacterial colonies;

detecting the presence of one or more nucleic acid sequences from the template sequence of the live non-naturally occurring poliovirus in at least one of the one or more bacterial colonies;

propagating a culture of bacterial cells from the at least one bacterial colony in which the presence of one or more nucleic acid sequence was detected;

extracting the plasmid DNA comprising the template sequence of the live non-naturally occurring poliovirus from the propagated bacterial cells, wherein the bacterial cells are not frozen between the propagating and the extracting steps;

generating naked RNA of the live non-naturally occurring poliovirus by in vitro translation of the template sequence; and introducing the naked RNA of the live non-naturally occurring poliovirus into host cells, thereby generating host cells infected with the live non-naturally occurring poliovirus.

14. The purification process of claim 3, wherein the plasmid is a bacterial plasmid comprising an *E. coli* origin of replication, and wherein the one or more bacterial cells are *E. coli* cells.

15. The purification process of claim 9, wherein the host cells are mammalian host cells.

16. The purification process of claim 3, wherein the mammalian host cells are Vero cells.

17. The process of claim 1, wherein the live non-naturally occurring poliovirus is an oncolytic poliovirus or a Sabin polio virus.

18. The process of claim 1, wherein the live non-naturally occurring poliovirus is PVS-RIPO.

19. The purification process of claim 1, wherein the purification yield of the purification process is at least 50%.

20. The purification process of claim 1, wherein the yield of live non-naturally occurring poliovirus from the process is at least $5 \times 10^{11}$ pfu.

21. The purification process of claim 1, wherein the infectivity of the live non-naturally occurring poliovirus eluted in the flow-through eluate is at least $1 \times 10^{12}$ Tissue Culture Infectious Dose $(TCID)_{50}$.

* * * * *

SEQUENCE LISTING

<160> NUMBER OF SEQ ID NOS: 13

<210> SEQ ID NO 1
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 1
aacccaatgt gtatctagtc gtaatga        27

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 2
tgaaacacgg acacccaaag        20

<210> SEQ ID NO 3
<211> LENGTH: 22
<212> TYPE: DNA
<213> ORGANISM: Artificial Sequence
<220> FEATURE:
<223> OTHER INFORMATION: Synthetic oligonucleotide probe

<400> SEQUENCE: 3
caattgcggg atgggaccaa ct        22

<210> SEQ ID NO 4
<211> LENGTH: 17
<212> TYPE: DNA
<213> ORGANISM: Artificial Sequence
<220> FEATURE:
<223> OTHER INFORMATION: Synthetic oligonucleotide primer

<400> SEQUENCE: 4
gtaaaacgac ggccagt        17

<210> SEQ ID NO 5
<211> LENGTH: 18

```
<212> TYPE: DNA
<213> ORGANISM: Artificial Sequence
<220> FEATURE:
<223> OTHER INFORMATION: Synthetic oligonucleotide primer

<400> SEQUENCE: 5
cctctgccca gcgtgaag                                                 18

<210> SEQ ID NO 6
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 6
cacagacacg cccatggat                                                19

<210> SEQ ID NO 7
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 7
cacccaagcc accaatggct ccaa                                          24

<210> SEQ ID NO 8
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 8
ttggtgggaa cggttcaca                                                19

<210> SEQ ID NO 9
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 9
tcaccttgac tctgagtgaa gtatga                                        26

<210> SEQ ID NO 10
<211> LENGTH: 19
<212> TYPE: DNA
<213> ORGANISM: Artificial Sequence
<220> FEATURE:
<223> OTHER INFORMATION: Synthetic oligonucleotide probe

<400> SEQUENCE: 10
ttgcagcggc cctgaagcg                                                19

<210> SEQ ID NO 11
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 11
```

-continued

```
ttggcggcct acctatgg                                                18

<210> SEQ ID NO 12
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 12
tgggattagc cgcattca                                                18

<210> SEQ ID NO 13
<211> LENGTH: 31
<212> TYPE: DNA
<213> ORGANISM: Artificial Sequence
<220> FEATURE:
<223> OTHER INFORMATION: Synthetic oligonucleotide probe

<400> SEQUENCE: 13
agcctattga gctacataag aatcctccgg c                                 31
```